United States Patent
Nakazawa et al.

(10) Patent No.: US 10,012,868 B2
(45) Date of Patent: *Jul. 3, 2018

(54) POLYMERIZABLE COMPOUND, POLYMER, POLYMERIZABLE COMPOSITION, FILM, AND HALF MIRROR FOR DISPLAYING PROJECTION IMAGE

(71) Applicant: FUJIFILM Corporation, Tokyo (JP)

(72) Inventors: Yuki Nakazawa, Kanagawa (JP);
Shunya Katoh, Kanagawa (JP);
Hiroshi Matsuyama, Kanagawa (JP);
Daisuke Hayashi, Kanagawa (JP);
Masaru Yoshikawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/273,784

(22) Filed: Sep. 23, 2016

(65) Prior Publication Data
US 2017/0009138 A1 Jan. 12, 2017

Related U.S. Application Data

(63) Continuation of application No. PCT/JP2015/059559, filed on Mar. 27, 2015.

(30) Foreign Application Priority Data

Mar. 28, 2014 (JP) .................................. 2014-069346
Sep. 5, 2014 (JP) .................................. 2014-181135
Mar. 17, 2015 (JP) .................................. 2015-053774

(51) Int. Cl.
G02F 1/1333 (2006.01)
G02F 1/13363 (2006.01)
(Continued)

(52) U.S. Cl.
CPC ........ *G02F 1/13363* (2013.01); *C07C 233/18* (2013.01); *C07C 233/52* (2013.01); *C07C 235/60* (2013.01); *C07D 295/192* (2013.01); *C07D 307/12* (2013.01); *C08F 222/1006* (2013.01); *C09D 4/00* (2013.01); *C09K 19/3068* (2013.01); *C09K 19/586* (2013.01); *G02F 1/133553* (2013.01); *C07C 2601/16* (2017.05);
(Continued)

(58) Field of Classification Search
CPC ............... G02F 1/1333; G02F 1/13363; G02F 1/133553; G02F 1/133723; G02F 1/133784; G02F 2001/133302; G02F 2001/133638; G02F 2202/023; G02F 2202/28; C09K 19/586; C09K 19/3068; C09K 2019/0448; C09K 2019/044; C09K 2219/03; C07C 2601/16; C07C 233/52; C07C 233/18; C07C 235/60; C08F 222/1006; C08F 2222/102; C07D 295/192; C07D 307/12; C09D 4/00
USPC .................................... 252/299.63; 349/183
See application file for complete search history.

(56) References Cited

U.S. PATENT DOCUMENTS 6,395,351 B1  5/2002  Benecke et al.
6,771,340 B1  8/2004  Yoshimi et al.
(Continued)

FOREIGN PATENT DOCUMENTS

JP  2001-042127 A  2/2001
JP  2001-527570 A  12/2001
(Continued)

OTHER PUBLICATIONS

International Search Report for PCT/JP2015/059559 dated Jun. 30, 2015.
Written Opinion for PCT/JP2015/059559 dated Jun. 30, 2016.
International Preliminary Report on Patentability, dated Oct. 13, 2016, from the International Bureau in counterpart International Application No. PCT/JP2015/059559.
Partial Supplementary European Search Report dated Aug. 10, 2017, from the European Patent Office in counterpart European Application No. 15837387.8 (cited in corresponding U.S. Appl. No. 15/448,975).
Extended European Search Report dated Aug. 2, 2017, from the European Patent Office in Counterpart European Application No. 15844672.4 (cited in corresponding U.S. Appl. No. 15/465,829).
Non-Final Office Action issued in U.S. Appl. No. 14/886,740 dated Sep. 13, 2016.
(Continued)

*Primary Examiner* — Geraldina Visconti
(74) *Attorney, Agent, or Firm* — Sughrue Mion, PLLC

(57) ABSTRACT

The present invention provides a polymerizable compound denoted by Formula (I): in the formula, $Z^1$ and $Z^2$ represent an arylene group, and the like, m represents 1 or 2, n represents an integer of 0 or 1, and when m is 2, n is 0, $L^1$, $L^2$, $L^3$, and $L^4$ each independently represent a linking group such as —C(=O)O— and —OC(=O)—, $T^3$ represents -$Sp^4$-$R^4$, X represents —O—, and the like, r represents 1 to 4, $Sp^1$, $Sp^2$, $Sp^3$, $Sp^4$, and $Sp^5$ each independently represent a single bond or a linking group, $R^1$ and $R^2$ each independently represent a polymerizable group, and $R^3$, $R^4$, and $R^5$ each independently represent a hydrogen atom, a polymerizable group, or the like; a polymerizable composition containing the polymerizable compound described above; a film formed of the polymerizable composition described above; and a half mirror for displaying a projection image including the film described above.

(I)

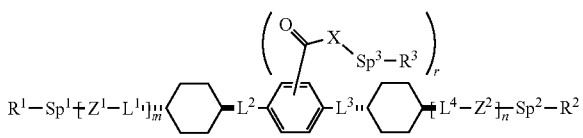

20 Claims, 2 Drawing Sheets

(51) Int. Cl.

| | | |
|---|---|---|
| C09K 19/58 | (2006.01) | |
| C07C 235/60 | (2006.01) | |
| C08F 222/10 | (2006.01) | |
| C09D 4/00 | (2006.01) | |
| G02F 1/1335 | (2006.01) | |
| C07C 233/18 | (2006.01) | |
| C07C 233/52 | (2006.01) | |
| C07D 295/192 | (2006.01) | |
| C07D 307/12 | (2006.01) | |
| C09K 19/30 | (2006.01) | |
| C09K 19/04 | (2006.01) | |
| G02F 1/1337 | (2006.01) | |

(52) U.S. Cl.
CPC .. *C08F 2222/102* (2013.01); *C09K 2019/044* (2013.01); *C09K 2019/0448* (2013.01); *C09K 2219/03* (2013.01); *G02F 1/133723* (2013.01); *G02F 1/133784* (2013.01); *G02F 2001/133302* (2013.01); *G02F 2001/133638* (2013.01); *G02F 2202/023* (2013.01); *G02F 2202/28* (2013.01)

(56) References Cited

U.S. PATENT DOCUMENTS

| | | | |
|---|---|---|---|
| 6,791,645 | B2 | 9/2004 | Yano et al. |
| 7,927,671 | B2 * | 4/2011 | Kato ............... C08F 26/06 252/299.5 |
| 8,425,988 | B2 * | 4/2013 | Hirai ............... C07D 303/22 252/299.61 |
| 8,771,810 | B2 | 7/2014 | Mizumura et al. |
| 9,678,384 | B2 * | 6/2017 | Ibaraki ............. G02F 1/133634 |
| 2002/0039159 | A1 | 4/2002 | Yano et al. |
| 2003/0178609 | A1 | 9/2003 | Hammond-Smith et al. |
| 2003/0224175 | A1 | 12/2003 | Morita et al. |
| 2009/0087590 | A1 | 4/2009 | Aiki et al. |
| 2011/0001088 | A1 | 1/2011 | Ootsuki et al. |
| 2013/0109825 | A1 | 5/2013 | Mizumura et al. |
| 2015/0175564 | A1 | 6/2015 | Sakamoto et al. |
| 2015/0344782 | A1 | 12/2015 | Matsuyama et al. |
| 2017/0009138 | A1 | 1/2017 | Nakazawa |
| 2017/0174991 | A1 * | 6/2017 | Katoh ............... C09K 19/3852 |
| 2017/0190821 | A1 * | 7/2017 | Katoh ............... C08F 222/14 |
| 2017/0242175 | A1 | 8/2017 | Ibaraki |

FOREIGN PATENT DOCUMENTS

| | | |
|---|---|---|
| JP | 2002-107541 A | 4/2002 |
| JP | 2003-315553 A | 11/2003 |
| JP | 2004-262884 A | 9/2004 |
| JP | 2006-096877 A | 4/2006 |
| JP | 2009-98596 A | 5/2009 |
| JP | 2010-024438 A | 2/2010 |
| JP | 2010-270108 A | 12/2010 |
| JP | 2011-237513 A | 11/2011 |
| JP | 2011-527570 A | 12/2011 |
| JP | 2013-216591 A | 10/2013 |
| JP | 2016-053149 A | 4/2016 |
| WO | 2011-162291 A1 | 12/2011 |
| WO | 2011/162291 A1 | 12/2011 |
| WO | 2014/010325 A1 | 1/2014 |
| WO | 2014/142026 A1 | 9/2014 |
| WO | 2015-147243 A1 | 10/2015 |
| WO | 2017/007007 A1 | 1/2017 |

OTHER PUBLICATIONS

Notice of Allowance issued in U.S. Appl. No. 14/866,740 dated Feb. 15, 2017.
International Search Report of PCT/JP2015/075153 dated Nov. 24, 2015 (PCT/ISA/210).
Written Opinion of PCT/JP2015/075153 dated Nov. 24, 2015 (PCT/ISA/237).
International Preliminary Report on Patentability with translation of written opinion dated Mar. 16, 2017 issued by the International Bureau in counterpart International Application No. PCT/JP2015/075153.
Non-Final Office Action issued in U.S. Appl. No. 15/273,784 dated Aug. 10, 2017.
International Search Report issued in PCT/JP2015/076836 dated Nov. 2, 2015.
Written Opinion of International Searching Authority issued in PCT/JP2015/076836 dated Nov. 2, 2015.
IPRP issued in PCT/JP2015/076836 dated Apr. 1, 2017.
Notification of Reasons for Refusal issued in JP 2016-546701 dated Oct. 31, 2017.
Extended European Search Report (EESR) dated Dec. 1, 2017 from the European Patent Office in European Application No. 15837387.8.
Office Action dated Nov. 21, 2017 from the Japanese Patent Office in Japanese Application No. 2014-213749.
Office Action dated Nov. 21, 2017 from the Japanese Patent Office in Japanese Application No. 2014-214404.
Office Action dated Mar. 6, 2018, from Japanese Patent Office in JP Application No. 2016-546701.

* cited by examiner

POLYMERIZABLE COMPOUND, POLYMER, POLYMERIZABLE COMPOSITION, FILM, AND HALF MIRROR FOR DISPLAYING PROJECTION IMAGE

CROSS-REFERENCE TO RELATED APPLICATIONS

This application is a continuation of PCT International Application No. PCT/JP2015/059559 filed on Mar. 27, 2015, which claims priorities under 35 U.S.C. § 119 (a) to Japanese Patent Applications No. 2014-069346 filed on Mar. 28, 2014, No. 2014-181135 filed on Sep. 5, 2014, and No. 2015-053774 filed on Mar. 17, 2015, the entire contents of which are incorporated herein by reference.

BACKGROUND OF THE INVENTION

1. Field of the Invention

The present invention relates to a novel polymerizable compound. In addition, the present invention relates to a polymerizable composition containing the novel polymerizable compound, a film prepared by using the polymerizable composition containing the novel polymerizable compound, and a half mirror for displaying a projection image prepared by using the polymerizable composition described above.

2. Description of the Related Art

It is possible to prepare various optical films such as a retardation film or a reflection film by using a polymerizable compound having liquid crystallinity. The birefringence of the polymerizable compound is one of properties closely associated with the optical properties of an optical film to be obtained. For example, it is possible to obtain a retardation film having a thin film thickness and desired retardation by using a liquid crystal having high birefringence (WO2011/162291A).

On the other hand, it is possible to obtain a reflection film having high selectivity in a reflection wavelength range with a film which is formed by using a polymerizable compound having low birefringence and by immobilizing a cholesteric liquid crystalline phase. In JP2004-262884A, it is disclosed that a low birefringence retardation film, or a reflection film having high selectivity in a reflection wavelength range are obtained by using a non-liquid crystalline (meth)acrylate compound having a specific structure along with a polymerizable liquid crystal compound.

SUMMARY OF THE INVENTION

An object of the present invention is to provide a novel polymerizable compound which is able to be used as a low birefringence liquid crystal. In addition, another object of the present invention is to provide a film such as a low birefringence retardation film or a reflection film having high selectivity in a reflection wavelength range.

The present inventors have studied compounds having various structures in order to attain the objects described above, and thus, have found that a novel compound having a structure similar to that of a known polymerizable compound in WO2014/010325A or JP2010-270108A has low birefringence, and has properties advantageous to the formation of a film, have further conducted studies on the basis of the findings, and thus, have completed the present invention.

That is, the present invention provides <1> to <22> described below.

<1> A polymerizable compound denoted by Formula (I).

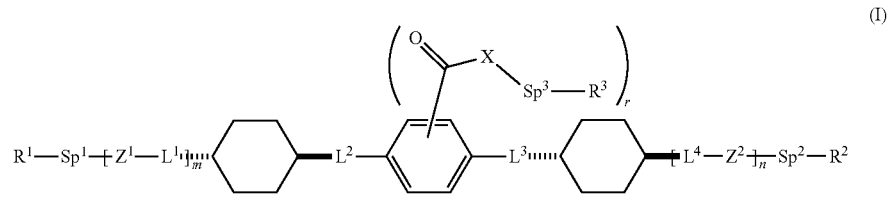

In the formula, $Z^1$ and $Z^2$ each independently represent a trans-1,4-cyclohexylene group which may have a substituent group, an arylene group which may have a substituent group, or a heteroarylene group which may have a substituent group, all of the substituent groups are each independently one to four substituent groups selected from the group consisting of —CO—X-$Sp^3$-$R^3$, an alkyl group, and an alkoxy group, m represents an integer of 1 or 2, and n represents an integer of 0 or 1, when m represents 2, n represents 0, when m represents 2, two $Z^1$'s may be identical to each other or different from each other, $L^1$, $L^2$, $L^3$, and $L^4$ each independently represent a linking group selected from the group consisting of a single bond, —O—, —CH$_2$O—, —OCH$_2$—, —(CH$_2$)$_2$OC(=O)—, —C(=O)O(CH$_2$)$_2$—, —NH—, N(CH$_3$)—, —S—, —C(=O)O—, —OC(=O)—, —OC(=O)O—, —C(=O)N(T$^3$)-, —N(T$^3$)C(=O)—, —C(=O)S—, —SC(=O)—, —CH$_2$C(=O)O—, —OC(=O)CH$_2$—, —CH=CH—C(=O)O—, —OC(=O)—CH=CH—, —CH=N—, —N=CH—, and —N=N—, T$^3$ represents -$Sp^4$-$R^4$, X represents —O—, —S—, or —N($Sp^5$-$R^5$)—, or represents a nitrogen atom forming a cyclic structure along with $R^3$ and $Sp^3$, r represents an integer of 1 to 4, $Sp^1$, $Sp^2$, $Sp^3$, $Sp^4$, and $Sp^5$ each independently represent a linking group selected from the group consisting of a single bond, a straight chain or branched alkylene group having 1 to 20 carbon atoms, and a group in which one or two or more —CH$_2$—'s in a straight chain or branched alkylene group having 1 to 20 carbon atoms are substituted with —O—, —S—, —NH—, —N(CH$_3$)—, —C(=O)—, —OC(=O)—, or —C(=O)O—, $R^1$ and $R^2$ each independently represent any one polymerizable group selected from the group consisting of groups denoted by Formula (Q-1) to Formula (Q-5) described below, and $R^3$, $R^4$, and $R^5$ each independently represent a hydrogen atom, a cycloalkyl group, a group in which one or two or more —CH$_2$—'s in a cycloalkyl group are substituted with —O—, —S—, —NH—, —N(CH$_3$)—, —C(=O)—, —OC(=O)—, or —C(=O)O—, or any one polymerizable group selected from the group consisting of the groups denoted by Formula (Q-1) to Formula (Q-5) described below, and in a case in which X is a nitrogen atom forming a cyclic structure along with R³ and Sp³, R³ may represent a single bond, and when Sp⁵ is a single bond, R⁵ is not a hydrogen atom.

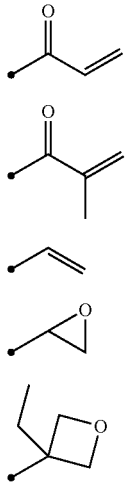

(Q-1)

(Q-2)

(Q-3)

(Q-4)

(Q-5)

<2> The polymerizable compound according to <1>, in which the arylene group is a 1,4-phenylene group.

<3> The polymerizable compound according to <1> or <2>, in which at least one of Z¹ or Z² is an arylene group which may have a substituent group or a heteroarylene group which may have a substituent group.

<4> The polymerizable compound according to any one of <1> to <3>, in which m+n is 2.

<5> The polymerizable compound according to <4>, in which m is 2, and two Z¹'s are each a trans-1,4-cyclohexylene group which may have a substituent group and an arylene group which may have a substituent group from an R¹ direction, or m is 1, n is 1, Z¹ is an arylene group which may have a substituent group, and Z² is an arylene group which may have a substituent group.

<6> The polymerizable compound according to any one of <1> to <5>, in which L² is —C(=O)O— from the R¹ direction, and L³ is —OC(=O)— from the R¹ direction.

<7> The polymerizable compound according to any one of <1> to <6>, in which R¹ and R² each independently represent the group denoted by Formula (Q-1) or the group denoted by Formula (Q-2).

<8> The polymerizable compound according to any one of <1> to <3>, in which m is 1, n is 1, r is 1, Sp³ is a straight chain or branched alkylene group having 1 to 20 carbon atoms, and R³ is a hydrogen atom.

<9> The polymerizable compound according to <1> or <2>, in which m is 1, n is 1, and both of Z¹ and Z² are a trans-1,4-cyclohexylene group which may have a substituent group.

<10> The polymerizable compound according to any one of <1> to <9>, in which all of L¹, L², L³, and L⁴ are —C(=O)O— or —OC(=O)—.

<11> A polymer obtained by performing a polymerization reaction with respect to the polymerizable compound according to any one of <1> to <10>.

<12> A polymerizable composition, containing: the polymerizable compound according to any one of <1> to <10>.

<13> The polymerizable composition according to <12>, further containing: other liquid crystal compounds along with the polymerizable compound denoted by Formula (I).

<14> The polymerizable composition according to <12> or <13>, further containing: a cross-linking agent.

<15> The polymerizable composition according to any one of <12> to <14>, further containing: a polymerization initiator.

<16> The polymerizable composition according to any one of <12> to <15>, further containing: a chiral compound.

<17> A film, comprising: a layer obtained by curing the polymerizable composition according to any one of <12> to <16>.

<18> A film, comprising: two or more layers obtained by curing the polymerizable composition according to any one of <12> to <16>.

<19> The film according to <17> or <18>, in which the film has selective reflection, and Δλ/λ which is a ratio of a half-width Δλ in a wavelength range of the selective reflection to a center wavelength λ of the selective reflection is less than or equal to 0.09.

<20> The film according to any one of <17> to <19>, in which the film reflects visible light.

<21> A film, comprising: at least three layers formed of the polymerizable composition according to any one of <12> to <16>, in which the three layers are a layer formed by immobilizing a cholesteric liquid crystalline phase having a center wavelength of selective reflection in a red light wavelength range, a layer formed by immobilizing a cholesteric liquid crystalline phase having a center wavelength of selective reflection in a green light wavelength range, and a layer formed by immobilizing a cholesteric liquid crystalline phase having a center wavelength of selective reflection in a blue light wavelength range.

<22> A half mirror for displaying a projection image, comprising: the film according to <21>.

<23> The half mirror for displaying a projection image according to <22>, further comprising: a substrate which is inorganic glass or an acrylic resin.

<24> The half mirror for displaying a projection image according to <22> or <23>, further comprising: an antireflection layer on an outermost surface.

According to the present invention, a novel polymerizable compound which is able to be used as a low birefringence liquid crystal is provided. In addition, the present invention provides a low birefringence retardation film, or a novel film such as a reflection film having high selectivity in a reflection wavelength range.

DESCRIPTION OF THE PREFERRED EMBODIMENTS

Figure 1:
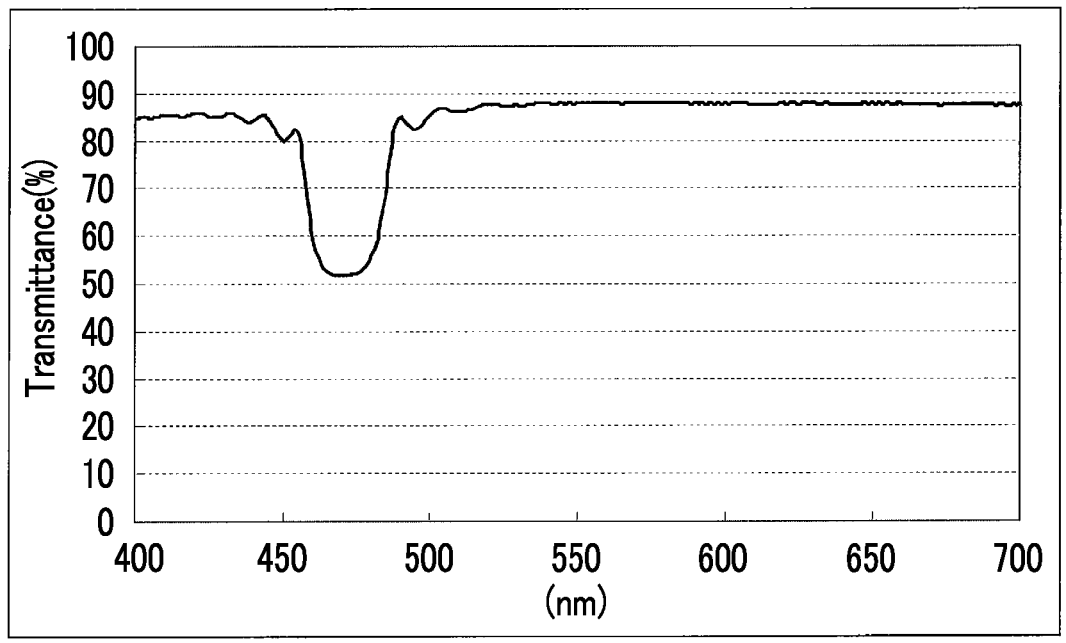
FIG. 1 is a diagram illustrating a transmission spectrum of a selective reflection film 1 prepared in an example.

Hereinafter, the present invention will be described in detail. Furthermore, herein, a numerical range denoted by using "to" indicates a range including the numerical values before and after "to" as the lower limit value and the upper limit value.

Herein, "(meth)acrylate" indicates "any one or both of acrylate and methacrylate". The same applies to "(meth)

acryl group" or the like, and "(meth)acryloyl group" indicates "any one or both of an acryloyl group and a methacryloyl group".

Herein, retardation indicates in-plane retardation, and indicates in-plane retardation at a wavelength of 550 nm, unless otherwise a wavelength is stated.

Herein, the in-plane retardation is measured by using a polarization retardation analysis device AxoScan manufactured by Axometrics, Inc. The in-plane retardation at a wavelength of λ nm is able to be measured by allowing light having a wavelength of X nm to be incident in a film normal direction using KOBRA 21ADH or WR (manufactured by Oji Scientific Instruments).

<Polymerizable Compound Denoted by Formula (I)>

Hereinafter, each group in Formula (I) will be described.

A steric cyclohexylene group in Formula (I) indicates relative arrangement, that is, indicates a trans-1,4-cyclohexylene group.

$Z^1$ and $Z^2$ each independently represent a trans-1,4-cyclohexylene group which may have a substituent group, an arylene group which may have a substituent group, or a heteroarylene group which may have a substituent group.

It is preferable that at least one of $Z^1$ or $Z^2$, in which the number of any of $Z^1$'s and $Z^2$'s may be two, is a trans-1,4-cyclohexylene group which may have a substituent group, as one embodiment of the polymerizable compound denoted by Formula (I). That is, it is preferable that at least one of $Z^1$ or $Z^2$, in which the number of any of $Z^1$'s and $Z^2$'s may be two, is an arylene group which may have a substituent group or a heteroarylene group which may have a substituent group.

When m and n are each 1, it is preferable that $Z^1$ and $Z^2$ are each an arylene group which may have a substituent group or a heteroarylene group which may have a substituent group, and it is more preferable that $Z^1$ and $Z^2$ are each an arylene group which may have a substituent group. When m is 2, at least one of $Z^1$'s is an arylene group which may have a substituent group or a heteroarylene group which may have a substituent group, and it is preferable that at least one of $Z^1$'s is an arylene group which may have a substituent group. In particular, it is preferable that $Z^1$ closer to a cyclohexyl group bonded to $L^2$ is an arylene group which may have a substituent group or a heteroarylene group which may have a substituent group.

The arylene group is a divalent group configured by subtracting two hydrogen atoms (hydrogen radicals) from an aromatic compound. It is preferable that the aromatic compound is a 5-membered to 18-membered ring. In addition, the heteroarylene group is a divalent group configured by subtracting two hydrogen atoms (hydrogen radicals) from an aromatic heterocyclic compound. It is preferable that the aromatic heterocyclic compound is a 5-membered to 18-membered ring.

Hereinafter, examples of the aromatic compound and the aromatic heterocyclic compound will be described, but the present invention is not limited thereto.

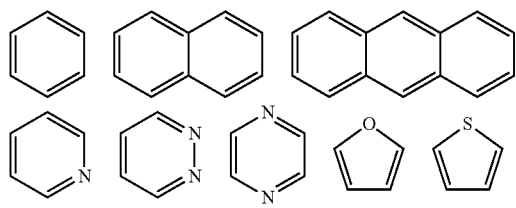

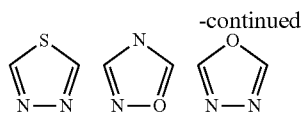
-continued

In particular, a phenylene group is preferable as the arylene group, and a 1,4-phenylene group is particularly preferable.

In the arylene group, the heteroarylene group, and the trans-1,4-cyclohexylene group "which may have a substituent group", all of the substituent groups are a substituent group selected from the group consisting of —CO—X-$Sp^3$-$R^3$, an alkyl group, and an alkoxy group. In addition, the number of substituent groups may be 1 to 4. When the number of substituent groups is greater than or equal to 2, two or more substituent groups may be identical to each other or different from each other.

Herein, the alkyl group may be either a straight chain or branched chain alkyl group. The number of carbon atoms of the alkyl group is preferably 1 to 30, is more preferably 1 to 10, and particularly preferably 1 to 6. Examples of the alkyl group are able to include a methyl group, an ethyl group, an n-propyl group, an isopropyl group, an n-butyl group, an isobutyl group, a sec-butyl group, a tert-butyl group, an n-pentyl group, an isopentyl group, a neopentyl group, an 1,1-dimethyl propyl group, an n-hexyl group, an isohexyl group, a straight chain or branched chain heptyl group, an octyl group, a nonyl group, a decyl group, a undecyl group, or a dodecyl group. The same description with respect to the alkyl group described above applies to an alkoxy group including the alkyl group. In addition, herein, in the alkylene group, specific examples of the alkylene group include a divalent group or the like obtained by subtracting arbitrary one hydrogen atom from each of the examples of the alkyl group described above.

Herein, the number of carbon atoms of a cycloalkyl group is preferably 3 to 20, and is more preferably greater than or equal to 5, and is preferably less than or equal to 10, and is more preferably less than or equal to 8, and is even more preferably less than or equal to 6. Examples of the cycloalkyl group are able to include a cyclopropyl group, a cyclobutyl group, a cyclopentyl group, a cyclohexyl group, a cycloheptyl group, and a cyclooctyl group.

m represents an integer of 1 or 2, and n represents an integer of 0 or 1. Here, when m represents 2, n represents 0. That is, the polymerizable compound denoted by Formula (I) has 4 or 5 cyclic groups. When m represents 2, two $Z^1$'s may be identical to each other or different from each other.

It is preferable that the polymerizable compound denoted by Formula (I) has a structure in which the 1,4-phenylene group and the trans-1,4-cyclohexylene group alternately exist, and for example, it is preferable that m is 2, n is 0, and $Z^1$'s are each a trans-1,4-cyclohexylene group which may have a substituent group and an arylene group which may have a substituent group from the $R^1$ side, or m is 1, n is 1, $Z^1$ is an arylene group which may have a substituent group, and $Z^2$ is an arylene group which may have a substituent group.

$L^1$, $L^2$, $L^3$, and $L^4$ each independently represent a linking group selected from the group consisting of a single bond, —O—, —$CH_2$O—, —O$CH_2$—, —$(CH)_2$OC(=O)—, —C(=O)O$(CH_2)_2$—, —NH—, N($CH_3$)—, —S—, —C(=O)O—, —OC(=O)—, —OC(=O)O—, —C(=O)N($T^3$)-, —N($T^3$)C(=O)—, —C(=O)S—, —SC(=O)—, —$CH_2$C(=O)O—, —OC(=O)$CH_2$—, —CH=CH—C(=O)O—, —OC(=O)—CH=CH—, —CH=N—, —N=CH—, and —N=N—. Furthermore, herein, when a divalent linking group is described as described above, bonding on a left side (in a case of "—CH₂O—", "C") is on the R¹ side in Formula (I), and bonding on a right side (in a case of "—CH₂O—", "O") is on the R² side in Formula (I). It is preferable that $L^1$, $L^2$, $L^3$, and $L^4$ are each independently —C(=O)O— or —OC(O)—, it is more preferable that $L^2$ is —C(=O)O—, and $L^3$ is —OC(=O)—, and it is more preferable that $L^1$ is —OC(=O)—, $L^2$ is —C(=O)O—, $L^3$ is —OC(=O)—, and $L^4$ is —C(=O)O—.

$T^3$ represents -$Sp^4$-$R^4$, and is preferably a hydrogen atom ($Sp^4$ is a single bond, and $R^4$ is a hydrogen atom).

X represents —O—, —S—, or —N($Sp^5$-$R^5$)—, and is preferably —O—. In addition, X may represent a nitrogen atom forming a cyclic structure along with $R^3$ and $Sp^3$. That is, —X-$Sp^3$-$R^3$ may be a nitrogen-containing cyclic group bonded to the adjacent carbonyl group by a nitrogen atom. Examples of the nitrogen-containing cyclic group include an 1-piperidyl group, an 1-piperidinyl group, an 1-pyrrolidyl group, and the like.

r represents an integer of 1 to 4, and is preferably 1. That is, the polymerizable compound denoted by Formula (I) has a structure having at least one substituent group bonded to a 1,4-phenylene group, in which the trans-1,4-cyclohexylene group is bonded to both sides through each of $L^2$ and $L^3$, by a carbonyl group, and in the substituent group, the carbonyl group is bonded to —O—, —S—, or —N($Sp^5$-$R^5$)—. It is particularly preferable that the substituent group bonded to the 1,4-phenylene group described above is bonded by C of —(C=O)—O—.

$Sp^1$, $Sp^2$, $Sp^3$, $Sp^4$, and $Sp^5$ each independently represent a linking group selected from the group consisting of a single bond, a straight chain or branched alkylene group having 1 to 20 carbon atoms, and a group in which one or two or more —CH₂—'s in a straight chain or branched alkylene group having 1 to 20 carbon atoms are substituted with —O—, —S—, —NH—, —N(CH₃)—, —C(=O)—, —OC(=O)—, or —C(=O)O—. It is preferable that $Sp^1$ and $Sp^2$ are each independently a linking group having one or more structural units selected from the group consisting of a straight chain alkylene group having 1 to 10 carbon atoms in which —O— is bonded to each of both terminals, —OC(=O)—(CH₂)₂—, —C(=O)O—(CH₂)₂—, —O—(CH₂)₂—, —(CH₂)₂—OC(=O)—, —(CH₂)₂—C(=O)O—, and —(CH₂)₂—O—. It is preferable that $Sp^3$, $Sp^4$, and $Sp^5$ are each independently a single bond, a straight chain alkylene group having 1 to 10 carbon atoms, or a straight chain alkylene group having 1 to 10 carbon atoms in which —O— is bonded to one terminal.

$R^1$ and $R^2$ each independently represent any one polymerizable group selected from the group consisting of groups denoted by Formula (Q-1) to Formula (Q-5) described below.

$R^3$, $R^4$, and $R^5$ each independently represent any one polymerizable group selected from the group consisting of a hydrogen atom, a cycloalkyl group, a group in which one or two or more —CH₂—'s in a cycloalkyl group are substituted with —O—, —S—, —NH—, —N(CH₃)—, —C(=O)—, —OC(=O)—, or —C(=O)O—, or the groups denoted by Formula (Q-1) to Formula (Q-5) described below.

(Q-1)

(Q-2)

(Q-3)

(Q-4)

(Q-5)

Specifically, examples of the group in which one or two or more —CH₂—'s in the cycloalkyl group are substituted with —O—, —S—, —NH—, —N(CH₃)—, —C(=O)—, —OC(=O)—, or —C(=O)O— include a tetrahydrofuranyl group, a pyrrolidinyl group, an imidazolidinyl group, a pyrazolidinyl group, a piperidyl group, a piperidinyl group, a morpholinyl group, and the like. A substitution position is not particularly limited. Among them, the tetrahydrofuranyl group is preferable, and a 2-tetrahydrofuranyl group is particularly preferable.

$R^3$ may represent a single bond in a case where X is a nitrogen atom forming a cyclic structure along with $R^3$ and $Sp^3$. In addition, when $Sp^5$ is a single bond, $R^5$ is not a hydrogen atom.

An acryloyl group (Formula (Q-1)) or a methacryloyl group (Formula (Q-2)) is preferable as the polymerizable group.

In addition, it is preferable that $R^3$, $R^4$, and $R^5$ are each a hydrogen atom.

It is also preferable that the polymerizable compound denoted by Formula (I) is a polymerizable compound in which m is 1, n is 1, both of $Z^1$ and $Z^2$ are a trans-1,4-cyclohexylene group which may have a substituent group. At this time, it is more preferable that r is 1. Further, it is preferable that the polymerizable compound denoted by Formula (I) is a compound denoted by Formula (I-1) described below.

(I-1)

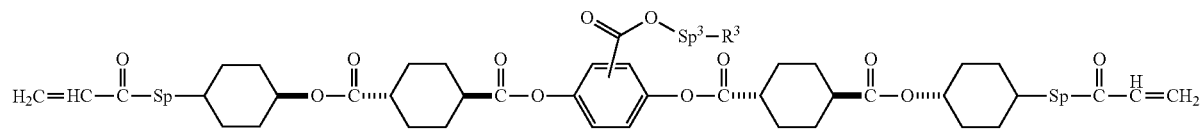

In the formula, the definition of Sp³ and R³ is identical to that in Formula (I).

Sp's each independently represent a linking group selected from the group consisting of a single bond, a straight chain or branched alkylene group having 1 to 20 carbon atoms, and a group in which one or two or more —CH₂—'s in a straight chain or branched alkylene group having 1 to 20 carbon atoms are substituted with —O—, —S—, —NH—, —N(CH₃)—, —C(=O)—, —OC(O)—, or —C(=O)O—.

All of Sp's are preferably a group in which one or two or more —CH₂—'s in a straight chain or branched alkylene group having 1 to 20 carbon atoms are substituted with —O—, —OC(=O)—, or —C(=O)O—, are more prefer-ably a group in which —CH₂— on one terminal in a straight chain or branched alkylene group having 1 to 20 carbon atoms is substituted with —O—, and —CH₂— on the other terminal is substituted with —C(=O)O—, and which is bonded to a cyclohexylene group by an oxygen atom of —C(=O)O—, and bonded to —C(=O)— by —O—, and are even more preferably —O—C₄H₈—O—C(=O)— or —C(=O)—O—C₄H₈—O— which is a group bonded to a cyclohexylene group by an oxygen atom of —C(=O)O— and to —C(=O)— by —O—.

Hereinafter, the polymerizable compound denoted by Formula (I) will be exemplified, but the present invention is not limited thereto.

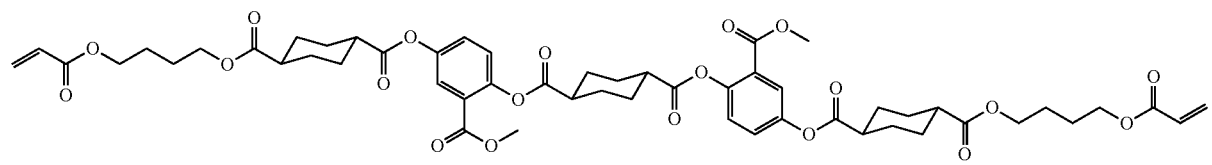

1

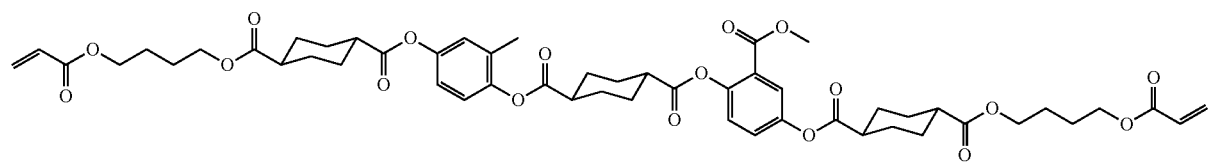

2

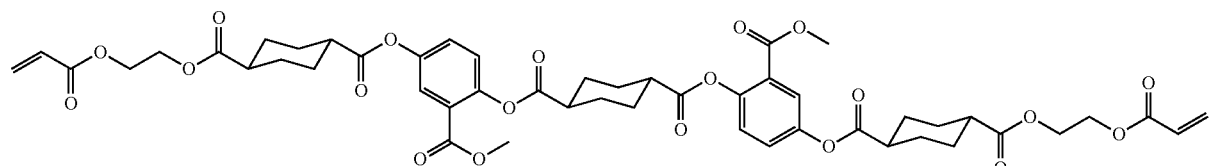

3

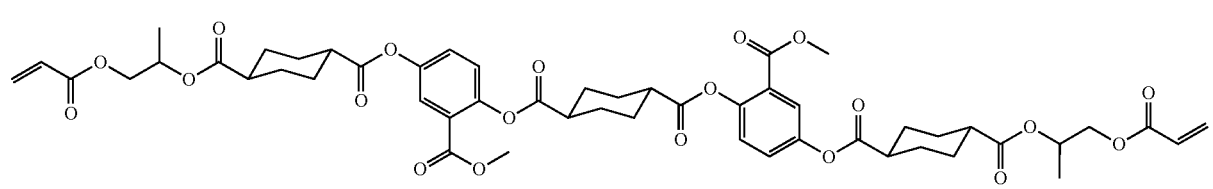

4

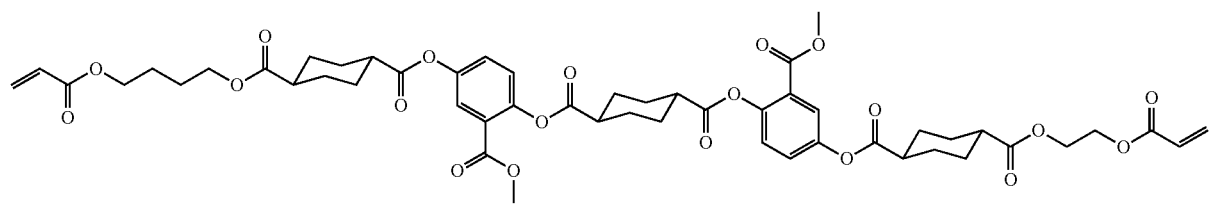

5

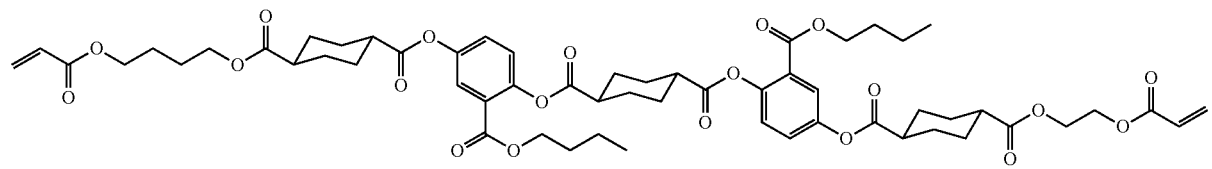

6

-continued
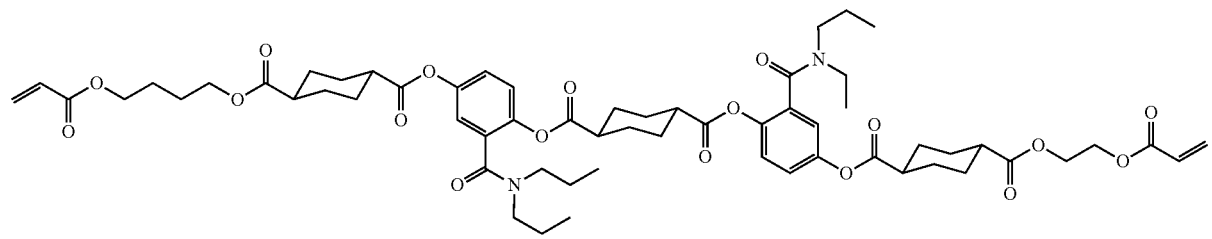
7
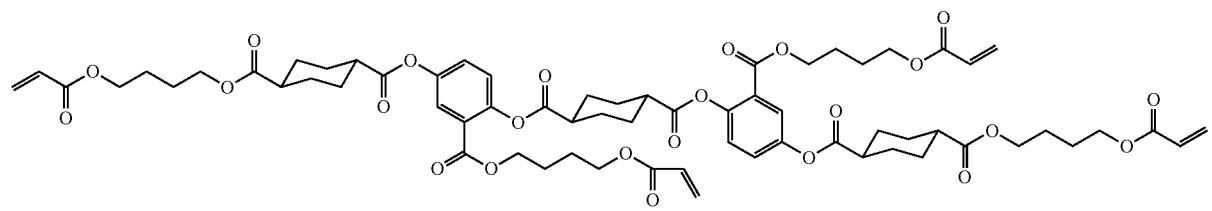
8
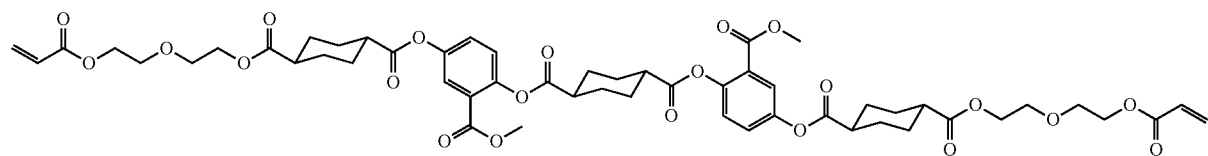
9
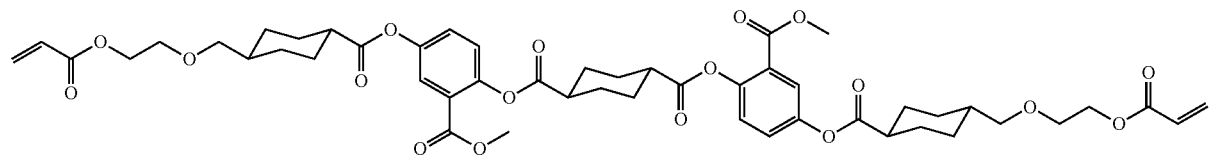
10
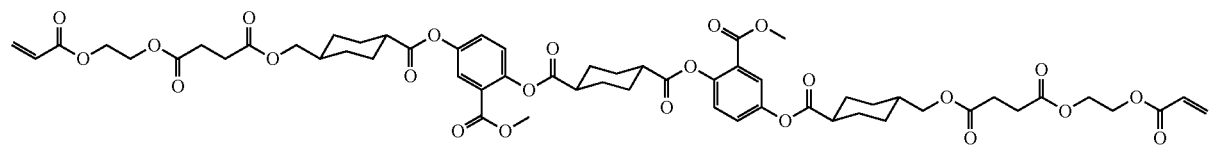
11
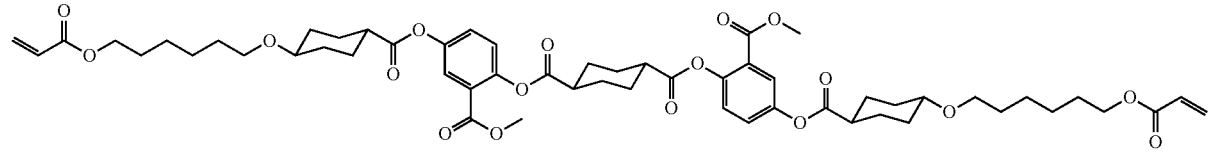
12
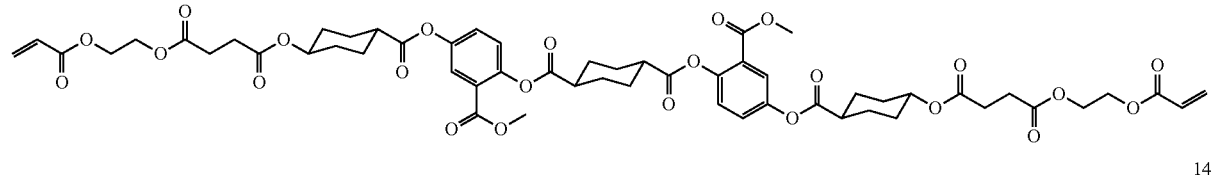
13
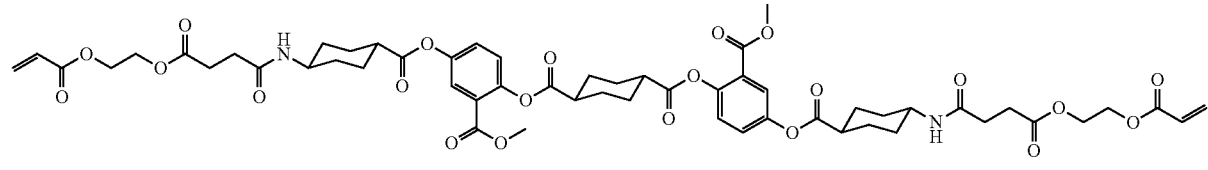
14

-continued
15
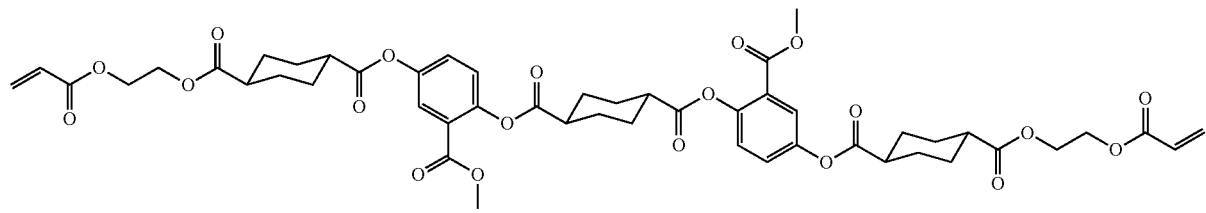
16
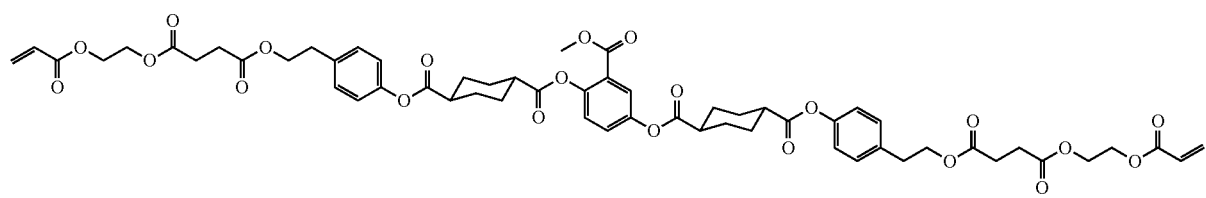
17
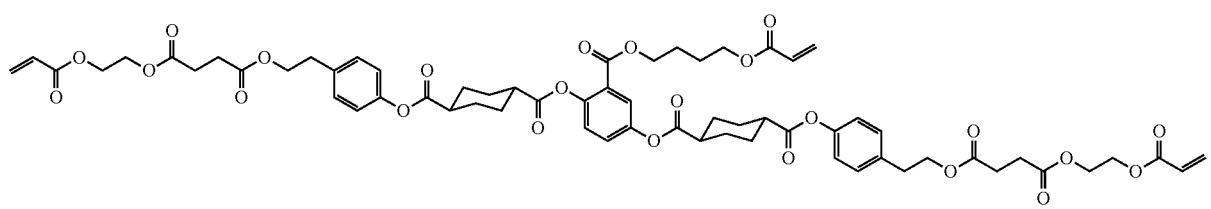
18
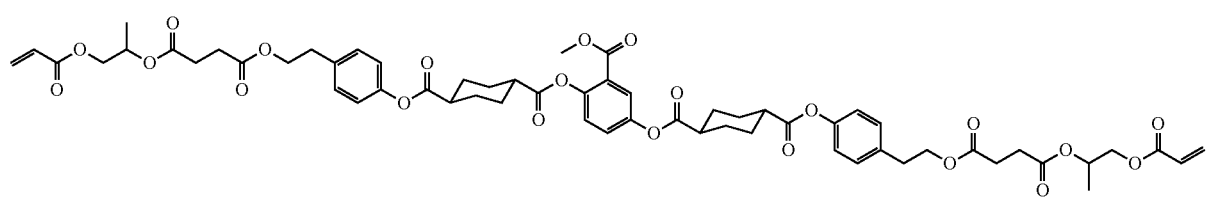
19
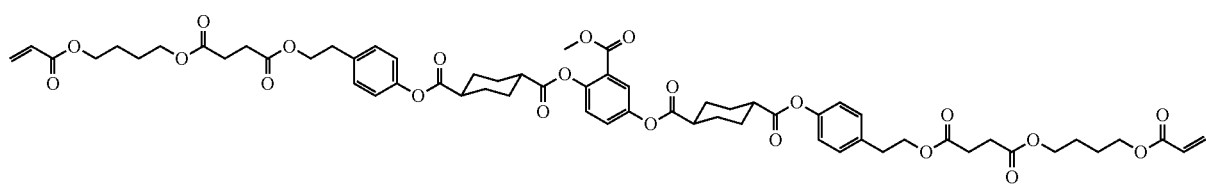
20
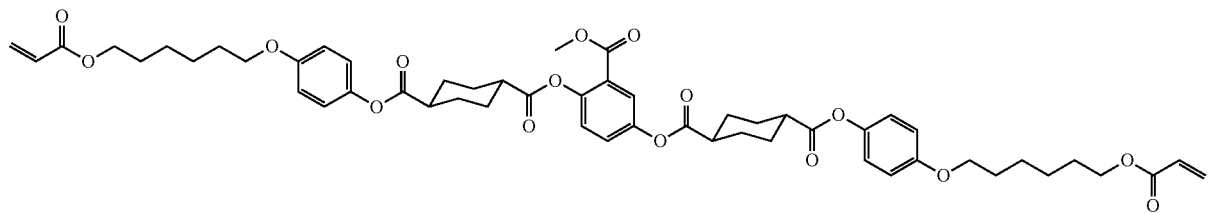
21
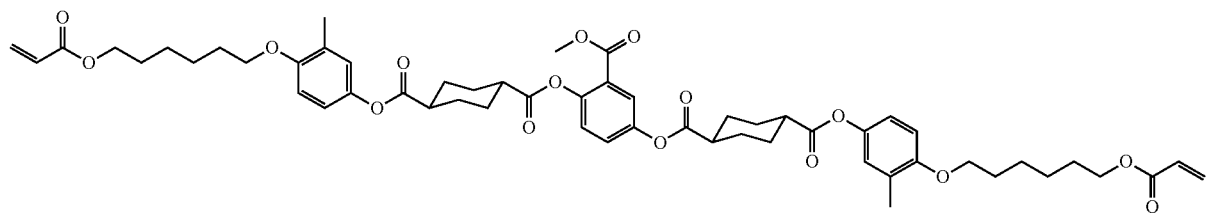

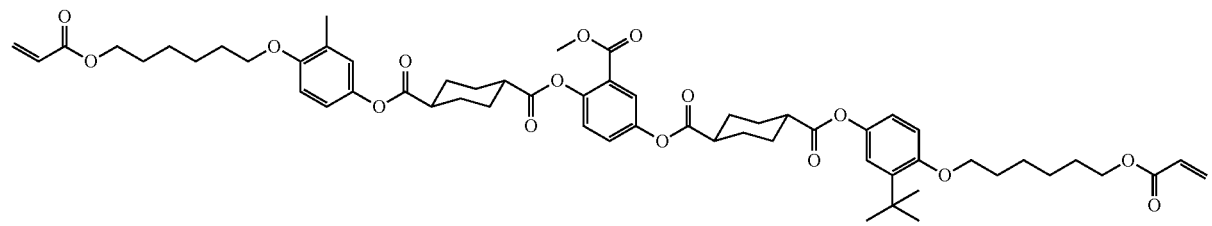
22
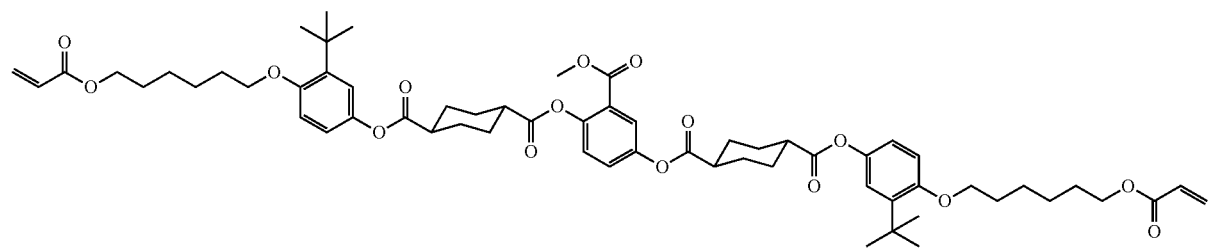
23
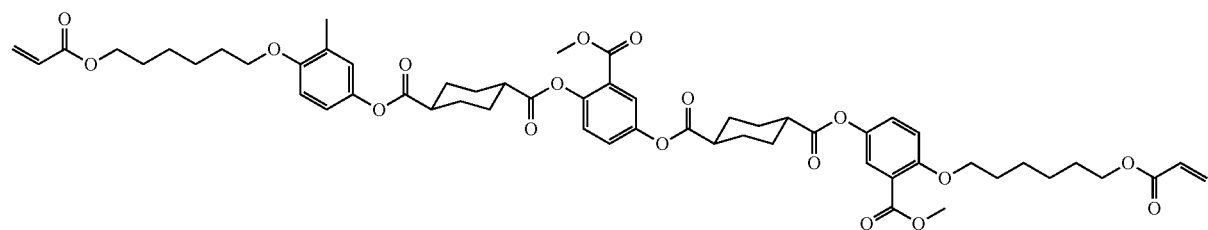
24
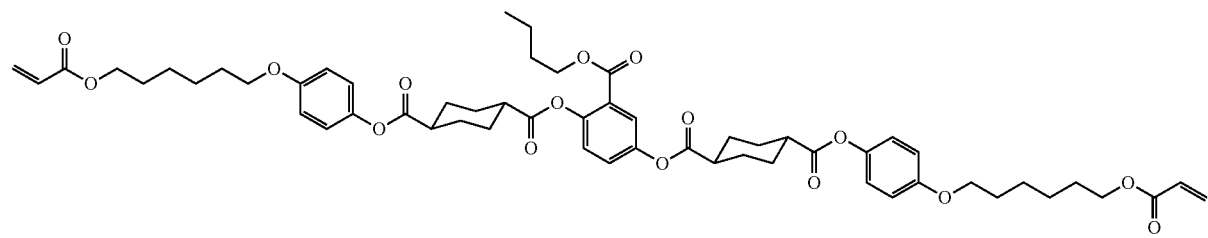
25
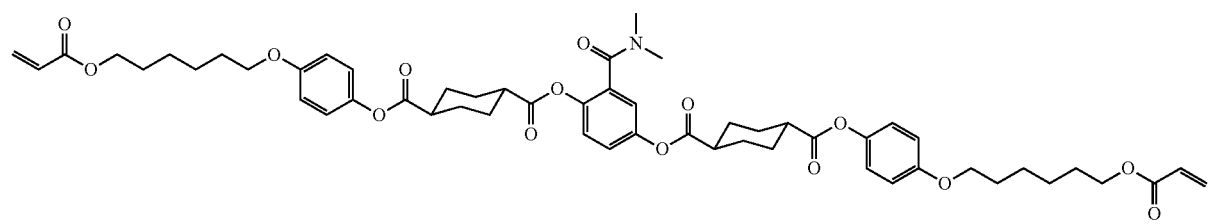
26
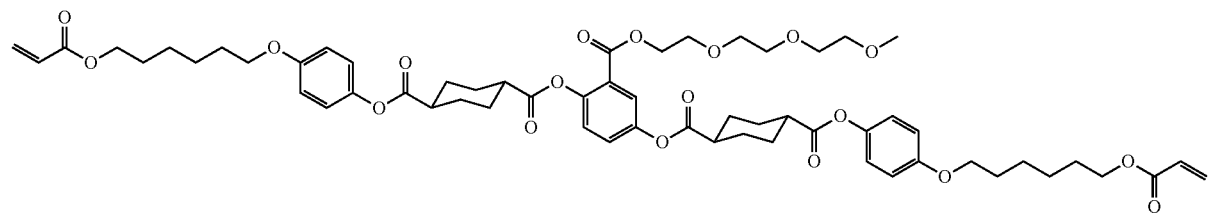
27

-continued
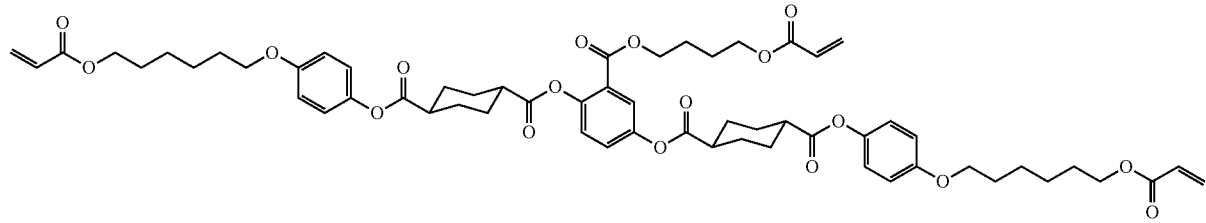
28
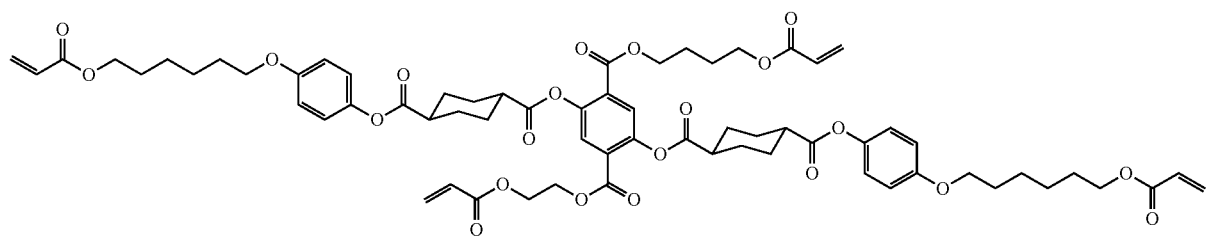
29
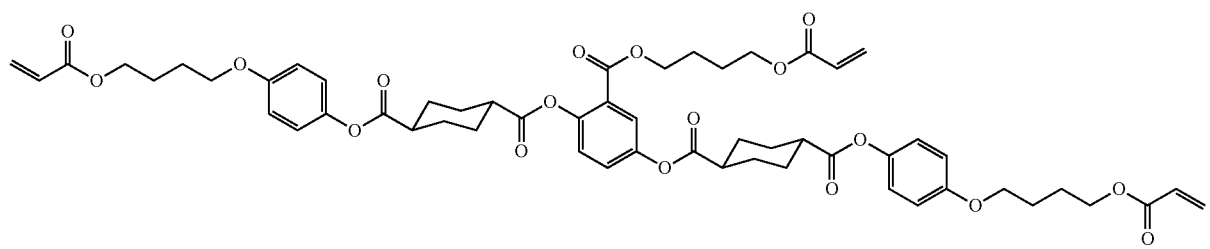
30
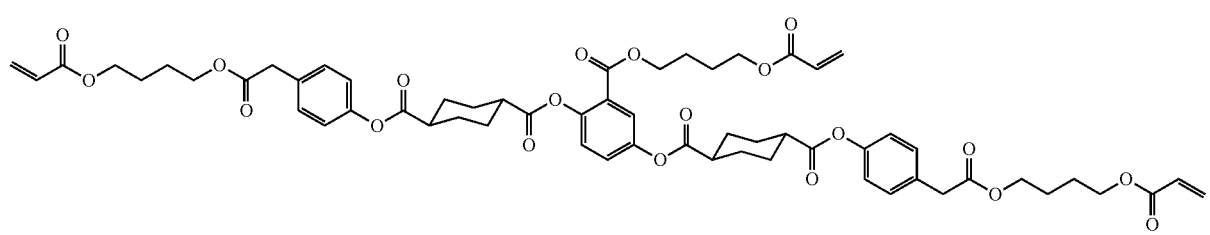
31
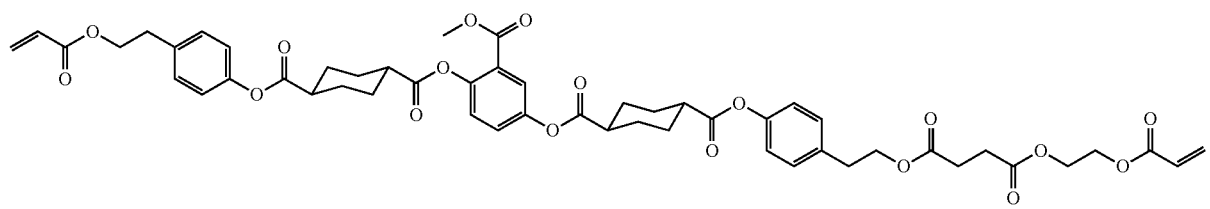
32
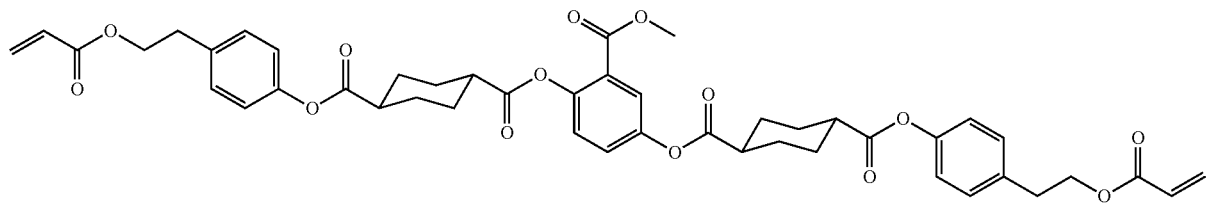
33

-continued
34
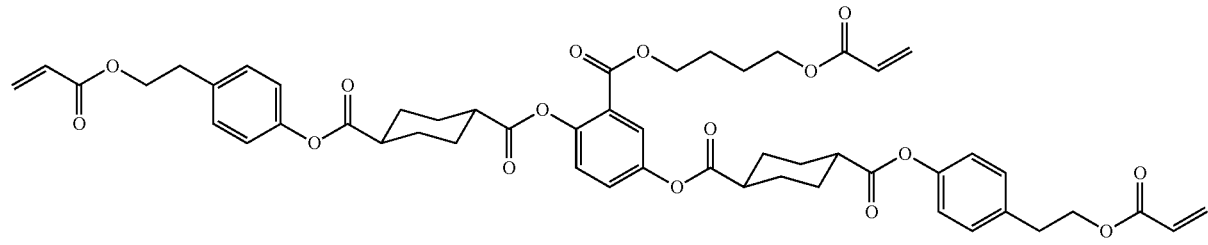
35
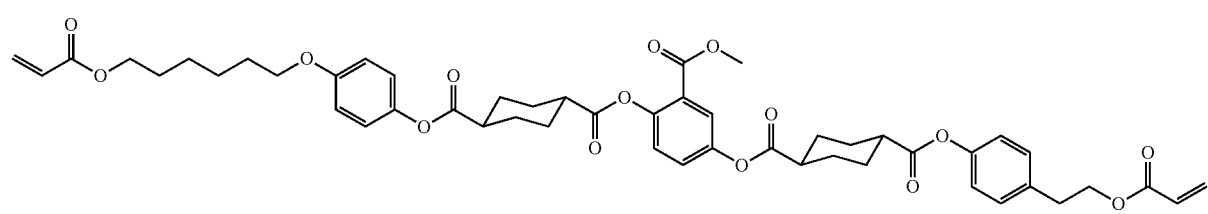
36
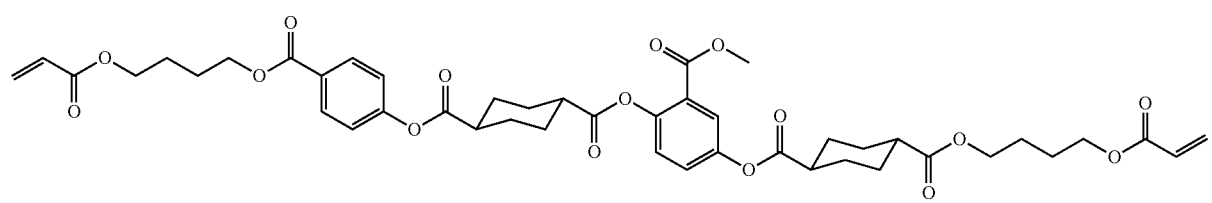
37
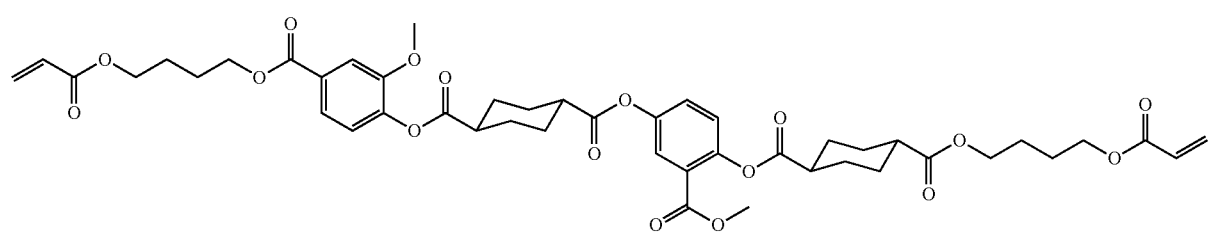
38
39
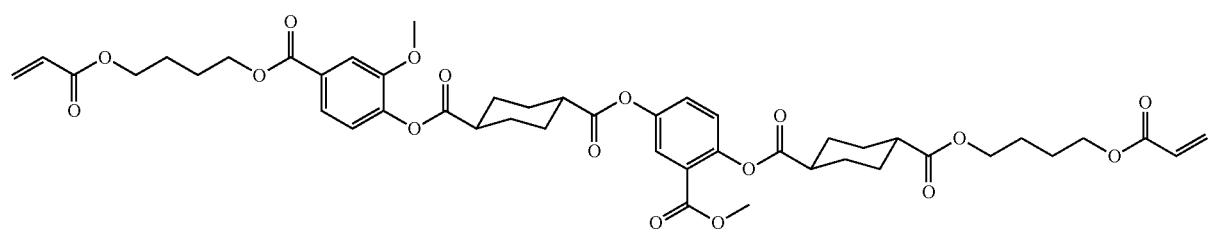

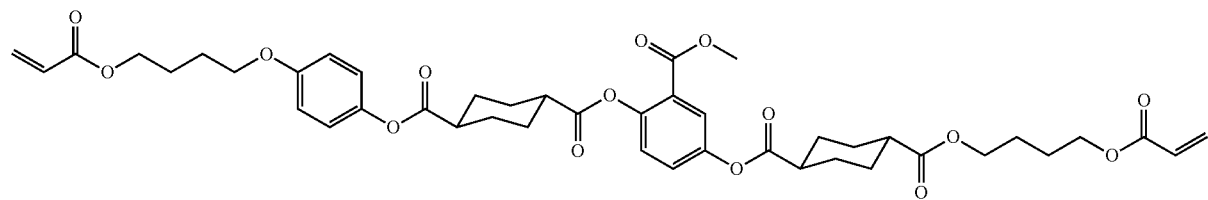
40
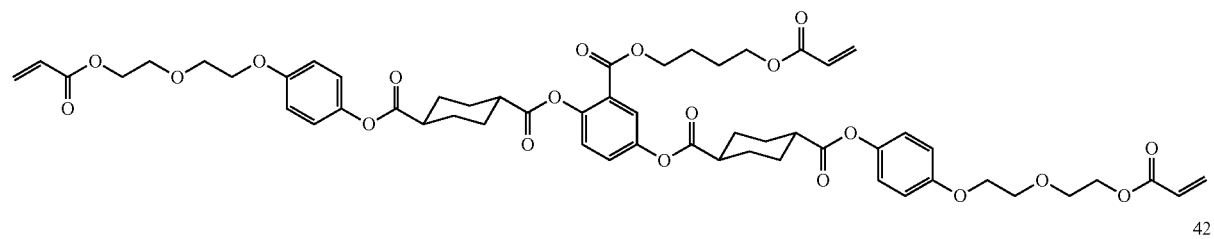
41
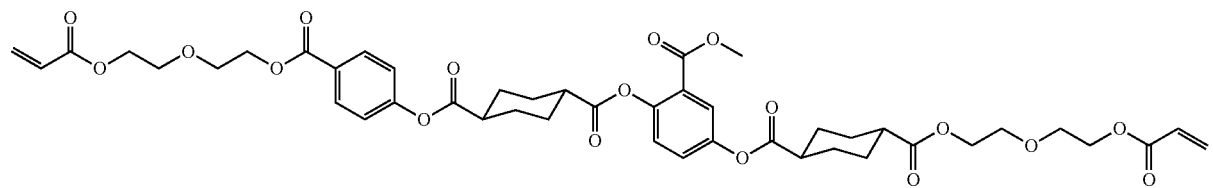
42
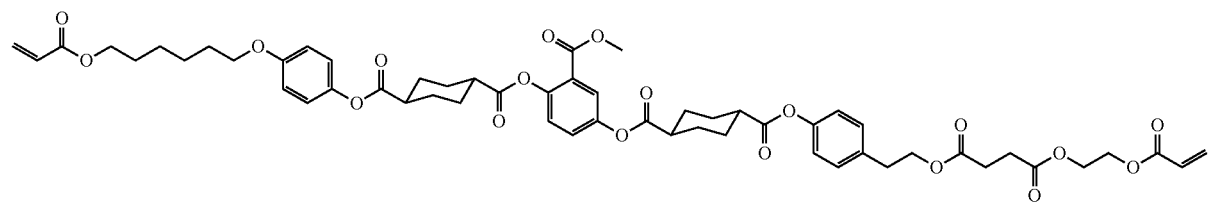
43
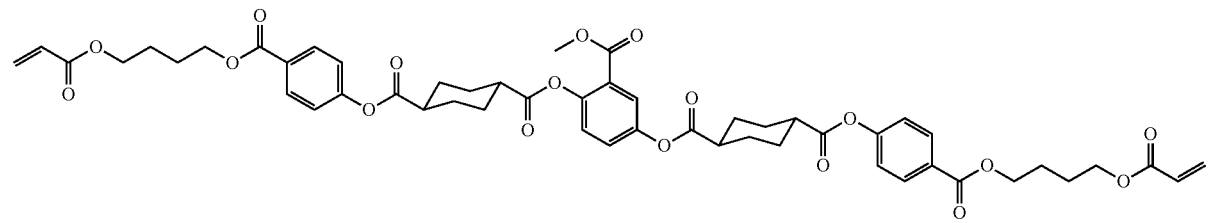
44
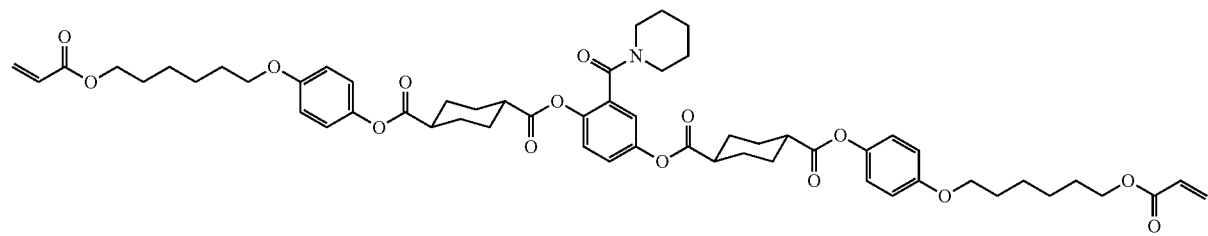
45

-continued
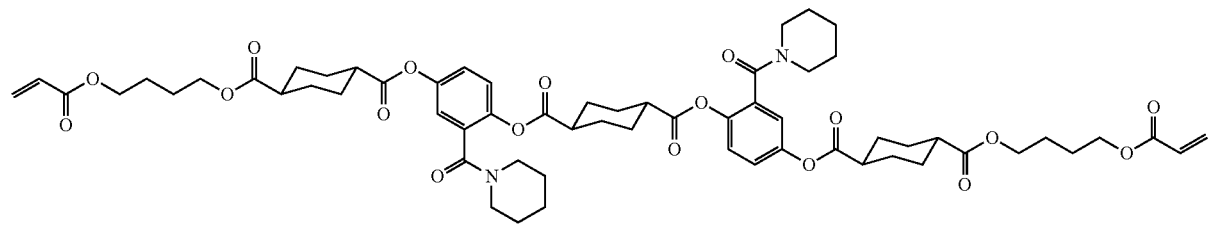
46
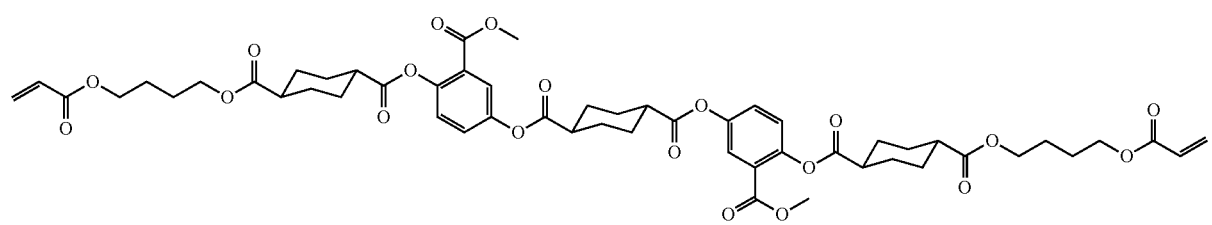
47
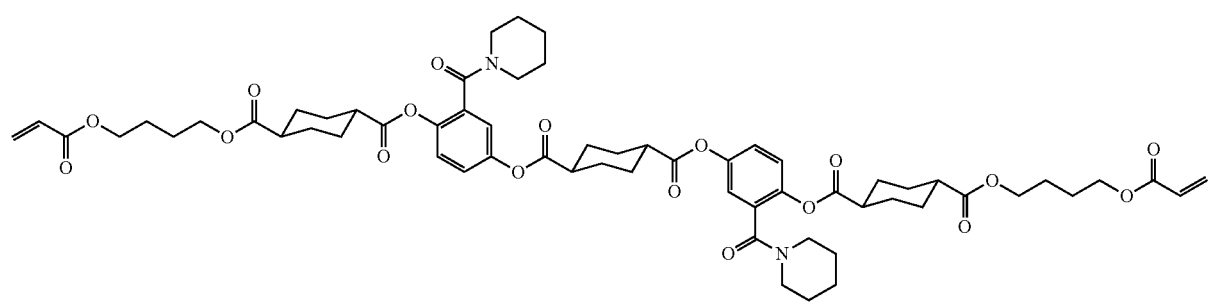
48
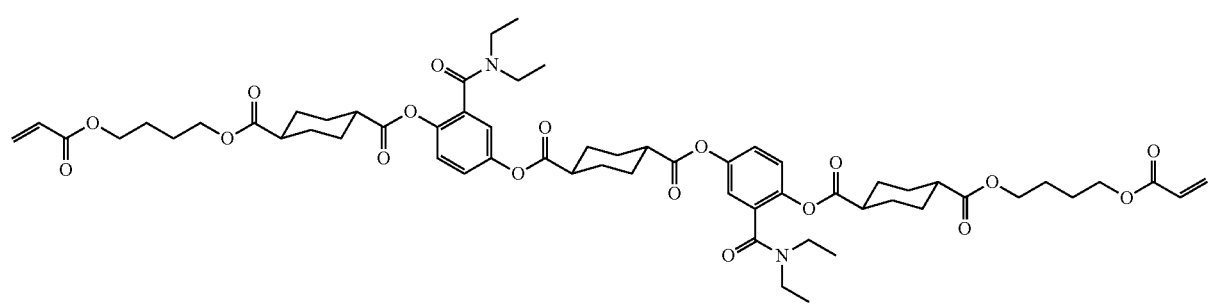
49
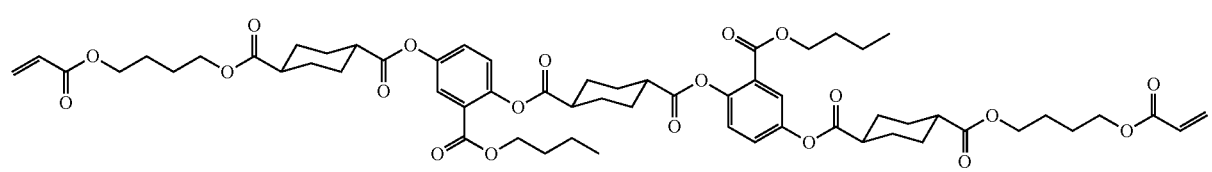
50
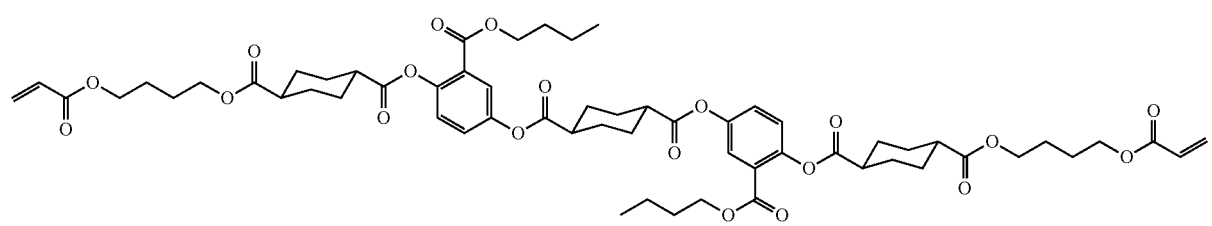
51

52
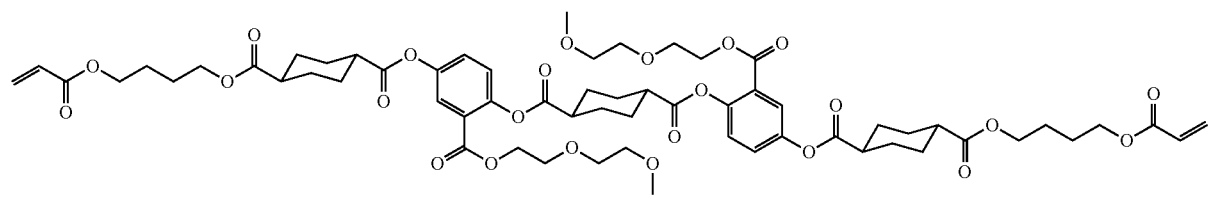
53
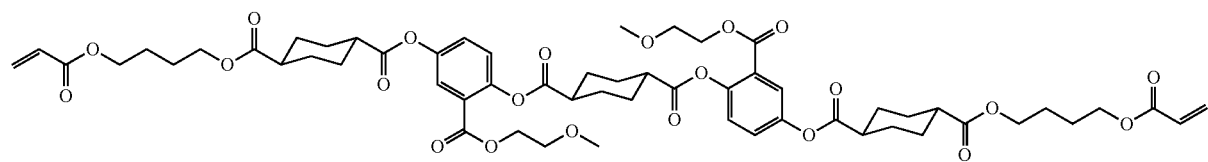
54
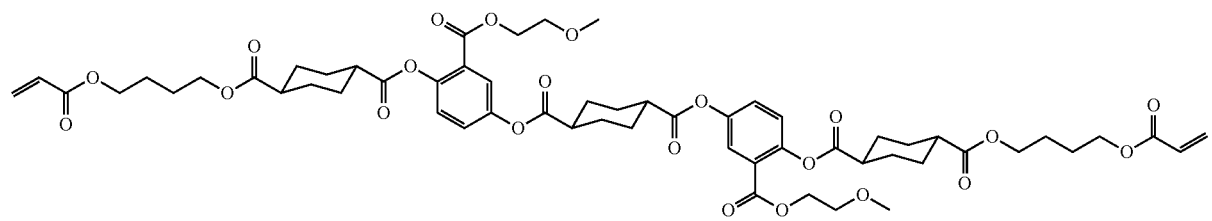
55
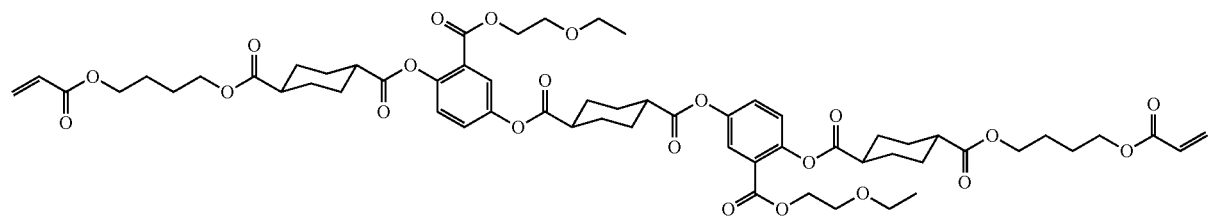
56
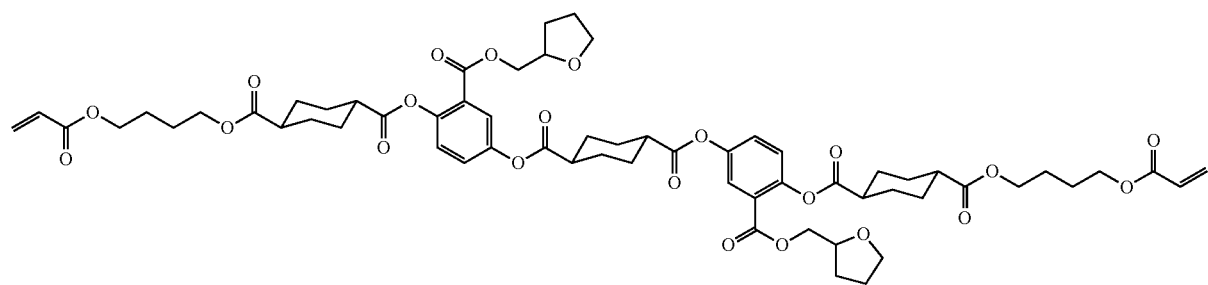
57
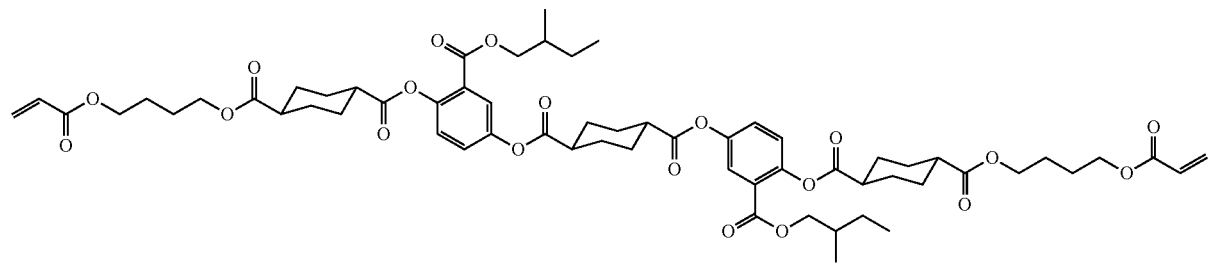

-continued
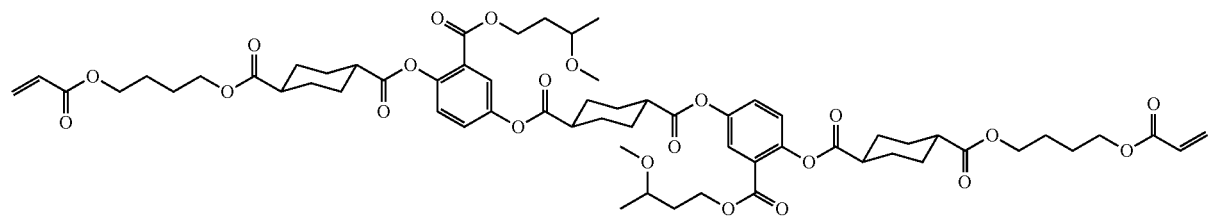
58
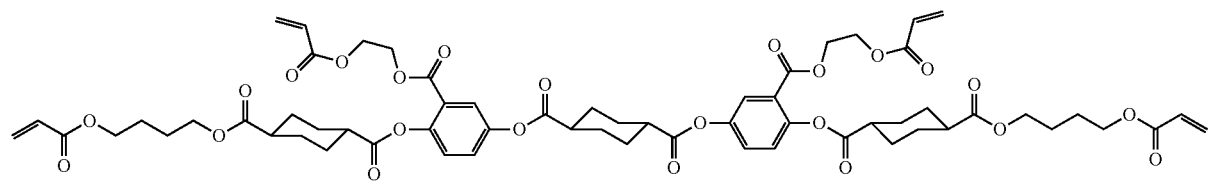
59
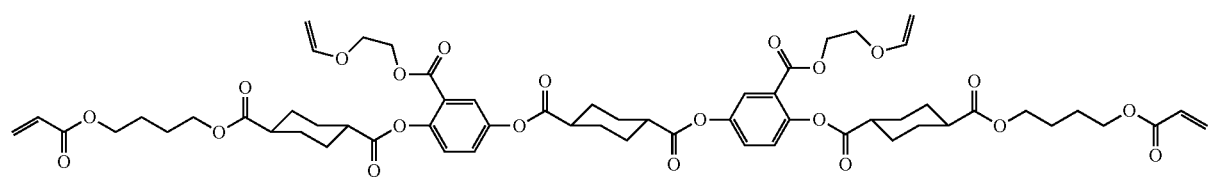
60
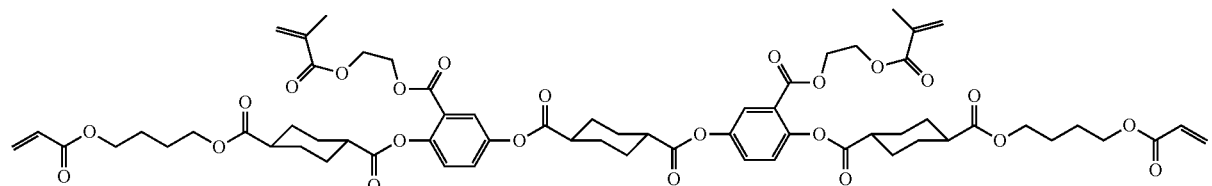
61
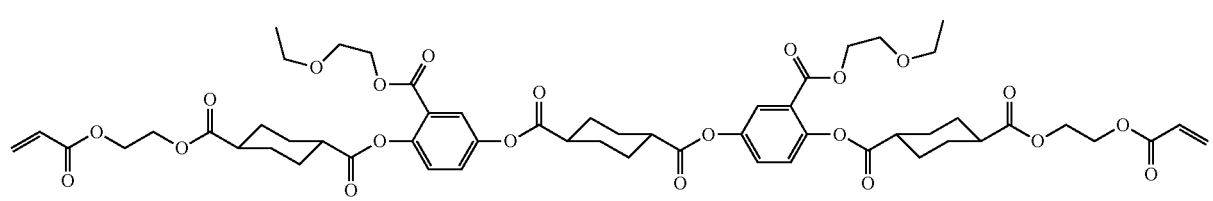
62
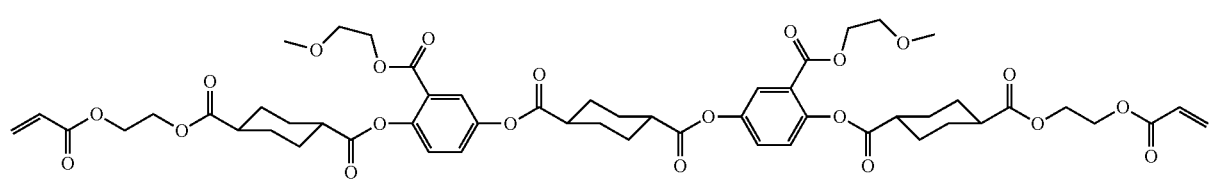
63
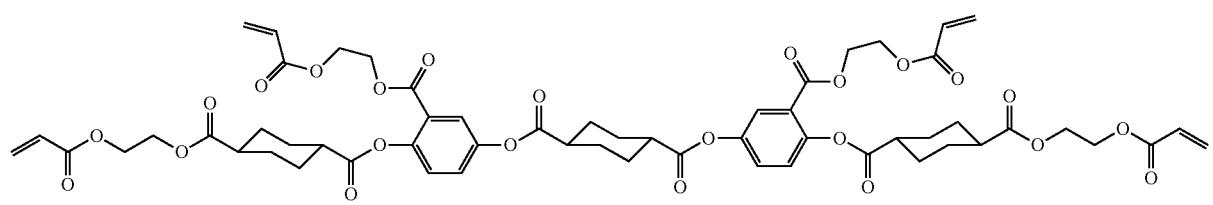
64

-continued
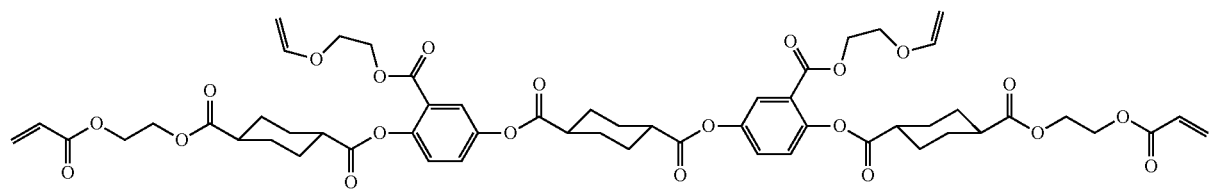
65
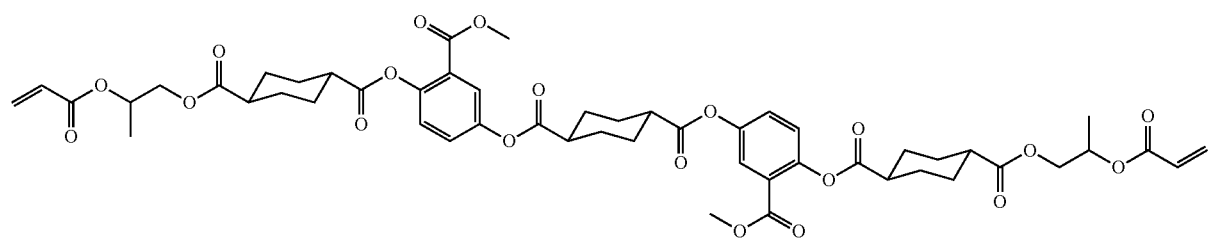
66
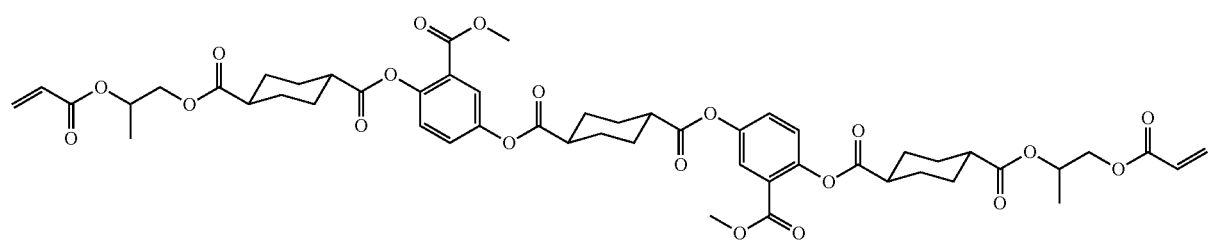
67
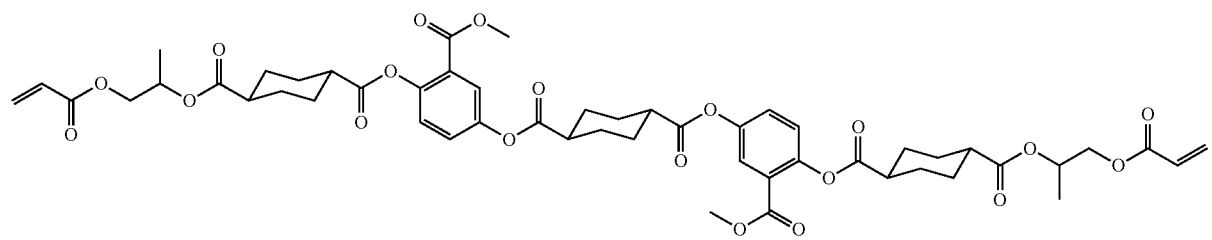
68
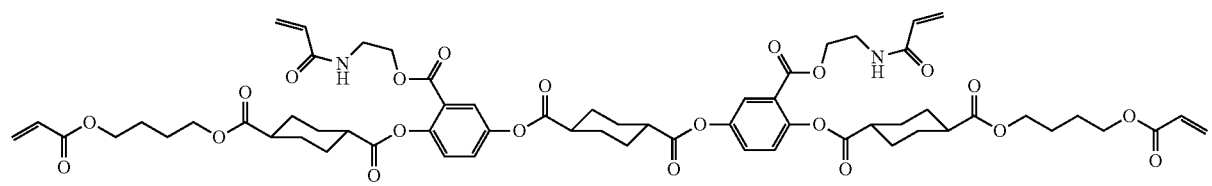
69
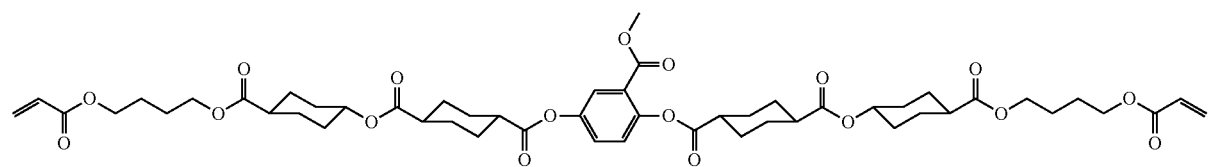
I-1-56
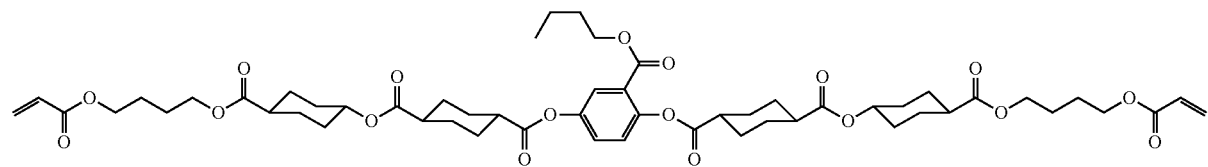
I-1-57

-continued

I-1-58

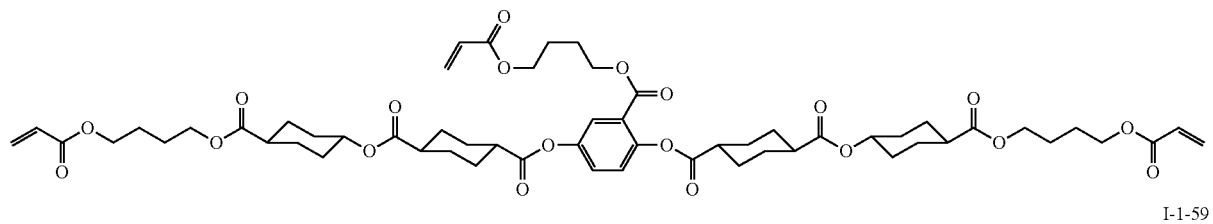

I-1-59

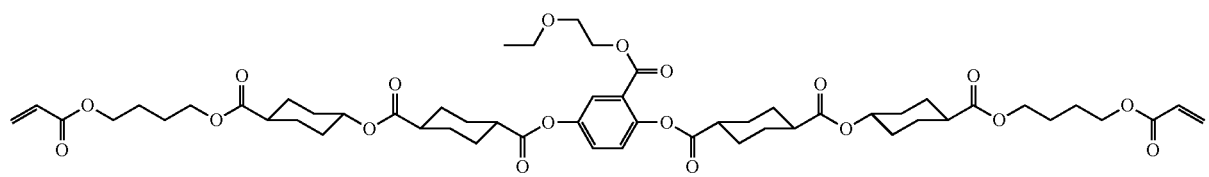

The polymerizable compound denoted by Formula (I) is able to be manufactured by a known method, and for example, the polymerizable compound denoted by Formula (I) is able to be manufactured by the following method.

manufactured by a condensation agent such as carbodiimide, or dehydration condensation due to heating in the presence of an acid catalyst. When LG is a leaving group, A-1 is able to be manufactured by heating A-4 and A-5 in an aprotic

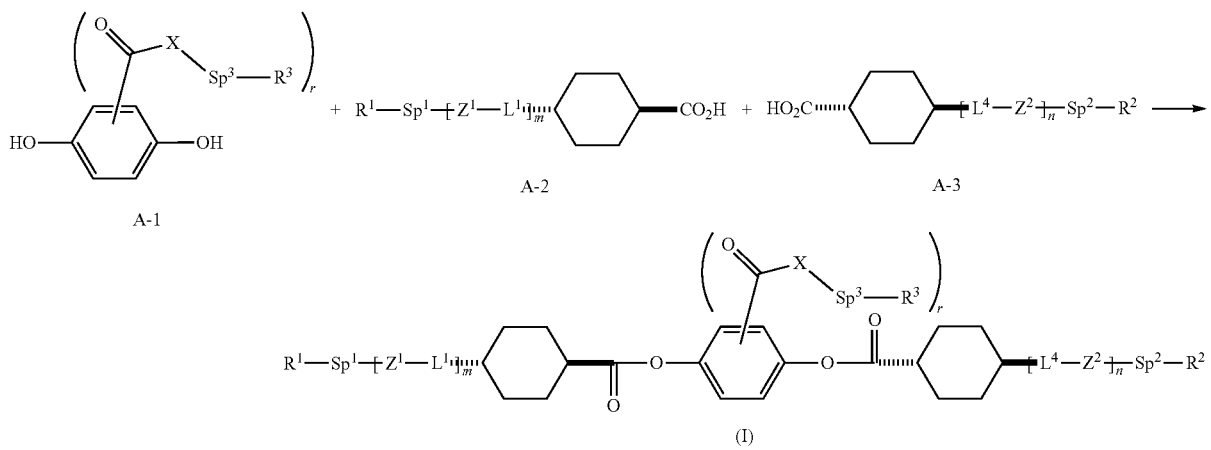

For example, in a case where $L^2$ is —C(=O)O—, and $L^2$ is —OC(=O)—, the polymerizable compound denoted by Formula (I) is able to be manufactured by performing esterification using a phenol (or alcohol) derivative A-1 and a carboxylic acid derivatives A-2 and A-3.

Examples of a method of an esterification reaction include a method in which the carboxylic acid derivatives A-2 and A-3 are subjected to acid chlorination by thionyl chloride, oxalyl chloride, or the like, or mixed acid anhydration is performed by allowing mesyl chloride or the like and a base to act, and then, the phenol (or alcohol) derivative A-1 is allowed to act in the presence of a base. Alternatively, examples of the method include a method in which A-1 and A-2, and A-3 are directly esterified by using a condensation agent such as carbodiimide.

In a case where X is —O—, for example, the phenol (or alcohol) derivative A-1 is able to be manufactured by performing esterification with respect to a carboxylic acid derivative A-4 by using a compound A-5, as a manufacturing method of the phenol (or alcohol) derivative A-1. LG of the compound A-5 represents a hydroxy group or a leaving group. When LG is a hydroxy group, A-1 is able to be polar solvent in the presence of a base. Halogen, a mesyl group, a tosyl group, and the like are able to be used as the leaving group.

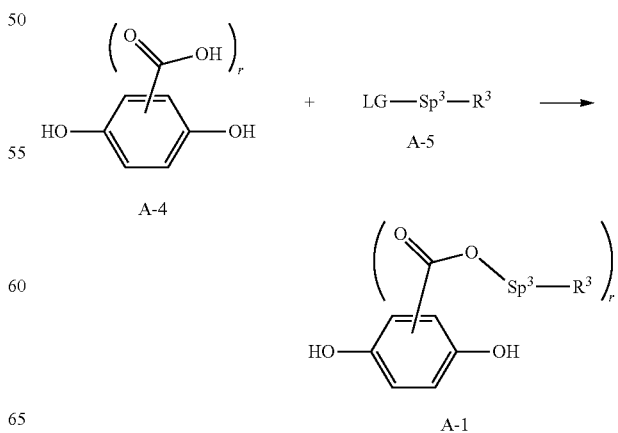

The polymerizable compound denoted by Formula (I) has liquid crystallinity and low birefringence, and thus, the birefringence of the retardation film is able to be adjusted to be in a desired range by preparing the retardation film is prepared using the polymerizable compound denoted by Formula (I). In particular, a cholesteric liquid crystalline phase is formed by using the polymerizable compound denoted by Formula (I), and a film is formed by immobilizing the cholesteric liquid crystalline phase, and thus, a reflection film having a narrow wavelength range of selective reflection, that is, a reflection film having high selectivity in a reflection wavelength range is able to be obtained.

In addition, the polymerizable compound denoted by Formula (I) satisfies a plurality of properties such as being colorless and transparent, having a wide liquid crystalline phase range, being easily dissolved in a solvent, and easily being polymerized, since absorption in a visible light range is extremely low regardless of the type of substituent group of an aromatic ring or a linking group. According to this, a cured film which is prepared by using a polymerizable composition containing the polymerizable compound denoted by Formula (I) is able to satisfy a plurality of properties such as having sufficient hardness, being colorless and transparent, having excellent weather fastness and excellent heat resistance. Accordingly, the cured film formed by using the polymerizable composition described above, for example, is able to be used in various applications such as a retardation plate, a polarization element, a selective reflection film, a color filter, an antireflection film, a view angle compensation film, a holography, and an alignment film which are constituents of an optical element.

<Polymerizable Composition>

In the polymerizable composition, only one type of the polymerizable compound denoted by Formula (I) may be contained, or two or more types thereof may be contained.

The polymerizable compound denoted by Formula (I) (in a case where two or more types of the polymerizable compounds denoted by Formula (I) are contained, the total amount of two or more types of the polymerizable compounds denoted by Formula (I)) may be greater than or equal to 10 mass %, is preferably 30 mass % to 99.9 mass %, is more preferably 50 mass % to 99.5 mass %, and is even more preferably 70 mass % to 99 mass %, with respect to the mass of solid contents of the polymerizable composition. Here, the present invention is not limited to the range described above.

The polymerizable composition may contain other components such as other liquid crystal compounds, a chiral compound, a polymerization initiator, and an alignment control agent, in addition to the polymerizable compound denoted by Formula (I). Hereinafter, each component will be described.

[Other Liquid Crystal Compounds]

The polymerizable composition may contain one or more other liquid crystal compounds along with the polymerizable compound denoted by Formula (I). The polymerizable compound denoted by Formula (I) has high compatibility with the other liquid crystal compounds, and thus, even in a case of being mixed with the other liquid crystal compounds, it is possible to form a film having high transparency without the occurrence of opacification or the like. The other liquid crystal compounds are able to be used together, and thus, it is possible to provide various compositions suitable for various applications since. Examples of the other liquid crystal compounds which are able to be used together include a rod-like nematic liquid crystal compound. Examples of the rod-like nematic liquid crystal compound include azomethines, azoxies, cyanobiphenyls, cyanophenyl esters, benzoic acid esters, cyclohexane carboxylic acid phenyl esters, cyanophenyl cyclohexanes, cyanosubstituted phenyl pyrimidines, alkoxy substituted phenyl pyrimidines, phenyl dioxanes, trans, and alkenyl cyclohexyl benzonitriles. It is possible to use not only a low molecular liquid crystal compound but also a high molecular liquid crystal compound.

The other liquid crystal compounds may be a polymerizable liquid crystal compound or a non-polymerizable liquid crystal compound. A rod-like liquid crystal compound not having a polymerizable group is disclosed in various literatures (for example, Y. Goto et. al., Mol. Cryst. Liq. Cryst. 1995, Vol. 260, pp. 23-28).

A polymerizable rod-like liquid crystal compound is able to be obtained by introducing a polymerizable group into a rod-like liquid crystal compound. Examples of the polymerizable group include an unsaturated polymerizable group, an epoxy group, and an aziridinyl group, and among them, the unsaturated polymerizable group is preferable, and an ethylenically unsaturated polymerizable group is particularly preferable. The polymerizable group is able to be introduced into the molecules of the rod-like liquid crystal compound by various methods. The number of polymerizable groups included in the polymerizable rod-like liquid crystal compound is preferably 1 to 6, and is more preferably 1 to 3. Examples of the polymerizable rod-like liquid crystal compound include compounds disclosed in Makromol. Chem., Vol. 190, p. 2255 (1989), Advanced Materials Vol. 5, p. 107 (1993), the specification of U.S. Pat. No. 4,683,327A, the specification of U.S. Pat. No. 5,622,648A, the specification of U.S. Pat. No. 5,770,107A, WO95/22586A, WO95/24455A, WO97/00600A, WO98/23580A, WO98/52905A, JP1989-272551A (JP-H01-272551A), JP1994-16616A (JP-H06-16616A), JP1995-110469A (JP-H07-110469A), JP1999-80081A (JP-H11-80081A), JP2001-328973A, and the like. Two or more types of polymerizable rod-like liquid crystal compounds may be used together. In a case where two or more types of polymerizable rod-like liquid crystal compounds are used together, it is possible to decrease an alignment temperature.

The added amount of the liquid crystal compounds is not particularly limited, but is preferably 0 mass % to 70 mass %, is more preferably 0 mass % to 50 mass %, and is even more preferably 0 mass % to 30 mass %, with respect to the mass of solid contents of the polymerizable composition. However, the present invention is not limited to the range described above. In the polymerizable composition, the mass ratio of the polymerizable compound denoted by Formula (I) to the other liquid crystal compounds (Mass of Polymerizable Compound denoted by Formula (I)/Mass of Other Liquid Crystal Compounds) may be 100/0 to 30/70, is preferably 100/0 to 50/50, and is more preferably 100/0 to 70/30. The ratio is able to be adjusted to be in a preferred range according to the application.

[Chiral Compound]

The polymerizable composition may contain a chiral compound. By using the chiral compound, it is possible to prepare the polymerizable composition as a composition exhibiting a cholesteric liquid crystalline phase. The chiral compound may be a liquid crystalline chiral compound, or may be a non-liquid crystalline chiral compound. The chiral compound is able to be selected from various known chiral agents (for example, disclosed in Liquid Crystal Device Handbook, Chap. 3, pp. 4-3, Chiral Agent for TN and STN, p. 199, Japan Society for the Promotion of Science, edited by The 142-nd Committee, 1989). In general, the chiral compound has an asymmetric carbon atom, and an axially asymmetric compound or a planarly asymmetric compound which does not has an asymmetric carbon atom is able to be used. Examples of the axially asymmetric compound or the planarly asymmetric compound include binaphthyl, helicene, paracyclophane, and derivatives thereof. The chiral compound (a chiral agent) may have a polymerizable group. In a case where the chiral compound has a polymerizable group, and the rod-like liquid crystal compound to be used together also has a polymerizable group, it is possible to form a polymer having a repeating unit derived from the rod-like liquid crystal compound and a repeating unit derived from the chiral compound by a polymerization reaction between a polymerizable chiral compound and a polymerizable rod-like liquid crystal compound. Therefore, the polymerizable group included in the polymerizable chiral compound is a polymerizable rod-like liquid crystal compound, and is particularly preferably a group identical to the polymerizable group included in the polymerizable compound denoted by Formula (I). Accordingly, the polymerizable group of the chiral compound is preferably an unsaturated polymerizable group, an epoxy group, or an aziridinyl group, is more preferably an unsaturated polymerizable group, and is particularly preferably an ethylenically unsaturated polymerizable group.

In the polymerizable composition, it is preferable that the chiral compound is 1 mol % to 30 mol % with respect to the total number of moles of a liquid crystal compound containing the polymerizable compound denoted by Formula (I). It is preferable that a small amount of chiral compound is used since a small amount of chiral compound does not tend to affect liquid crystallinity. Accordingly, a compound, which has a strong twisting force such that a twisted alignment at a desired spiral pitch is able to be attained even in a case where a small amount of chiral compound is used, is preferable as the chiral compound. Examples of such a chiral agent having a strong twisting force include a chiral agent disclosed in JP2003-287623A. In addition, examples of the chiral agent having a strong twisting force include chiral agents disclosed in JP2002-302487A, JP2002-80478A, JP2002-80851A, and JP2014-034581A, LC-756 manufactured by BASF SE, and the like.

A film formed by setting the polymerizable composition containing the chiral compound to a cholesteric liquid crystalline phase, and by immobilizing the cholesteric liquid crystalline phase has selective reflection properties with respect to light having a predetermined wavelength according to a spiral pitch, and is useful as a reflection film (for example, a visible reflection film or an infrared reflection film). By using the polymerizable compound denoted by Formula (I) which has low birefringence, a reflection wavelength range becomes narrower, and selectivity becomes higher, compared to a film having the same thickness in which a liquid crystal compound having higher birefringence is used.

[Polymerization Initiator]

It is preferable that the polymerizable composition contains a polymerization initiator. For example, in an embodiment where a cured film is formed by performing a curing reaction according to ultraviolet irradiation, it is preferable that a polymerization initiator to be used is a photopolymerization initiator which is able to initiate a polymerization reaction according to ultraviolet irradiation. Examples of the photopolymerization initiator include an α-carbonyl compound (disclosed in the specification of each of U.S. Pat. No. 2,367,661A and U.S. Pat. No. 2,367,670A), acyloin ether (disclosed in the specification of U.S. Pat. No. 2,448,828A), an α-hydrocarbon substituted aromatic acyloin compound (disclosed in the specification of U.S. Pat. No. 2,722,512A), a polynuclear quinone compound (disclosed in the specification of each of U.S. Pat. No. 3,046,127A and U.S. Pat. No. 2,951,758A), a combination between a triaryl imidazole dimer and p-aminophenyl ketone (disclosed in the specification of U.S. Pat. No. 3,549,367A), an acridine compound and a phenazine compound (disclosed in JP1985-105667A (JP-S60-105667A), and in the specification of U.S. Pat. No. 4,239,850A), an oxadiazole compound (disclosed in the specification of U.S. Pat. No. 4,212,970A), and the like.

The photopolymerization initiator contained in the polymerizable composition is preferably 0.1 mass % to 20 mass %, and is more preferably 1 mass % to 8 mass %, with respect to the mass of solid contents of the polymerizable composition.

[Alignment Control Agent]

An alignment control agent which contributes to stable or prompt formation of a liquid crystalline phase (for example, a cholesteric liquid crystalline phase) may be added to the polymerizable composition. Examples of the alignment control agent include a fluorine-containing (meth)acrylate-based polymer, compounds denoted by General Formulas (X1) to (X3) which are disclosed in WO2011/162291A, and a compound disclosed in paragraphs [0020] to [0031] of JP2013-47204A. Two or more types of compounds selected from the compounds described above may be contained. The compounds are able to reduce the tilt angle of the molecules of the liquid crystal compound or to substantially horizontally align the tilt angle in the air interface of the layer. Furthermore, herein, "horizontal alignment" indicates that the major axis of a liquid crystal molecule is parallel to the surface of the film, but does not indicate that the major axis of a liquid crystal molecule is exactly parallel to the surface of the film, and herein, the "horizontal alignment" indicates alignment in which a tilt angle with respect to a horizontal surface is less than 20 degrees. In a case where the liquid crystal compound is horizontally aligned in the vicinity of the air interface, an alignment defect rarely occurs, and thus, transparency in a visible light range increases. In contrast, it is not preferable that the molecules of the liquid crystal compound are aligned at a large tilt angle, for example, the liquid crystal compound is set to a cholesteric liquid crystalline phase since the spiral axis thereof is shifted from a normal direction of the surface of the film, and thus, reflectivity decreases or a fingerprint pattern is generated, and haze increases or diffraction properties are exhibited.

Examples of the fluorine-containing (meth)acrylate-based polymer which is able to be used as an alignment control agent are disclosed in [0018] to [0043] of JP2007-272185A, and the like.

Only one type of compound may be independently used as the alignment control agent, or two or more types of compounds may be used in combination.

The content of the alignment control agent in the polymerizable composition is preferably 0.01 mass % to 10 mass %, is more preferably 0.01 mass % to 5 mass %, and is even more preferably 0.02 mass % to 1 mass %, with respect to the mass of the compound denoted by Formula (I).

[Cross-Linking Agent]

The polymerizable composition may arbitrarily contain a cross-linking agent in order to improve film hardness after being cured and durability. A cross-linking agent which is cured by an ultraviolet ray, heat, humidity, and the like is able to be preferably used as the cross-linking agent.

The cross-linking agent is not particularly limited, but is able to be suitably selected according to the purpose suitably, and examples of the cross-linking agent include a polyfunctional acrylate compound such as trimethylol propane tri(meth)acrylate, pentaerythritol tri(meth)acrylate, and pentaerythritol tetraacrylate; an epoxy compound such as glycidyl (meth)acrylate and ethylene glycol diglycidyl ether; an aziridine compound such as 2,2-bishydroxy methyl butanol-tris[3-(1-aziridinyl) propionate] and 4,4-bis(ethylene iminocarbonyl amino) diphenyl methane; an isocyanate compound such as hexamethylene diisocyanate and biuret type isocyanate; a polyoxazoline compound having an oxazoline group in a side chain; an alkoxy silane compound such as vinyl trimethoxy silane and N-(2-aminoethyl)3-aminopropyl trimethoxy silane, and the like. In addition, a known catalyst is able to be used according to the reactivity of the cross-linking agent, and productivity is able to be improved in addition to the improvement in the film hardness and the durability. Only one type of the compound may be independently used, or two or more types thereof may be used in combination.

The content of the cross-linking agent is preferably 3 mass % to 20 mass %, and is more preferably 5 mass % to 15 mass %, with respect to the mass of solid contents of the polymerizable composition. In a case where the content of the cross-linking agent is greater than or equal to 3 mass %, a cross-linking density improvement effect further increases, and in a case where the content of the cross-linking agent is less than or equal to 20 mass %, the stability of a cholesteric liquid crystal layer becomes higher.

[Other Additives]

The polymerizable composition may contain one type or two or more types of other additives such as an antioxidant, an ultraviolet absorbent, a sensitizing agent, a stabilizer, a plasticizer, a chain transfer agent, a polymerization inhibitor, an antifoaming agent, a leveling agent, a thickener, a flame retardant, a surface-active substance, a dispersant, and a coloring material such as a dye and pigment.

<Film>

The polymerizable compound denoted by Formula (I) is useful as a material of various optical films such as a retardation film and a reflection film, and is able to form various optical films by using the polymerizable composition containing the polymerizable compound denoted by Formula (I).

[Manufacturing Method of Film]

Examples of a manufacturing method of the optical film include a method, including at least:

(i) applying the polymerizable composition containing the polymerizable compound denoted by Formula (I) onto the surface of a substrate or the like, and setting the polymerizable composition to be in a state of a liquid crystalline phase (a cholesteric liquid crystalline phase or the like); and (ii) performing a curing reaction with respect to the polymerizable composition, and forming a cured film by immobilizing the liquid crystalline phase.

The steps of (i) and (ii) are repeated a plurality of times, and thus, it is possible to prepare a film in which a plurality of cured films described above are laminated. In addition, the plurality of cured films are bonded to each other by an adhesive, and thus, it is possible to prepare the film in which the plurality of cured films are laminated.

In the step of (i), first, the polymerizable composition is applied onto the surface of the substrate or the surface of an alignment film formed on the substrate. It is preferable that the polymerizable composition is prepared as a coating liquid in which a material is dissolved and/or dispersed in a solvent. An organic solvent is preferably used as the solvent which is used for preparing the coating liquid. Examples of the organic solvent include amide (for example, N,N-dimethyl formamide); sulfoxide (for example, dimethyl sulfoxide); a heterocyclic compound (for example, pyridine); hydrocarbon (for example, benzene and hexane); alkyl halide (for example, chloroform and dichloromethane); ester (for example, methyl acetate and butyl acetate); ketone (for example, acetone and methyl ethyl ketone); ether (for example, tetrahydrofuran and 1,2-dimethoxy ethane); 1,4-butane diol diacetate, and the like. Among them, the alkyl halide and the ketone are particularly preferable. Two or more types of organic solvents may be used in combination.

The coating liquid is able to be applied by various methods such as a wire bar coating method, an extruding coating method, a direct gravure coating method, a reverse gravure coating method, and a die coating method. In addition, the composition is ejected from a nozzle of an ink jet device, and thus, the coated film is able to be formed.

Next, the polymerizable composition which is applied onto the surface and becomes the coated film is in the state of the liquid crystalline phase such as a cholesteric liquid crystalline phase. In an embodiment where the polymerizable composition is prepared as a coating liquid containing a solvent, there is a case where the coated film is dried, and the solvent is removed, and thus, the polymerizable composition is able to be in the state of the liquid crystalline phase. In addition, in order to set the temperature to be a transition temperature with respect to the liquid crystalline phase, as desired, the coated film may be heated. For example, first, the coated film is heated to the temperature of an isotropic phase, and then, is cooled to the transition temperature of the liquid crystalline phase, and the like, and thus, it is possible to stably set the polymerizable composition to be in the state of the liquid crystalline phase. The transition temperature of the liquid crystalline phase of the polymerizable composition is preferably in a range of 10° C. to 250° C., and is more preferably in a range of 10° C. to 150° C., from the viewpoint of manufacturing suitability or the like. In a case where the transition temperature of the liquid crystalline phase of the polymerizable composition is lower than 10° C., a cooling step or the like is required in order to decreasing the temperature to a temperature range in which the liquid crystalline phase is exhibited. In addition, in a case where the transition temperature of the liquid crystalline phase of the polymerizable composition is higher than 250° C., first, a high temperature is required in order to set the polymerizable composition to be in an isotropic liquid state at a temperature higher than the temperature range in which the liquid crystalline phase is exhibited, and thus, disadvantages are obtained from the viewpoint of the waste of thermal energy, the deformation of the substrate, deterioration, and the like.

Next, in the step of (ii), the coated film which is in the state of the liquid crystalline phase is cured. The curing may be performed by any polymerization method such as a radical polymerization method, an anionic polymerization method, a cationic polymerization method, and a coordination polymerization method. A suitable polymerization method may be selected according to the polymerizable compound denoted by Formula (I). By this polymerization, a polymer having a unit derived from the polymerizable compound denoted by Formula (I) in a constitutional unit is able to be obtained.

In one example, a curing reaction is performed by irradiating the coated film with an ultraviolet ray. In the ultraviolet irradiation, a light source such as an ultraviolet lamp is used. In this step, the curing reaction of the composition is performed by irradiating the coated film with an ultraviolet ray, and thus, the liquid crystalline phase (the cholesteric liquid crystalline phase or the like) is immobilized, and the cured film is formed.

The irradiation energy amount of the ultraviolet ray is not particularly limited, but in general, is preferably approximately 0.1 J/cm$^2$ to 0.8 J/cm$^2$. In addition, a time for irradiating the coated film with the ultraviolet ray is not particularly limited, and may be determined from the viewpoint of both of sufficient hardness and sufficient productivity of the cured film.

In order to accelerate the curing reaction, the ultraviolet irradiation may be performed under heating conditions. In addition, it is preferable that the temperature at the time of performing the ultraviolet irradiation is maintained in a temperature range where the liquid crystalline phase is exhibited such that the liquid crystalline phase is not scattered. In addition, the oxygen concentration in the atmosphere is associated with the degree of polymerization, and thus, in a case where a desired degree of polymerization is not attained in the air, and the film hardness is insufficient, it is preferable that the oxygen concentration in the atmosphere decreases by a method such as nitrogen substitution.

In the step described above, the liquid crystalline phase is immobilized, and the cured film is formed. Here, a state where the alignment of a compound formed of a liquid crystalline phase is retained is the most typical and preferred embodiment as a state where the liquid crystalline phase is "immobilized". The state is not only limited to this, and specifically, indicates a state where a layer does not have fluidity, an alignment configuration is not changed by an external field or an external force, and an immobilized alignment configuration is able to be stably retained in a temperature range of generally 0° C. to 50° C., and of −30° C. to 70° C. in more severe conditions. In the present invention, it is preferable that the curing reaction performed by the ultraviolet irradiation immobilizes the alignment state of the liquid crystalline phase.

Furthermore, in the film, it is sufficient that the optical properties of the liquid crystalline phase are retained in the layer, and finally, it is not necessary that the composition in the cured film has liquid crystallinity in advance. For example, the composition may have a high molecular weight by the curing reaction, and may lose the liquid crystallinity in advance.

The thickness of the cured film described above is not particularly limited. A preferred film thickness may be determined according to the application or according to optical properties to be desired. In general, the thickness is preferably 0.05 µm to 50 µm, and is more preferably 1 µm to 35 µm.

[Substrate]

The film may include a substrate. The material and the optical properties of the substrate are not particularly limited insofar as the substrate has self-supporting properties, and supports the cured film described above. The substrate is able to be selected from a glass plate, a quartz plate, a polymer film, and the like. According to the application, a substrate having high transparency with respect to ultraviolet light may be used. Examples of a polymer film having high transmittance with respect to visible light include polymer films for various optical films which are used as a member of a display device such as a liquid crystal display device. Examples of the substrate include a polyester film of polyethylene terephthalate (PET), polybutylene terephthalate, polyethylene naphthalate (PEN), and the like; a polycarbonate (PC) film, a polymethyl methacrylate film; a polyolefin film of polyethylene, polypropylene, and the like; a polyimide film, a triacetyl cellulose (TAC) film, and the like. The polyethylene terephthalate film and the triacetyl cellulose film are preferable.

[Alignment Layer]

The film may include an alignment layer between the substrate and the cured film. The alignment layer has a function of more accurately defining the alignment direction of the liquid crystal compound. The alignment layer is able to be disposed by means such as a rubbing treatment of an organic compound (preferably a polymer), oblique vapor deposition of an inorganic compound, and formation of a layer having a microgroove. Further, an alignment layer is also known in which an alignment function is generated by applying an electric field, by applying a magnetic field, or by performing light irradiation. It is preferable that the alignment layer is formed by performing a rubbing treatment with respect to the surface of a polymer film.

A polymer of an organic compound is preferable as a material to be used in the alignment layer, a polymer which is able to be cross-linked by itself or a polymer which is cross-linked by a cross-linking agent is preferably used. It is natural that a polymer having both functions is also used. Examples of the polymer are able to include a polymer such as polymethyl methacrylate, an acrylic acid/methacrylic acid copolymer, a styrene/malein imide copolymer, polyvinyl alcohol and modified polyvinyl alcohol, poly(N-methylol acryl amide), a styrene/vinyl toluene copolymer, chlorosulfonated polyethylene, nitrocellulose, polychloride vinyl, chlorinated polyolefin, polyester, polyimide, a vinyl acetate/vinyl chloride copolymer, an ethylene/vinyl acetate copolymer, carboxy methyl cellulose, gelatine, polyethylene, polypropylene, and polycarbonate, and a compound such as a silane coupling agent. Examples of a preferred polymer include a water-soluble polymer such as poly(N-methylol acryl amide), carboxy methyl cellulose, gelatine, polyvinyl alcohol and modified polyvinyl alcohol, and among them, the gelatine, and the polyvinyl alcohol and the modified polyvinyl alcohol are preferable, and the polyvinyl alcohol and the modified polyvinyl alcohol are particularly preferable.

[Adhesive Layer]

In a case where a plurality of cured films are bonded to each other by an adhesive, an adhesive layer is disposed between the cured films. The adhesive layer may be formed of an adhesive.

Examples of the adhesive include a hot melt type adhesive, a thermal curing type adhesive, a photocuring type adhesive, a reaction curing type adhesive, and a pressure sensitive adhesive type adhesive which is not necessary to be cured, from the viewpoint of a curing method, and a compound such as an acrylate-based compound, a urethane-based compound, a urethane acrylate-based compound, an epoxy-based compound, an epoxy acrylate-based compound, a polyolefin-based compound, a modified olefin-based compound, a polypropylene-based compound, an ethylene vinyl alcohol-based compound, a chloride vinyl-based compound, a chloroprene rubber-based compound, a cyanoacrylate-based compound, a polyamide-based compound, a polyimide-based compound, a polystyrene-based compound, and a polyvinyl butyral-based is able to be used as the material of each of the adhesives. The photocuring type adhesive is preferable as a curing method from the viewpoint of workability and productivity, and the acrylate-based compound, the urethane acrylate-based compound, the epoxy acrylate-based compound, and the like are preferably used as the material from the viewpoint of optical transparency and heat resistance.

The film thickness of the adhesive layer is 0.5 µm to 10 µm, and is preferably 1 µm to 5 µm. In a case where the adhesive layer is used as a half mirror for displaying a projection image, it is preferable that the adhesive layer is disposed with an even film thickness in order to reduce color unevenness or the like.

[Application of Film]

One embodiment of the film is a film which is formed by immobilizing the alignment (for example, horizontal alignment, vertical alignment, hybrid alignment, and the like) of a liquid crystalline phase of a polymerizable composition, and has optical anisotropy. The film is used as an optical compensation film or the like of a liquid crystal display device or the like.

One embodiment of the optical film is a film which includes a layer formed by immobilizing a cholesteric liquid crystalline phase of a polymerizable composition, and has selective reflection properties with respect to light in a predetermined wavelength range. In the cholesteric liquid crystalline phase, liquid crystal molecules are arranged into the shape of a spiral. The layer formed by immobilizing the cholesteric liquid crystalline phase (hereinafter, also referred to as a "cholesteric liquid crystal layer") functions as a circularly polarized light selective reflection layer which selectively reflects any one of right circularly polarized light and left circularly polarized light in a selective reflection wavelength range, and transmits the other sense of circularly polarized light. A film including one or two or more cholesteric liquid crystal layers is able to be used in various applications. In a film including two or more cholesteric liquid crystal layers, the senses of circularly polarized light rays which are reflected on the respective cholesteric liquid crystal layers may be identical to each other or opposite to each other according to the application. In addition, the center wavelengths of the selective reflections of the respective cholesteric liquid crystal layer described below may be identical to each other or opposite to each other according to the application.

Furthermore, herein, the "sense" of the circularly polarized light indicates whether the circularly polarized light is right circularly polarized light or left circularly polarized light. In the sense of the circularly polarized light, in a case of observing light such that the light propagates towards the front side thereof, a case where the distal end of an electric field vector is rotated in a clockwise direction according to an increase in time is defined as right circularly polarized light, and a case where the distal end of the electric field vector is rotated in a counterclockwise direction is defined as left circularly polarized light. Herein, the term of "sense" may be used in a twisted direction of a spiral of a cholesteric liquid crystal. In the selective reflection according to the cholesteric liquid crystal, in a case where the twisted direction (the sense) of the spiral of the cholesteric liquid crystal is in a right direction, the right circularly polarized light is reflected, and the left circularly polarized light is transmitted, and in a case where the sense is in a left direction, the left circularly polarized light is reflected, and the right circularly polarized light is transmitted.

For example, a film including a cholesteric liquid crystal layer having selective reflection properties in a visible light wavelength range (a wavelength of 400 nm to 750 nm) is able to be used as a screen or a half mirror for displaying a projection image. In addition, the film is able to be used as a color filter or a filter which improves the color purity of a display light of a display (for example, refer to JP2003-294948A) by controlling a reflection range.

In addition, the optical film is able to be used in various applications such as a polarization element, a reflection film, an antireflection film, a view angle compensation film, a holography, and an alignment film, which are constituents of an optical element.

Hereinafter, an application as a member for displaying a projection image, which is a particularly preferred application, will be described.

[Member for Displaying Projection Image]

In a wavelength at which the projection light is selectively reflected by the function of the cholesteric liquid crystal layer described above, any one sense of the circularly polarized light is reflected, and thus, a projection image is able to be formed. The projection image may be an image which is displayed on the surface of the member for displaying a projection image and viewed in this way, or may be a virtual image emerges from the front of the member for displaying a projection image in a case of being observed by an observer.

A center wavelength $\lambda$ of the selective reflection described above depends on a pitch P (=the cycle of a spiral) of a spiral structure in a cholesteric liquid crystalline phase, and corresponds to a relationship of $\lambda = n \times P$ with an average refractive index n of the cholesteric liquid crystal layer. Furthermore, here, the center wavelength $\lambda$ of the selective reflection in the cholesteric liquid crystal layer indicates a wavelength in a centroid position of a reflection peak of a circularly polarized light reflection spectrum measured from a normal direction of the cholesteric liquid crystal layer. As evident from the expression described above, the pitch of the spiral structure is adjusted, and thus, the center wavelength of the selective reflection is able to be adjusted. That is, an n value and a P value are adjusted, and for example, the center wavelength $\lambda$ is adjusted in order to selectively reflect any one of right circularly polarized light and left circularly polarized light with respect to blue light, and thus, it is possible to set the center wavelength of the selective reflection on appearance to be in a wavelength range of 450 nm to 495 nm. Furthermore, the center wavelength of the selective reflection on appearance indicates the wavelength in the centroid position of the reflection peak of the circularly polarized light reflection spectrum of the cholesteric liquid crystal layer measured from an observation direction at the time of being practically used (at the time of being used as the member for displaying a projection image). The pitch of the cholesteric liquid crystalline phase depends on the type of chiral agent which is used along with the polymerizable liquid crystal compound, or the addition concentration thereof, and thus, a desired pitch is able to be obtained by adjusting the type of chiral agent or the addition concentration thereof. Furthermore, methods disclosed in "Introduction of Liquid Crystal Chemical Experiments" of The Japanese Liquid Crystal Society, published by Sigma Publishing Company in 2007, p. 46, and "Liquid Crystal Handbook" of Editorial Committee of Liquid Crystal Handbook, published by MARUZEN-YUSHODO Company, Limited, p. 196 are able to be used as a measurement method of the sense of the spiral or the pitch.

A half-width $\Delta\lambda$ (nm) of the selective reflection wavelength range where circularly polarized light selective reflection is exhibited depends on birefringence $\Delta n$ of the liquid crystal compound and the pitch P described above, and corresponds to a relationship of $\Delta\lambda = \Delta n \times P$. For this reason, the width of the selective reflection wavelength range is able to be controlled by adjusting $\Delta n$. That is, in the cholesteric liquid crystal layer formed of the composition containing the polymerizable liquid crystal compound having low birefringence of the present invention, it is possible to increase the wavelength selectivity of the selective reflection.

For example, $\Delta\lambda/\lambda$, which is a ratio of the half-width $\Delta\lambda$ of the selective reflection wavelength range to the center wavelength $\lambda$ of the selective reflection, is able to be used as an index indicating the wavelength selectivity of the selective reflection. In the film of the present invention, in particular, in the film which is used as the member for displaying a projection image, $\Delta\lambda/\lambda$ is preferably less than or equal to 0.09, and is more preferably less than or equal to 0.07. More specifically, in the cholesteric liquid crystal layer of the film, it is preferable that $\Delta\lambda/\lambda$ satisfies the range described above, and in each of the two or more cholesteric liquid crystal layers of the film including two or more cholesteric liquid crystal layers, it is preferable that $\Delta\lambda/\lambda$ satisfies the range described above. Furthermore, $\Delta\lambda$'s and $\lambda$'s of the respective layers may be identical to each other or different from each other.

Each cured film having a center wavelength of selective reflection on appearance in each of a red light wavelength range, a green light wavelength range, and a blue light wavelength range is prepared by using the polymerizable composition described above, and the cured films are laminated, and thus, a member for displaying a projection image which is able to display a full color projection image is able to be prepared. Specifically, in a half mirror, it is preferable that cured films having different center wavelengths of selective reflections (for example, different by greater than or equal to 50 nm) in each of ranges of 750 nm to 620 nm, 630 nm to 500 nm, and 530 nm to 420 nm are laminated.

The center wavelength of the selective reflection of each of the cured films is adjusted according to a light emission wavelength range of a light source to be used in projection and a use embodiment of the member for displaying a projection image, and thus, a clear projection image with excellent light utilization efficiency is able to be displayed. In particular, each of the center wavelengths of the selective reflections of the cured films is adjusted according to the light emission wavelength range of the light source to be used in the projection, and the like, and thus, a clear color projection image with excellent light utilization efficiency is able to be displayed. In particular, examples of the use embodiment of the member for displaying a projection image include an incidence angle of projection light on the surface of the half mirror for displaying a projection image, a projection image observation direction on the surface of the member for displaying a projection image surface, and the like.

For example, the member for displaying a projection image described above is configured to have transmittance with respect to light in a visible light range, and thus, is able to be used as a half mirror which is able to be used as a combiner of a head-up display. The half mirror for displaying a projection image is able to visibly display an image projected from a projector or the like and to simultaneously information and scenery on an opposite surface side at the time of observing the half mirror for displaying a projection image from the same surface side as the surface on which the image is displayed.

When the member for displaying a projection image is used as the half mirror for displaying a projection image, it is preferable that the cured film prepared as described above, in particular, a laminate of three or more cured films is disposed on the surface of a substrate surface. It is preferable that the substrate is transparent and has low birefringence in a visible light range. For example, the retardation of the substrate at a wavelength of 550 nm is preferably less than or equal to 50 nm, and is more preferably less than or equal to 20 nm.

Examples of the substrate include inorganic glass or a polymer resin (an acrylic resin (acrylic acid esters such as polymethyl (meth)acrylate, and the like), cyclic polyolefin such as polycarbonate, cyclopentadiene-based polyolefin, or norbornene-based polyolefin, polyolefins such as polypropylene, aromatic vinyl polymers such as polystyrene, polyarylate, cellulose acylate, and the like).

The half mirror for displaying a projection image may include an antireflection layer. It is preferable that the antireflection layer is provided on the outermost surface. The antireflection layer may be disposed on the outermost surface which becomes an observation side at the time of using the half mirror for displaying a projection image, or may be disposed on the outermost surface on a side opposite to the observation side, and it is preferable that the antireflection layer is disposed on the outermost surface on the observation side. In a case where the cured film is disposed on the surface of the substrate, the antireflection layer may be disposed on both of a substrate side surface and a cured film side which becomes the observation side. According to such a configuration, a double image, which is particularly generated in a case where the birefringence of the substrate is high, is rarely generated.

Examples of the antireflection layer include a film having a configuration of a two-layer film in which a layer of high refractive index and a layer of low refractive index are combined, a film having a configuration of a three-layer film in which a layer of intermediate refractive index, a layer of high refractive index, and a layer of low refractive index are laminated in this order, and the like, in addition to a film in which fine surface concavities and convexities are formed.

Configuration examples include a configuration including two layers of a layer of high refractive index/a layer of low refractive index in this order from a lower side, a configuration including three layers having different refractive indices, in which a layer of intermediate refractive index (a layer having a refractive index which is higher than that of a underlayer and is lower than that of a layer of high refractive index)/a layer of high refractive index/a layer of low refractive index are laminated in this order, and the like, and it is also proposed that more antireflection layers are laminated. Among them, it is preferable that a layer of intermediate refractive index/a layer of high refractive index/a layer of low refractive index are provided on a hard coat layer in this order, from the viewpoint of durability, optical properties, costs, productivity, and the like, and examples of configuration include configurations disclosed in JP1996-122504A (JP-H08-122504A), JP1996-110401A (JP-H08-110401A), JP1998-300902A (JP-H10-300902A), JP2002-243906A, JP2000-111706A, and the like. In addition, an antireflection film having a three-layer configuration, which has excellent robustness with respect to a variation in a film thickness, is disclosed in JP2008-262187A. In a case where the antireflection film having a three-layer configuration described above is disposed on the surface of an image display device, the average of reflectivity is able to be less than or equal to 0.5%, is able to considerably reduce reflected glare, and is able to obtain an image having excellent stereoscopic effects. In addition, other functions may be imparted to each layer, and examples of a layer to which other functions are imparted include a layer of low refractive index having antifouling properties, a layer of high refractive index having antistatic properties, a hard coat layer having antistatic properties, and a hard coat layer having anti-glare characteristics (for example, JP1998-206603A (JP-H10-206603A), JP2002-243906A, JP2007-264113A, and the like), and the like.

Examples of an inorganic material configuring the antireflection layer include $SiO_2$, $SiO$, $ZrO_2$, $TiO_2$, $TiO$, $Ti_2O_3$, $Ti_2O_5$, $Al_2O_3$, $Ta_2O_5$, $CeO_2$, $MgO$, $Y_2O_3$, $SnO_2$, $MgF_2$, $WO_3$, and the like, and only one type of material is able to be independently used, or two or more types thereof are able to be used in combination. Among them, $SiO_2$, $ZrO_2$, $TiO_2$, and $Ta_2O_5$ are preferable since vacuum vapor deposition is able to be performed at a low temperature, and thus, a film is also able to be formed on the surface of a plastic substrate.

A laminated structure of alternately forming a high refractive index material layer and a low refractive index material layer, in which the total optical film thickness of a $ZrO_2$ layer and a $SiO_2$ layer from the substrate side is $\lambda/4$, the optical film thickness of the $ZrO_2$ layer is $\lambda/4$, and the optical film thickness of the $SiO_2$ layer of an outermost layer is $\lambda/4$, is exemplified as a multilayer film which is formed of the inorganic material. Here, $\lambda$ is a design wavelength, and a wavelength of 520 nm is generally used. It is preferable that the outermost layer is formed of $SiO_2$ since a refractive index is low, and mechanical hardness is able to be imparted to the antireflection layer.

In a case where the antireflection layer is formed of the inorganic material, for example, a vacuum vapor deposition method, an ion plating method, a sputtering method, a CVD method, a method of performing precipitation in a saturated solution by a chemical reaction, and the like are able to be adopted as a film formation method.

Examples of an organic material which is used in the layer of low refractive index are able to include a tetrafluoroethylene-hexafluoropropylene copolymer (FFP), polytetrafluoroethylene (PTFE), an ethylene-tetrafluoroethylene copolymer (ETFE), and the like, and a composition containing a fluorine-containing curable resin and inorganic fine particles, which is disclosed in JP2007-298974A, a low refractive index coating composition containing hollow silica fine particles, which is disclosed in JP2002-317152A, JP2003-202406A, and JP2003-292831A are able to be preferably used. The film formation method is able to be performed by coating methods such as a spin coating method, a dip coating method, and a gravure coating method, which have excellent productivity, in addition to the vacuum vapor deposition method.

The refractive index of the layer of low refractive index is preferably 1.30 to 1.51. The refractive index of the layer of low refractive index is more preferably 1.30 to 1.46, and is even more preferably 1.32 to 1.38.

Examples of an organic material which is used in the layer of intermediate refractive index and the layer of high refractive index are able to include a binder which is obtained by cross-linking or a polymerization reaction, such as an ionizing radiation curable compound having an aromatic ring, an ionizing radiation curable compound containing a halogenated element (for example, Br, I, Cl, and the like) other than fluorine, and an ionizing radiation curable compound containing an atom such as S, N, and P, and inorganic particles containing $TiO_2$ to be added to the binder as a main component. Specifically, an organic material disclosed in paragraphs [0074] to [0094] of JP2008-262187A is able to be exemplified.

The refractive index of the layer of high refractive index is preferably 1.65 to 2.20, and is more preferably 1.70 to 1.80. The refractive index of the layer of intermediate refractive index is adjusted to be a value between the refractive index of the layer of low refractive index and the refractive index of the layer of high refractive index. The refractive index of the layer of intermediate refractive index is preferably 1.55 to 1.65, and is more preferably 1.58 to 1.63.

The film thickness of the antireflection layer is not particularly limited, but may be approximately 0.1 μm to 10 μm, 1 μm to 5 μm, and 2 μm to 4 μm.

EXAMPLES

Hereinafter, the characteristics of the present invention will be described in detail with reference to the examples and comparative examples. Materials, use amounts, ratios, treatment contents, treatment sequences, and the like of the following examples are able to be suitably changed unless the changes cause deviance from the gist of the present invention. Accordingly, the range of the present invention will not be restrictively interpreted by the following specific examples.

<Synthesis of Compound I-1>

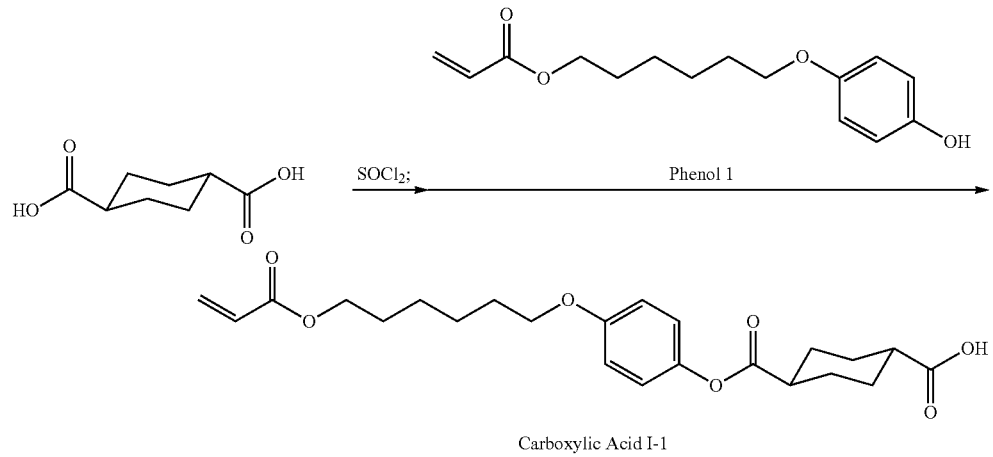

Carboxylic Acid I-1

A trans-1,4-cyclohexadicarboxylic acid (21 g) and thionyl chloride (29 g) were stirred in toluene (60 mL) at an internal temperature of 70° C. for 2 hours. The solvent was distilled under reduced pressure, and then, tetrahydrofuran (THF) (50 mL), phenol 1 (31.21 g), and dibutyl hydroxy toluene (BHT) (0.2 g) were added, a THF (15 mL) solution of N,N-dimethyl aminopyridine (0.8 g) and N,N-diisopropyl ethyl amine (16.17 g) was dropped, and the mixture was stirred at room temperature for 3 hours. Methanol (2 mL) was added, and the mixture was stirred at room temperature for 15 minutes, and then, water and ethyl acetate were added, a water layer was removed, and organic layer was washed with a dilute hydrochloric acid and saline in this order. The organic layer was dried with magnesium sulfate, the desiccant was filtered, and then, the solvent was distilled under reduced pressure, and purification was performed by a column chromatography (Hexane:Ethyl Acetate=4:1), and thus, a carboxylic acid I-1 was obtained.

$^1$H-NMR(Solvent: CDCl$_3$)δ(ppm):
1.4-1.7 (m, 7H), 1.7-1.9 (m, 5H), 2.1-2.3 (m, 4H), 2.3-2.4 (m, 1H), 2.5-2.6 (m, 1H), 3.9 (t, 2H), 4.2 (t, 2H), 5.8 (dd, 1H), 6.1 (dd, 1H), 6.4 (dd, 1H), 6.9 (d, 2H), 7.0 (d, 2H)

<Synthesis of Compound 20>

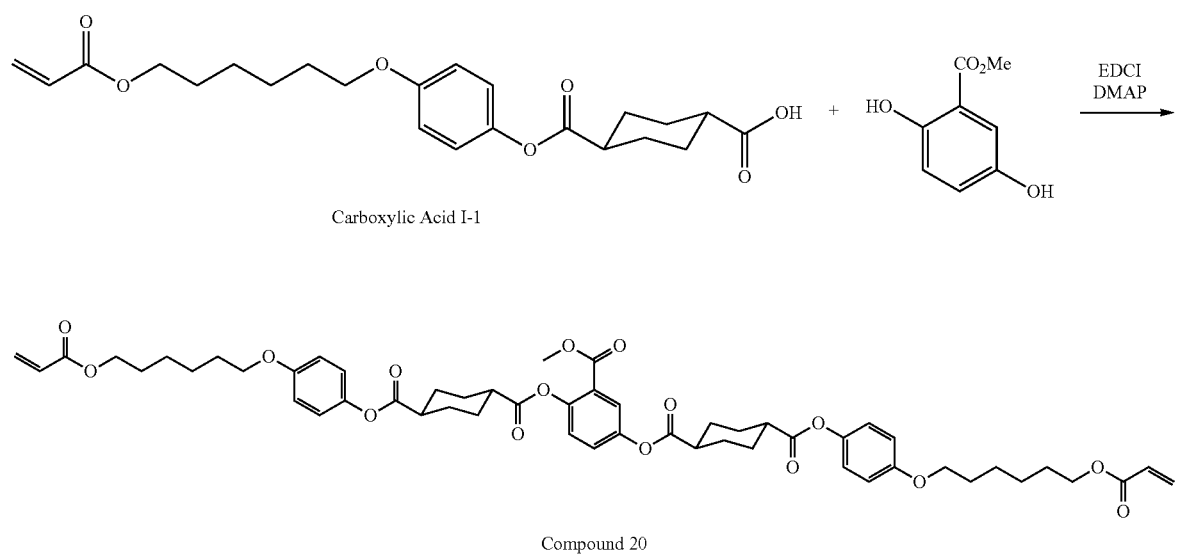 [SMILES: C=CC(=O)OCCCCCCOc1ccc(OC(=O)C2CCC(C(=O)O)CC2)cc1 ; COC(=O)c1cc(O)ccc1O ; C=CC(=O)OCCCCCCOc1ccc(OC(=O)C2CCC(C(=O)Oc3ccc(OC(=O)C4CCC(C(=O)Oc5ccc(OCCCCCCOC(=O)C=C)cc5)CC4)c(C(=O)OC)c3)CC2)cc1]

Carboxylic Acid I-1

Compound 20

A carboxylic acid I-1 (500 mg), 2-(methoxy carbonyl) hydroquinone (100 mg), N,N-dimethyl aminopyridine (7.3 mg), and BHT (6.6 mg) were stirred in a mixed solvent of dimethyl acetoamide (DMAc) (2 mL) and THF (1 mL), 3-[(ethyl carbon imidoyl) amino]-N,N-dimethyl-1-propane amine hydrochloride (252 mg) was added, and the mixture was stirred for 3 hours. Water and ethyl acetate were added, a water layer was removed, and an organic layer was washed with a dilute hydrochloric acid. The organic layer was dried with magnesium sulfate, the desiccant was filtered, and then, BHT (0.1 g) was added, the solvent was distilled under reduced pressure, methanol (10 mL) was added, cooling was performed until the internal temperature became 0° C., and the generated crystal was filtered, and thus, a compound 20 (420 mg) was obtained.

$^1$H-NMR(Solvent: CDCl$_3$)δ(ppm):
1.4-1.6 (m, 8H), 1.6-1.9 (m, 16H), 2.2-2.4 (m, 8H), 2.5-2.7 (m, 4H), 3.86 (s, 3H), 3.94 (t, 4H), 4.2 (t, 4H), 5.8 (dd, 2H), 6.1 (dd, 2H), 6.4 (dd, 2H), 6.9 (d, 4H), 7.0 (d, 4H), 7.1 (d, 1H), 7.3 (dd, 1H), 7.7 (d, 1H)

<Synthesis of Compound I-2>

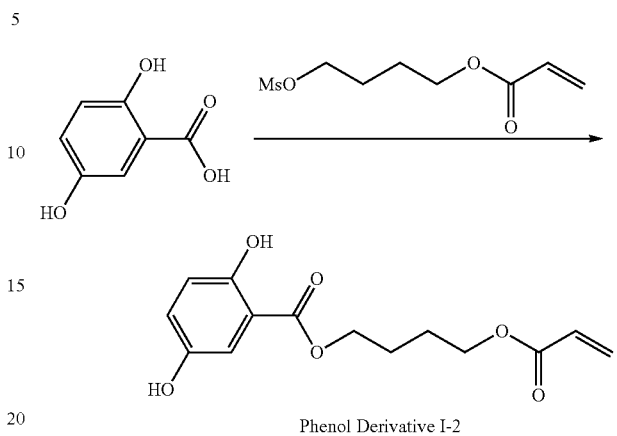

Phenol Derivative I-2

A 2,5-dihydroxy benzoic acid (10 g) was stirred in dimethyl acetoamide (50 mL), triethyl amine (9.8 mL), methane sulfonate 4-acryloyl oxy butyl (11.1 g), and BHT (0.2 g) were added, and the mixture was stirred at an internal temperature of 70° C. for 10 hours. The mixture was cooled to 30° C., and then, water and ethyl acetate were added, a water layer was removed, and an organic layer was washed with a saturated sodium bicarbonate aqueous solution, a dilute hydrochloric acid, and saline in this order. The organic layer was dried with magnesium sulfate, the desiccant was filtered, and then, BHT (0.1 g) was added, the solvent was distilled under reduced pressure, and thus, a phenol derivative I-2 was obtained.

<Synthesis of Compound 28>

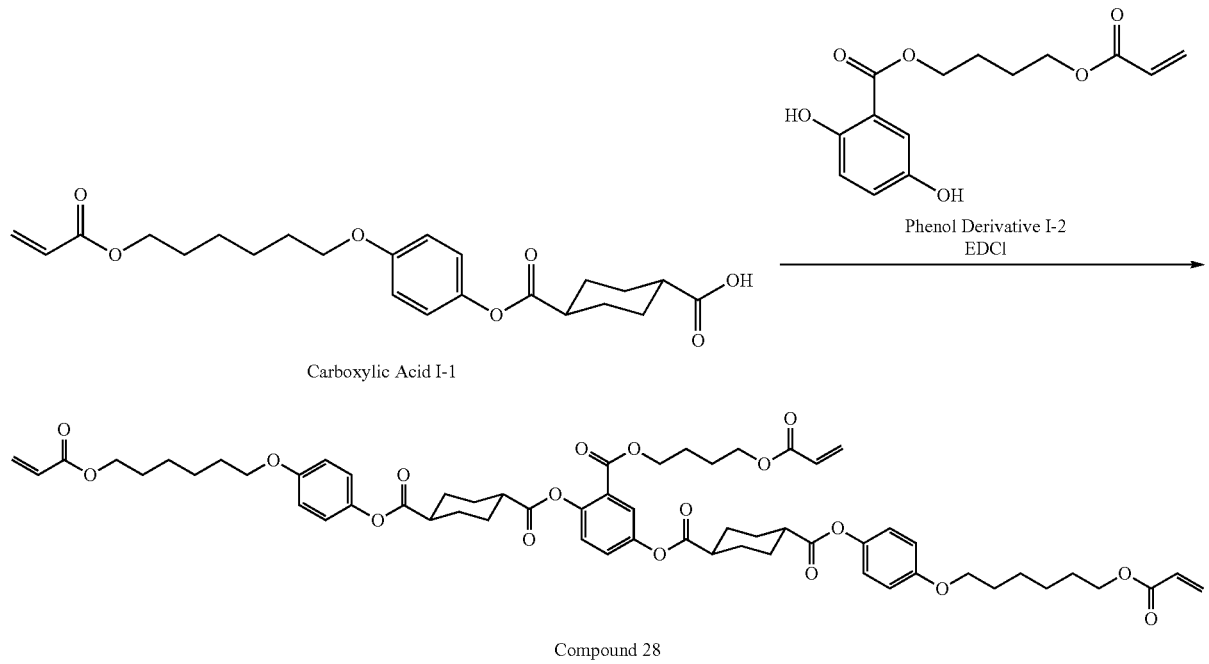

Compound 28

A carboxylic acid I-1 (500 mg), a phenol derivative I-2 (167 mg), N,N-dimethyl aminopyridine (7.3 mg), and BHT (6.6 mg) were stirred in a mixed solvent of DMAc (2 mL) and THF (1 mL), 3-[(ethyl carbon imidoyl) amino]-N,N-dimethyl-1-propane amine hydrochloride (252 mg) was added, and the mixture was stirred for 5 hours. Water and ethyl acetate were added, a water layer was removed, and an organic layer was washed with a dilute hydrochloric acid. The organic layer was dried with magnesium sulfate, the desiccant was filtered, BHT (0.1 g) was added, the solvent was distilled under reduced pressure, methanol (10 mL) was added, cooling was performed until the internal temperature became 0° C., and the generated crystal was filtered, and thus, a compound 28 (603 mg) was obtained.

$^1$H-NMR(Solvent: $CDCl_3$)δ(ppm):
1.4-1.9 (m, 28H), 2.2-2.4 (m, 8H), 2.5-2.7 (m, 4H), 3.9 (t, 4H), 4.18 (t, 4H), 4.22 (t, 2H), 4.3 (t, 2H), 5.8-5.9 (m, 3H), 6.1-6.2 (m, 3H), 6.4-6.5 (m, 3H), 6.9 (d, 4H), 7.0 (d, 4H), 7.1 (d, 1H), 7.3 (dd, 1H), 7.7 (dd, 1H)

<Synthesis of Compound I-3>

Succinic acid mono(2-acryloyl oxy ethyl) (10 g) was stirred in a mixed solution of ethyl acetate (32 mL) and dimethyl acetoamide (8 mL), and BHT (0.2 g) was added. The reaction liquid was cooled until the internal temperature became 0° C., a solution of ethyl acetate (10 mL) of thionyl chloride (3.3 mL) was dropped, and the mixture was stirred at 0° C. for 30 minutes. After that, 2-(4-hydroxy phenyl) ethanol (5.3 g) and pyridine (3.7 mL) were added at an internal temperature of 0° C., and the mixture was stirred at room temperature for 2 hours. Water and ethyl acetate were added, a water layer was removed, and an organic layer was washed with a dilute hydrochloric acid, a saturated sodium bicarbonate aqueous solution, and saline in this order. The organic layer was dried with magnesium sulfate, the desiccant was filtered, and then, BHT (0.1 g) was added, and the solvent was distilled under reduced pressure. After that, purification was performed by a column chromatography (Hexane:Ethyl Acetate=6:4), and thus, a phenol derivative I-3 (9.63 g) was obtained.

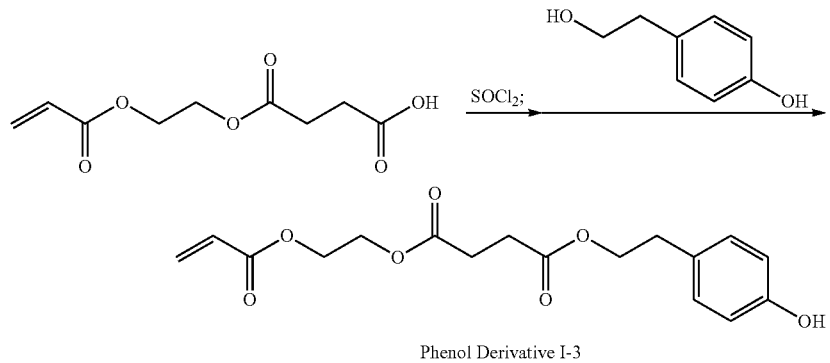

Phenol Derivative I-3

¹H-NMR(Solvent: CDCl₃)δ(ppm):
2.6-2.7 (m, 4H), 2.8 (t, 2H), 4.2 (t, 2H), 4.3-4.4 (m, 4H), 5.6 (brs, 1H), 5.9 (dd, 1H), 6.1 (dd, 1H), 6.4 (dd, 1H), 5.8 (d, 2H), 7.1 (d, 2H)

<Synthesis of Compound I-4>

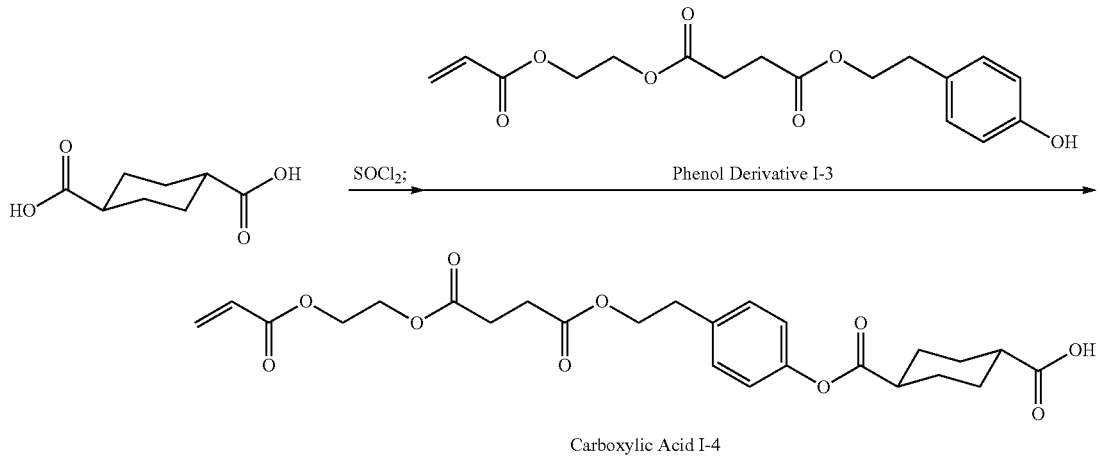

Carboxylic Acid I-4

A trans-1,4-cyclohexadicarboxylic acid (4.4 g) and thionyl chloride (6.1 g) were stirred in toluene (15 mL) at an internal temperature of 70° C. for 2 hours. The solvent was distilled under reduced pressure, and then, THF (30 mL), a phenol derivative I-3 (8.38 g), and BHT (0.3 g) were added, THF (10 mL) solution of N,N-dimethyl aminopyridine (0.3 g) and N,N-diisopropyl ethyl amine (4.5 mL) was dropped, and the mixture was stirred at room temperature for 3 hours. Methanol (2 mL) was added, the mixture was stirred at room temperature for 15 minutes, and then, water and ethyl acetate were added, a water layer was removed, and an organic layer was washed with a dilute hydrochloric acid and saline in this order. The organic layer was dried with magnesium sulfate, the desiccant was filtered, and then, the solvent was distilled under reduced pressure, purification was performed by a column chromatography (Hexane:Ethyl Acetate=2:1), and thus, a carboxylic acid I-4 was obtained.

¹H-NMR(Solvent: CDCl₃)δ(ppm):
1.5-1.7 (m, 4H), 2.1-2.3 (m, 4H), 2.3-2.5 (m, 1H), 2.5-2.7 (m, 5H), 2.9 (t, 2H), 4.2-4.4 (m, 6H), 5.9 (dd, 1H), 6.1 (dd, 1H), 6.4 (dd, 1H), 7.0 (d, 2H), 7.2 (d, 2H)

<Synthesis of Compound 16>

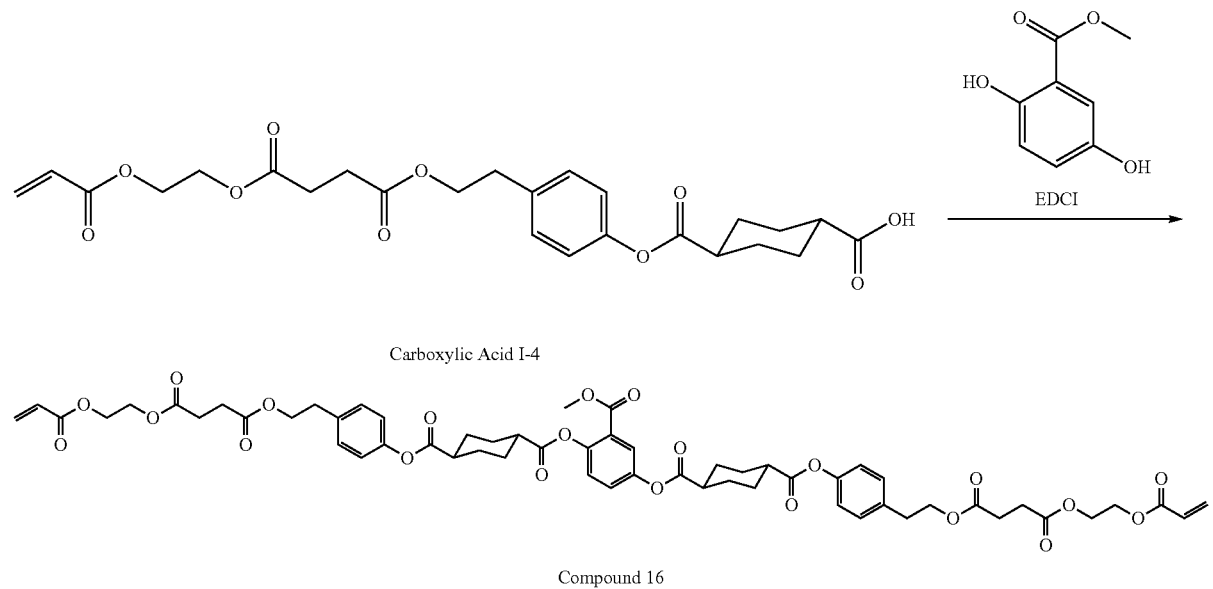

Compound 16

A carboxylic acid I-4 (700 mg), 2-(methoxy carbonyl) hydroquinone (115 mg), N,N-dimethyl aminopyridine (8.3 mg), and BHT (7.5 mg) were stirred in dichloromethane (3 mL), 3-[(ethyl carbon imidoyl) amino]-N,N-dimethyl-1-propane amine hydrochloride (391 mg) was added, and the mixture was stirred for 5 hours. Water was added, a water layer was removed, and an organic layer was washed with a dilute hydrochloric acid. The organic layer was dried with magnesium sulfate, the desiccant was filtered, and then, BHT (0.1 g) was added, the solvent was distilled under reduced pressure, methanol (10 mL) was added, cooling was performed until the internal temperature became 0° C., and the generated crystal was filtered, and thus, a compound 16 (620 mg) was obtained.

$^1$H-NMR(Solvent: CDCl$_3$)δ(ppm):

1.6-1.8 (m, 8H), 2.2-2.4 (m, 8H), 2.5-2.7 (m, 12H), 2.9 (t, 4H), 3.9 (s, 3H), 4.2-4.4 (m, 12H), 5.9 (dd, 1H), 6.1 (dd, 1H), 6.4 (dd, 1H), 7.0 (d, 4H), 7.1 (d, 1H), 7.2-7.3 (m, 5H), 7.7 (d, 1H)

<Synthesis of Compound I-5>

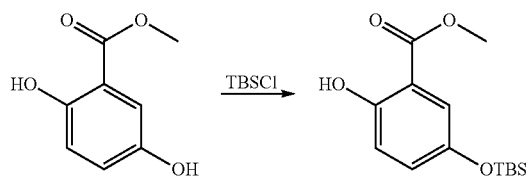

2-(methoxy carbonyl) hydroquinone (3.0 g) and imidazole (1.8 g) were stirred in dichloromethane (60 mL), tert-butyl dimethyl chlorosilane (2.8 g) was added at an internal temperature of 2° C., and the mixture was stirred at room temperature for 5 hours. A dilute hydrochloric acid was added, a water layer was removed, and an organic layer was washed with a dilute hydrochloric acid and saline in this order. The organic layer was dried with magnesium sulfate, the desiccant was filtered, and then, the solvent was distilled under reduced pressure. After that, silica gel (10 g) was added and was stirred in ethyl acetate (50 mL) for 1 hour. The silica gel was filtered, and then, the solvent was distilled under reduced pressure, and thus, phenol I-5 (4.9 g) was obtained.

$^1$H-NMR(Solvent: CDCl$_3$)δ(ppm):

0.2 (s, 6H), 1.0 (s, 9H), 4.0 (s, 3H), 6.8 (d, 1H), 7.0 (dd, 1H), 7.2 (d, 1H), 10.4 (s, 1H)

<Synthesis of Compound I-6>

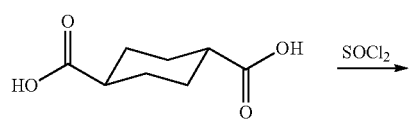

A trans-1,4-cyclohexadicarboxylic acid (5.0 g) was stirred in toluene (30 mL), and was heated to an internal temperature of 75° C., thionyl chloride (6.3 mL) was dropped, and the mixture was stirred for 3 hours. The solvent was distilled under reduced pressure, washing with hexane was performed, and filtration was performed, and thus, a dicarboxylic acid chloride I-6 (4.5 g) was obtained.

<Synthesis of Compound I-7>

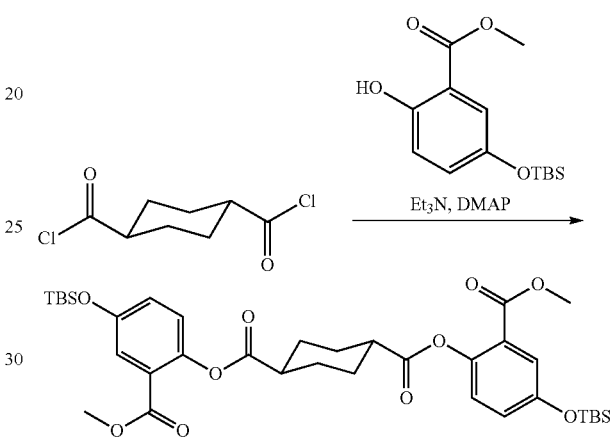

A dicarboxylic acid chloride I-6 (1.7 g) and phenol (4.5 g) were stirred in THF (10 mL). Triethyl amine (2.5 mL) and N,N-dimethyl aminopyridine (0.2 g) were added at an internal temperature of 2° C., and the mixture was stirred at room temperature for 3 hours. Water and ethyl acetate were added, a water layer was removed, and an organic layer was washed with water and saline in this order. The organic layer was dried with magnesium sulfate, the desiccant was filtered, and then, the solvent was distilled under reduced pressure, and thus, ester I-7 was obtained.

<Synthesis of Compound I-8>

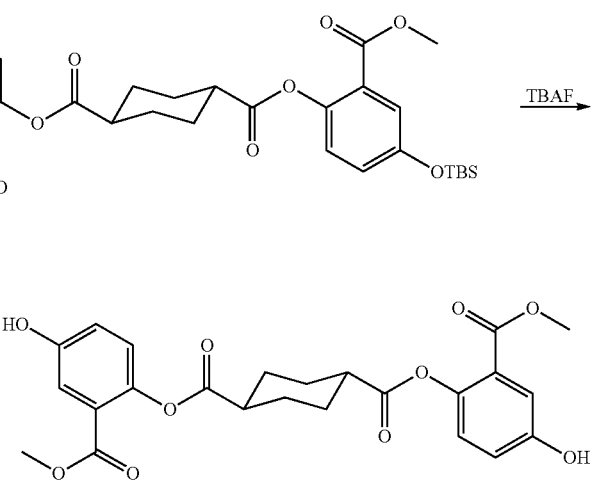

Ester I-7 (5.0 g) was stirred in a mixed solution of THF (16 mL) and an acetic acid (4.6 mL), and an N,N,N,N-tetrabutyl ammonium fluoride/THF solution of 1.0 mol/L (23.8 mL) was dropped at an internal temperature of 2° C. The mixtures was stirred at room temperature for 1 hour, and then, water and ethyl acetate were added, a water layer was removed, and an organic layer was washed with water and saline in this order. The organic layer was dried with magnesium sulfate, the desiccant was filtered, and then, the solvent was distilled under reduced pressure, washing with acetonitrile was performed, and filtration was performed, and thus, a phenol derivative I-8 (1.7 g) was obtained.

$^1$H-NMR(Solvent: CD$_3$OD)δ(ppm):
1.6-1.7 (m, 4H), 2.2-2.4 (m, 4H), 2.5-2.7 (m, 2H), 3.8 (s, 6H), 6.9-7.0 (m, 4H), 7.3 (d, 2H)

<Synthesis of Compound I-9>

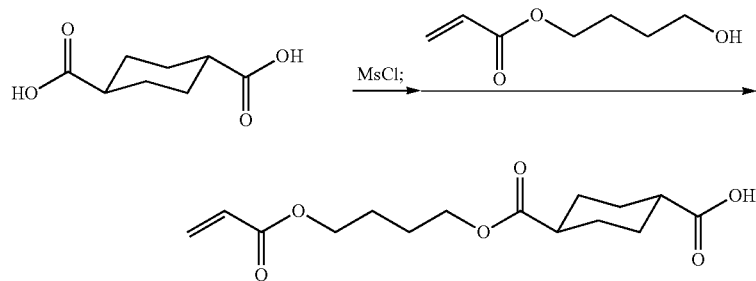

A trans-1,4-cyclohexadicarboxylic acid (10 g), mesyl chloride (1.9 mL), and BHT (0.2 g) were stirred in THF (72 mL), the internal temperature was retained to be lower than or equal to 25° C., and triethyl amine (3.7 mL) was dropped. The mixture was stirred at room temperature for 2 hours, and then, N,N-dimethyl aminopyridine (0.3 g) and 4-hydroxy butyl acrylate (3.1 g) were added, and triethyl amine (3.7 mL) was dropped at an internal temperature of lower than or equal to 25° C. The mixture was stirred at room temperature for 3 hours, and then, a dilute hydrochloric acid and ethyl acetate were added, a water layer was removed, and an organic layer was washed with a dilute hydrochloric acid, a saturated sodium bicarbonate aqueous solution, and saline in this order. The organic layer was dried with magnesium sulfate, the desiccant was filtered, and then, the solvent was distilled under reduced pressure, and thus, a carboxylic acid I-9 (7.1 g) was obtained.

$^1$H-NMR(Solvent: CDCl$_3$)δ(ppm):
1.4-1.6 (m, 4H), 1.6-1.8 (m, 4H), 2.0-2.2 (m, 4H), 2.2-2.4 (m, 2H), 4.1 (t, 2H), 4.2 (t, 2H), 5.8 (dd, 1H), 6.1 (dd, 1H), 6.4 (dd, 1H)

<Synthesis of Compound I-10>

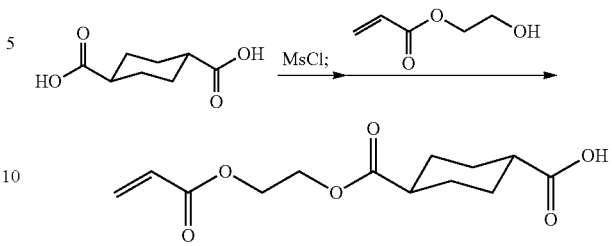

A trans-1,4-cyclohexadicarboxylic acid (10 g), mesyl chloride (1.9 mL), and BHT (0.2 g) were stirred in THF (72 mL), the internal temperature was retained to be lower than or equal to 25° C., and triethyl amine (3.7 mL) was dropped. The mixture was stirred at room temperature for 2 hours, and then, N,N-dimethyl aminopyridine (0.3 g) and 2-hydroxy ethyl acrylate (2.3 mL) were added, and triethyl amine (3.7 mL) was dropped at an internal temperature of lower than or equal to 25° C. The mixture was stirred at room temperature for 3 hours, and then, a dilute hydrochloric acid and ethyl acetate were added, a water layer was removed, and an organic layer was washed with a dilute hydrochloric acid, a saturated sodium bicarbonate aqueous solution, and saline in this order. The organic layer was dried with magnesium sulfate, the desiccant was filtered, and then, the solvent was distilled under reduced pressure, and thus, a carboxylic acid I-9 (3.8 g) was obtained.

$^1$H-NMR(Solvent: CDCl$_3$)δ(ppm):
1.3-1.6 (m, 4H), 2.0-2.2 (m, 4H), 2.2-2.4 (m, 2H), 4.3-4.4 (m, 4H), 5.9 (dd, 1H), 6.1 (dd, 1H), 6.4 (dd, 1H)

<Synthesis of Compound 1>

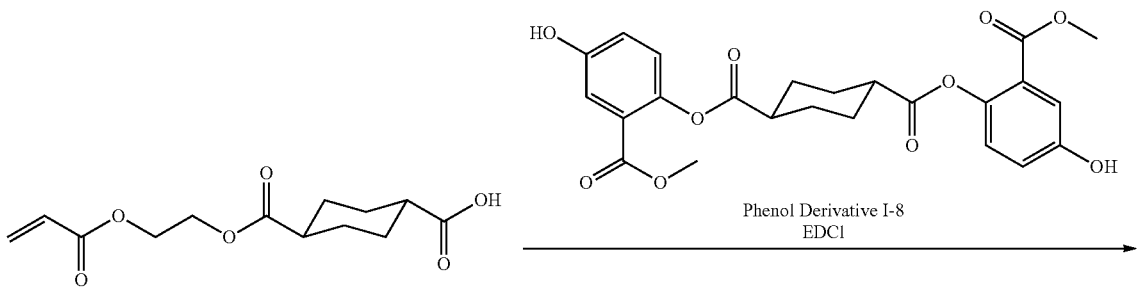

-continued

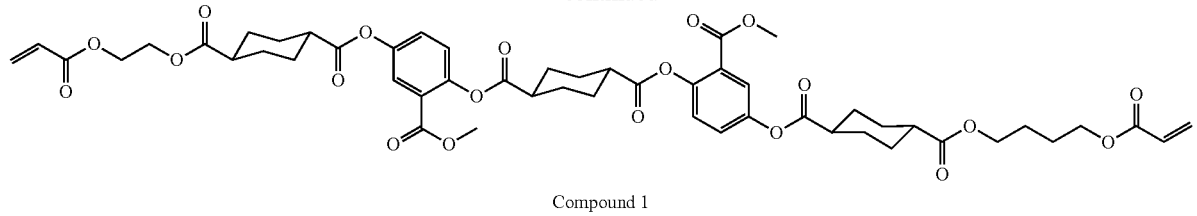

Compound 1

A carboxylic acid I-9 (1.0 g), a phenol derivative I-8 (751 mg), N,N-dimethyl aminopyridine (39 mg), and BHT (18 mg) were stirred in dichloromethane (3.3 mL), 3-[(ethyl carbon imidoyl) amino]-N,N-dimethyl-1-propane amine hydrochloride (914 mg) was added, and the mixture was stirred at room temperature for 4 hours. Celite filtration was performed, and then, water was added to the filtrate, a water layer was removed, and an organic layer was dried with magnesium sulfate. The desiccant was filtered, BHT (10 mg) was added, and the solvent was distilled under reduced pressure. Methanol (5 mL) was added, cooling was performed until the internal temperature became 0° C., and the generated crystal was filtered, and thus, a compound 1 was obtained.

$^1$H-NMR(Solvent: CDCl$_3$)δ(ppm):
1.5-1.6 (m, 8H), 1.6-1.8 (m, 10H), 2.1-2.4 (m, 16H), 2.5-2.7 (m, 4H), 3.9 (s, 6H), 4.1-4.2 (m, 8H), 5.8 (dd, 2H), 6.1 (dd, 2H), 6.4 (dd, 2H), 7.1 (d, 2H), 7.3 (dd, 2H), 7.7 (d, 2H)

<Synthesis of Mixture A>

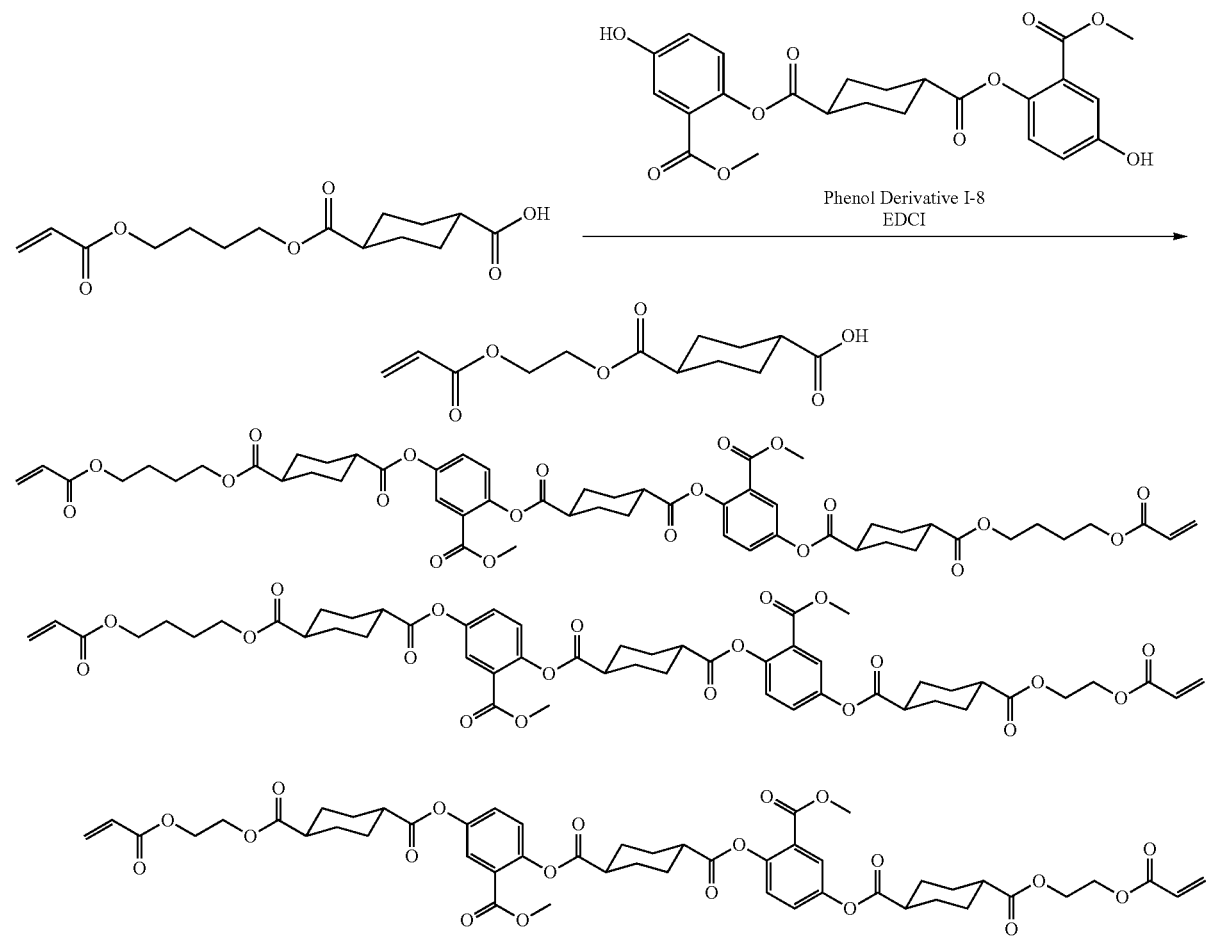

A carboxylic acid I-9 (332 mg), a carboxylic acid I-10 (301 mg), a phenol derivative I-8 (500 mg), N,N-dimethyl aminopyridine (26 mg), and BHT (12 mg) were stirred in dichloromethane (2.1 mL), 3-[(ethyl carbon imidoyl) amino]-N,N-dimethyl-1-propane amine hydrochloride (920 mg) was added, and the mixture was stirred for 4 hours. Celite filtration was performed, and then, water was added to the filtrate, a water layer was removed, and an organic layer was dried with magnesium sulfate. The desiccant was filtered, BHT (10 mg) was added, and the solvent was distilled under reduced pressure. Methanol (5 mL) was added, cooling was performed until the internal temperature became 0° C., and the generated crystal was filtered, and thus, a mixture A (a mixture of compounds 1, 3, and 5) (410 mg) was obtained.

MALDI-MS m/z=999.378 [m+Na]⁺, 1027.412 [m+Na]⁺, and 1055.447 [m+Na]⁺

<Synthesis of Compound I-11>

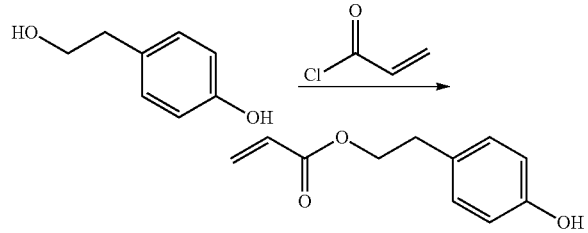

2-(4-hydroxy phenyl) ethanol (10 g), pyridine (7.0 mL), and BHT (0.8 g) were stirred in ethyl acetate (72 mL). Acryloyl chloride (6.9 g) was dropped at an internal temperature of 3° C., and the mixture was stirred at an internal temperature of 3° C. to 5° C. for 8 hours. Water and ethyl acetate were added, a water layer was removed, and an organic layer was washed with water and saline in this order. The organic layer was dried with magnesium sulfate, the desiccant was filtered, and then, the solvent was distilled under reduced pressure. Purification was performed by a column chromatography (Hexane:Ethyl Acetate=2:1), and thus, a phenol derivative I-11 was obtained.

¹H-NMR(Solvent: CDCl₃)δ(ppm):

2.9 (t, 2H), 4.3 (t, 2H), 5.0 (s, 1H), 5.8 (dd, 1H), 6.1 (dd, 1H), 6.4 (dd, 1H), 6.8 (d, 2H), 7.1 (d, 2H)

<Synthesis of Compound I-12>

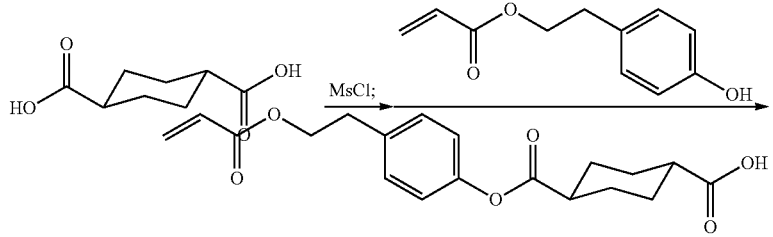

A trans-1,4-cyclohexadicarboxylic acid (3.4 g), mesyl chloride (1.2 g), and BHT (0.1 g) were stirred in THF (30 mL), the internal temperature was retained to be lower than or equal to 25° C., and triethyl amine (1.5 mL) was dropped. The mixture was stirred at room temperature for 2 hours, N,N-dimethyl aminopyridine (0.1 g) and a phenol derivative I-11 (1.9 g) were added, and triethyl amine (1.5 mL) was dropped at an internal temperature of lower than or equal to 25° C. The mixtures was stirred at room temperature for 3 hours, and then, a dilute hydrochloric acid and ethyl acetate were added, a water layer was removed, and an organic layer was washed with a dilute hydrochloric acid, a saturated sodium bicarbonate aqueous solution, and saline in this order. The organic layer was dried with magnesium sulfate, the desiccant was filtered, and the solvent was distilled under reduced pressure, and thus, a carboxylic acid I-12 (1.4 g) was obtained.

¹H-NMR(Solvent: CD₃OD)δ(ppm):

1.3-1.7 (m, 4H), 1.9-2.4 (m, 5H), 2.5-2.6 (m, 1H), 3.0 (t, 2H), 4.3 (t, 2H), 5.9 (dd, 1H), 6.1 (dd, 1H), 6.3 (dd, 1H), 7.0 (d, 2H), 7.3 (d, 2H)

<Synthesis of Compound 33>

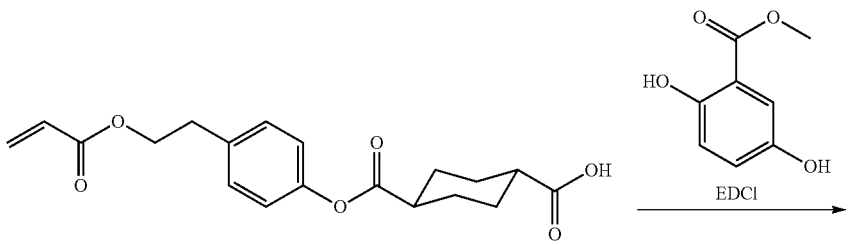

Carboxylic Acid I-12

-continued

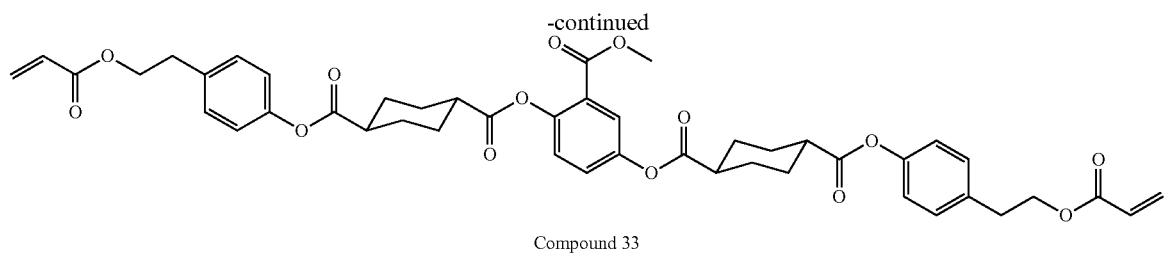

Compound 33

A carboxylic acid I-12 (600 mg), 2-(methoxy carbonyl) hydroquinone (242 mg), N,N-dimethyl aminopyridine (11 mg), and BHT (9.5 mg) were stirred in a mixed solvent of dichloromethane (4 mL) and DMAc (2 mL), 3-[(ethyl carbon imidoyl) amino]-N,N-dimethyl-1-propane amine hydrochloride (498 mg) was added, and the mixture was stirred at room temperature for 6 hours. Silica gel filtration was performed, and then, water was added to the filtrate, a water layer was removed, and an organic layer was dried with magnesium sulfate. The desiccant was filtered, BHT (10 mg) was added, and the solvent was distilled under reduced pressure. Methanol (5 mL) was added, cooling was performed until the internal temperature became 0° C., and the generated crystal was filtered, and thus, a compound 33 was obtained.

$^1$H-NMR(Solvent: CDCl$_3$)δ(ppm):
1.4-1.8 (m, 8H), 2.1-2.4 (m, 8H), 2.5-2.8 (m, 4H), 3.0 (s, 4H), 3.9 (s, 3H), 4.4 (t, 4H), 5.8 (dd, 2H), 6.1 (dd, 2H), 6.4 (dd, 2H), 7.0-7.1 (m, 4H), 7.2-7.3 (m, 5H), 7.7-7.8 (m, 2H)

<Synthesis of Compound 34>

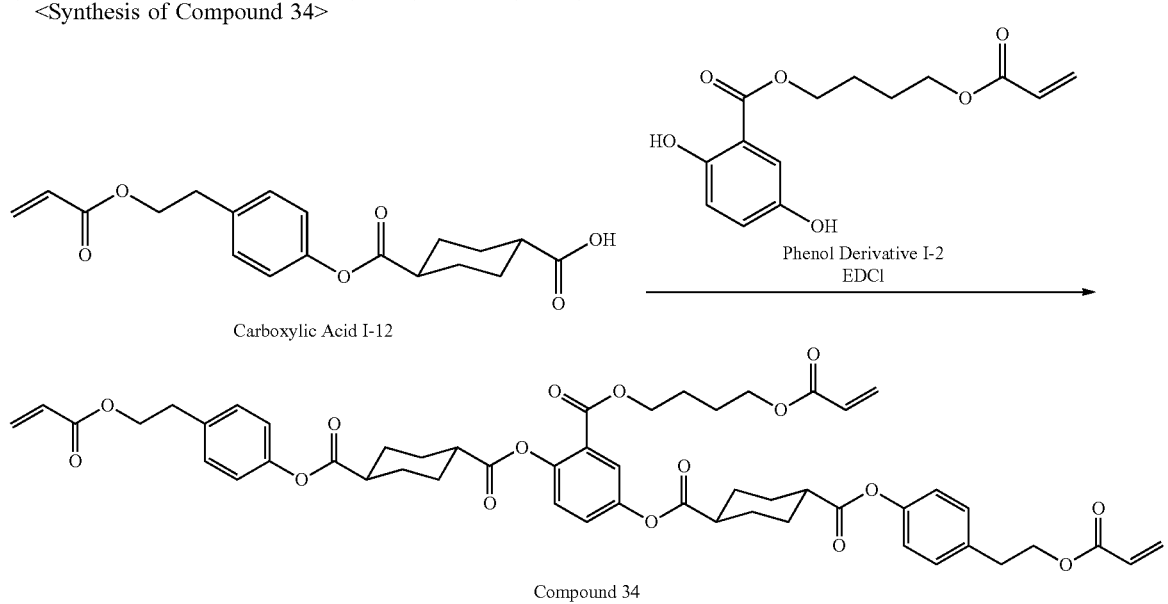

Compound 34

A carboxylic acid I-12 (600 mg), a phenol derivative I-2 (145 mg), N,N-dimethyl aminopyridine (11 mg) and BHT (9.5 mg) were stirred in a mixed solvent of dichloromethane (4 mL) and DMAc (2 mL), 3-[(ethyl carbon imidoyl) amino]-N,N-dimethyl-1-propane amine hydrochloride (498 mg) was added, and the mixture was stirred at room temperature for 6 hours. Silica gel filtration was performed, and then, water was added to the filtrate, a water layer was removed, and an organic layer was dried with magnesium sulfate. The desiccant was filtered, BHT (10 mg) was added, and the solvent was distilled under reduced pressure. Methanol (5 mL) was added, cooling was performed until the internal temperature became 0° C., and the generated crystal was filtered, and thus, a compound 34 was obtained.

$^1$H-NMR(Solvent: CDCl$_3$)δ(ppm):
1.4-2.0 (m, 12H), 2.1-2.4 (m, 8H), 2.5-2.7 (m, 4H), 3.0 (t, 4H), 4.2-4.4 (m, 8H), 5.8-5.9 (m, 3H), 6.0-6.2 (m, 3H), 6.3-6.5 (m, 3H), 7.0-7.1 (m, 4H), 7.2-7.4 (m, 5H), 7.5-7.7 (m, 2H)

<Synthesis of Compound I-13>

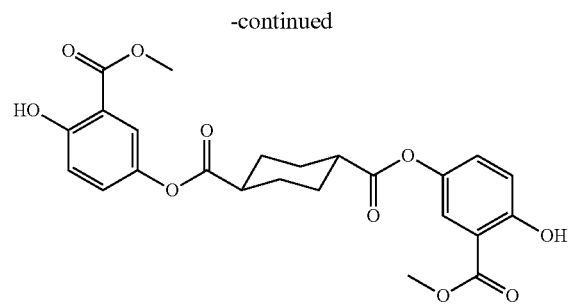

-continued

A dicarboxylic acid chloride I-6 (960 mg) and 2-(methoxy carbonyl) hydroquinone (1.5 g) were stirred in THF (5.7 mL). Triethyl amine (1.5 mL) and N,N-dimethyl aminopyridine (56 mg) were added at an internal temperature of 2° C., and the mixture was stirred at room temperature for 2 hours. Water and ethyl acetate were added, a water layer was removed, and an organic layer was washed with water and saline in this order. The organic layer was dried with magnesium sulfate, the desiccant was filtered, and then, the solvent was distilled under reduced pressure. Methanol (15 mL) was added, the mixture was stirred at an internal temperature of 0° C. for 30 minutes, and the generated crystal was filtered, and thus, 1.85 g of a compound I-13 was obtained.

$^1$H-NMR(Solvent: CDCl$_3$)δ(ppm):
1.6-1.7 (m, 4H), 2.2-2.4 (m, 4H), 2.5-2.6 (m, 2H), 3.9 (s, 6H), 7.0 (d, 2H), 7.2 (dd, 2H), 7.6 (d, 2H)

<Synthesis of Compound 47>

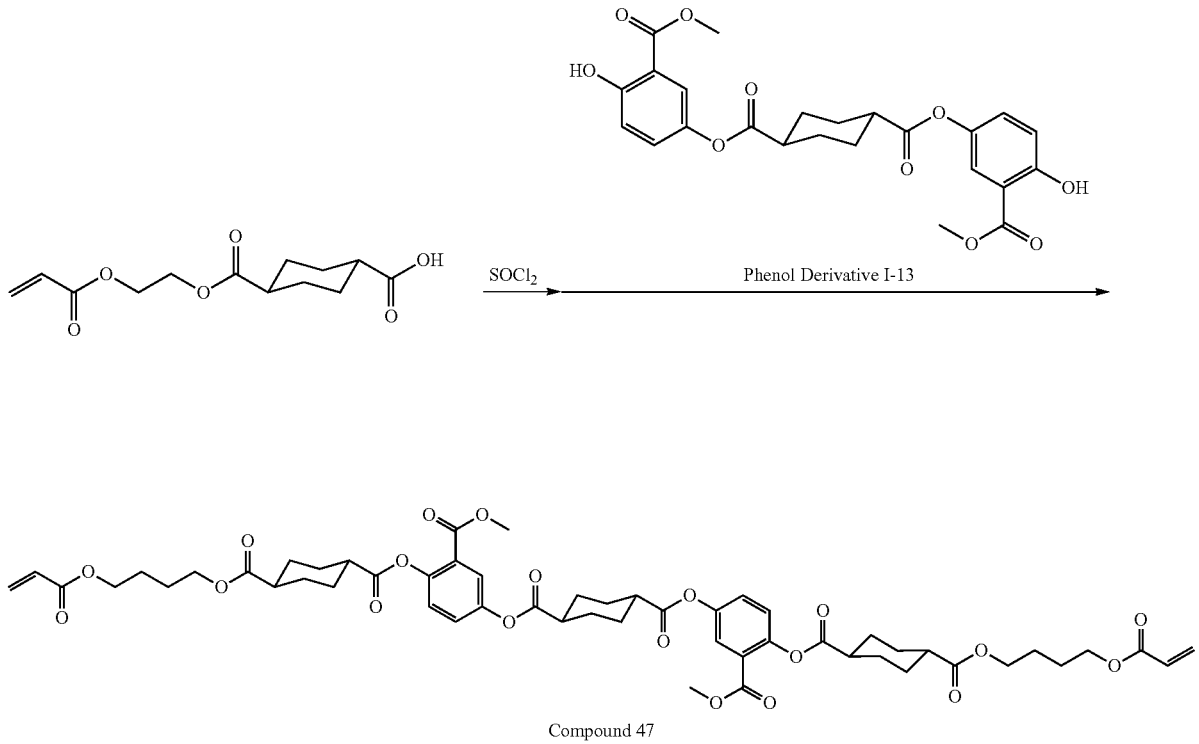

Compound 47

A carboxylic acid I-9 (1.72 g), BHT (0.3 g) and thionyl chloride (0.47 mL) were stirred in toluene (2.7 mL) at room temperature for 1 hour. The solvent was distilled under reduced pressure, and then, ethyl acetate (5 mL) and a phenol derivative I-13 (0.8 g) were added, N,N-dimethyl aminopyridine (0.1 g) and triethyl amine (1.1 mL) were dropped, and the mixture was stirred at room temperature for 3 hours. Methanol (1 mL) was added, the mixture was stirred at room temperature for 15 minutes, and then, water and ethyl acetate were added, a water layer was removed, and an organic layer was washed with a dilute hydrochloric acid and saline in this order. The organic layer was dried with magnesium sulfate, the desiccant was filtered, and then, the solvent was distilled under reduced pressure. Methanol (15 mL) was added, the mixture was stirred at an internal temperature of 0° C. for 30 minutes, and the generated crystal was filtered, and thus, 1.2 g of a compound 47 was obtained.

$^1$H-NMR(Solvent: CDCl$_3$)δ(ppm):
1.5-1.8 (m, 20H), 2.1-2.2 (m, 4H), 2.2-2.4 (m, 10H), 2.5-2.7 (m, 4H), 3.9 (s, 6H), 4.1-4.3 (m, 8H), 5.8 (dd, 2H), 6.1 (dd, 2H), 6.4 (dd, 2H), 7.1 (d, 2H), 7.3 (dd, 2H), 7.7 (d, 2H)

<Synthesis of Compound 49>

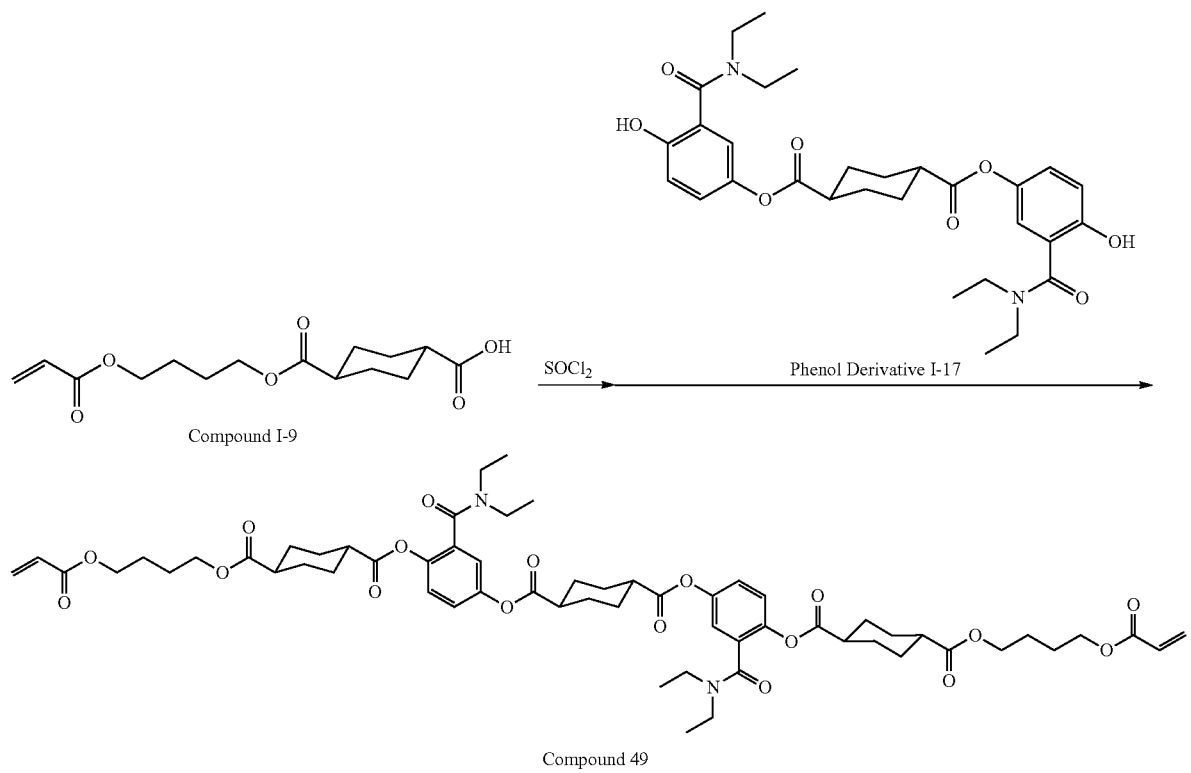

Compound 49

A phenol derivative I-17 was synthesized by the same method as that of the compound I-13. Further, a compound 49 was obtained by using the same synthesis method as that of the compound 47.

$^1$H-NMR(Solvent: CDCl$_3$)δ(ppm):
1.1 (t, 3H), 1.2 (t, 3H), 1.4-1.8 (m, 20H), 2.0-2.4 (m, 14H), 2.4-2.6 (m, 4H), 3.1-3.3 (m, 4H), 3.4-3.6 (m, 4H), 4.1-4.3 (m, 8H), 5.8 (dd, 2H), 6.1 (dd, 2H), 6.4 (dd, 2H), 7.0-7.2 (m, 6H)

<Synthesis of Compound 50>

The phenol derivative described above was synthesized by the same method as that of the compound I-8. Further, a compound 50 was obtained by using the same synthesis method as that of the compound 1.

$^1$H-NMR(Solvent: CDCl$_3$)δ(ppm):
1.0 (t, 6H), 1.4-1.8 (m, 28H), 2.1-2.4 (m, 14H), 2.5-2.7 (m, 4H), 4.1-4.3 (m, 12H), 5.8 (dd, 2H), 6.1 (dd, 2H), 6.4 (dd, 2H), 7.1 (d, 2H), 7.3 (dd, 2H), 7.7 (d, 2H)

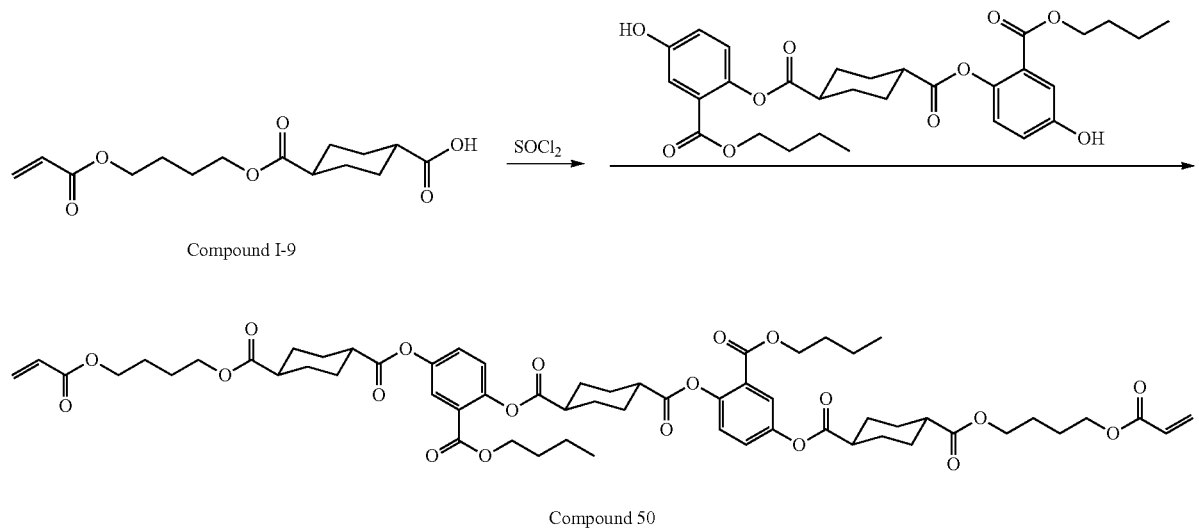

Compound 50

<Synthesis of Compound 51>

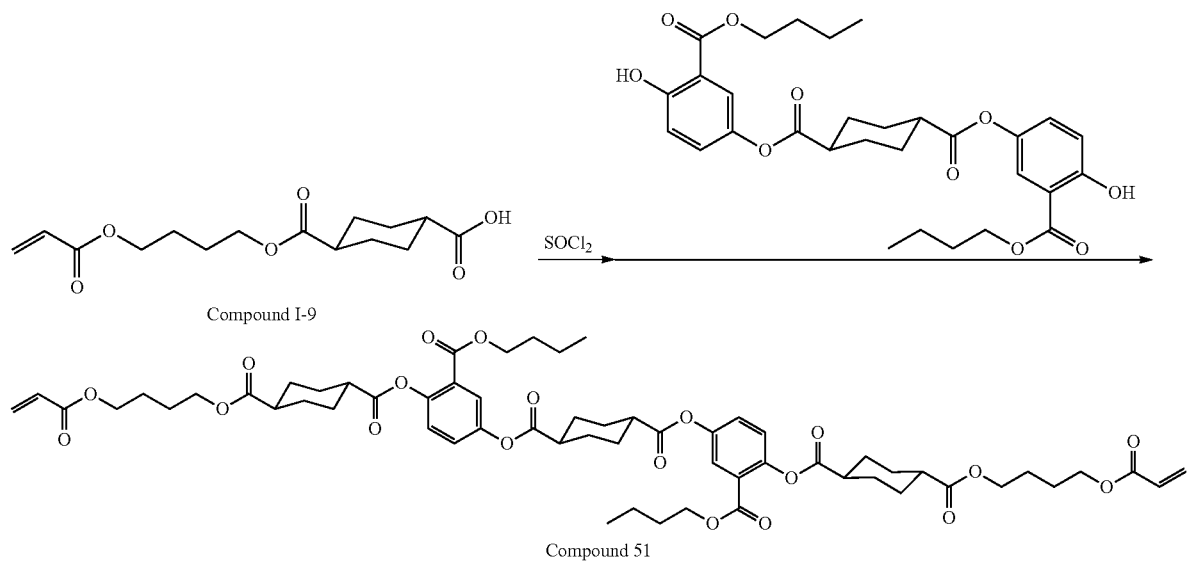

Compound 51

The phenol derivative described above was synthesized by the same method as that of the compound I-13. Further, a compound 51 was obtained by using the same synthesis method as that of the compound 47.

$^1$H-NMR(Solvent: CDCl$_3$)δ(ppm):
1.0 (t, 6H), 1.4-1.8 (m, 28H), 2.1-2.2 (m, 4H), 2.2-2.4 (m, 10H), 2.5-2.7 (m, 4H), 4.1-4.3 (m, 12H), 5.8 (dd, 2H), 6.1 (dd, 2H), 6.4 (dd, 2H), 7.1 (d, 2H), 7.3 (dd, 2H), 7.7 (d, 2H)

<Synthesis of Compound 52>

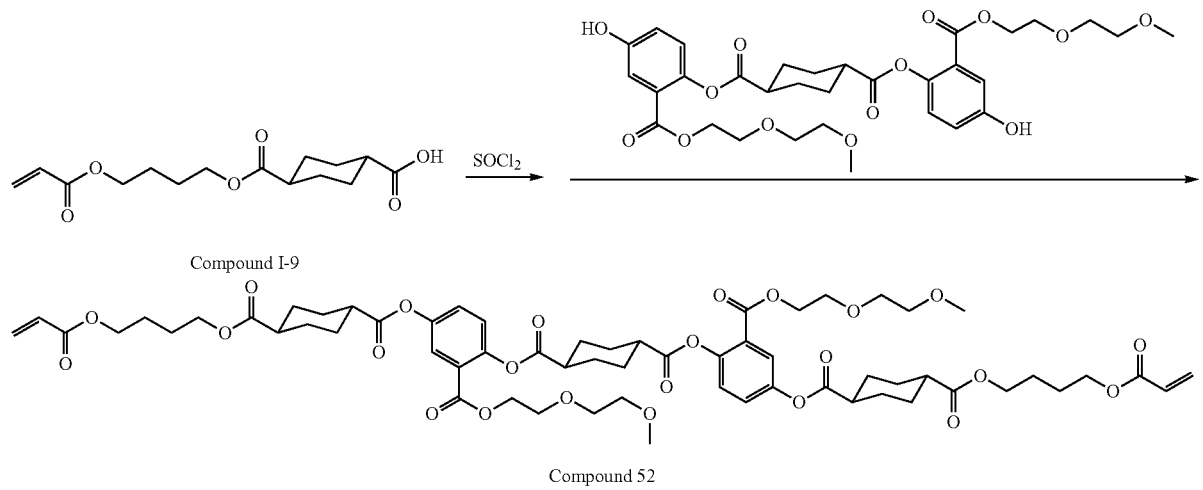

Compound 52

The phenol derivative described above was synthesized by the same method as that of the compound I-8. Further, a compound 52 was obtained by using the same synthesis method as that of the compound 1.

$^1$H-NMR(Solvent: CDCl$_3$)δ(ppm):
1.4-1.8 (m, 20H), 2.0-2.4 (m, 14H), 2.5-2.7 (m, 4H), 3.4 (s, 6H), 3.6 (t, 4H), 3.7 (t, 4H), 3.8 (t, 4H), 4.1-4.2 (m, 8H), 4.4 (t, 4H), 5.8 (dd, 2H), 6.1 (dd, 2H), 6.4 (dd, 2H), 7.1 (d, 2H), 7.3 (dd, 2H), 7.7 (d, 2H)

<Synthesis of Compound 53>

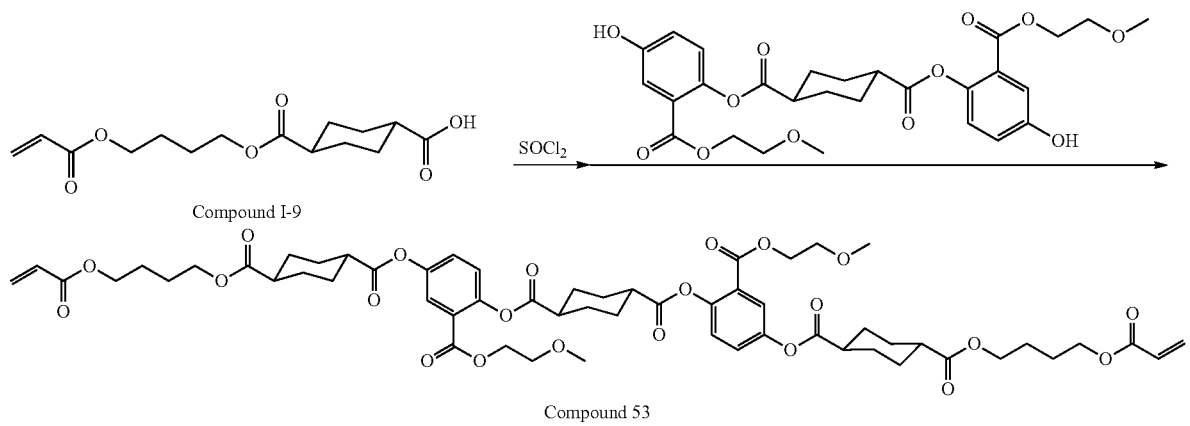

Compound 53

The phenol derivative described above was synthesized by the same method as that of the compound I-8. Further, a compound 53 was obtained by using the same synthesis method as that of the compound 1.

$^1$H-NMR(Solvent: CDCl$_3$)δ(ppm):
1.5-1.8 (m, 20H), 2.1-2.3 (m, 8H), 2.3-2.4 (m, 6H), 2.5-2.6 (m, 2H), 2.6-2.7 (m, 2H), 3.4 (s, 6H), 3.6-3.7 (m, 4H), 4.1-4.2 (m, 8H), 4.4-4.5 (m, 4H), 5.8 (dd, 2H), 6.1 (dd, 2H), 6.4 (dd, 2H), 7.1 (d, 2H), 7.3 (dd, 2H), 7.7 (d, 2H)

<Synthesis of Compound 54>

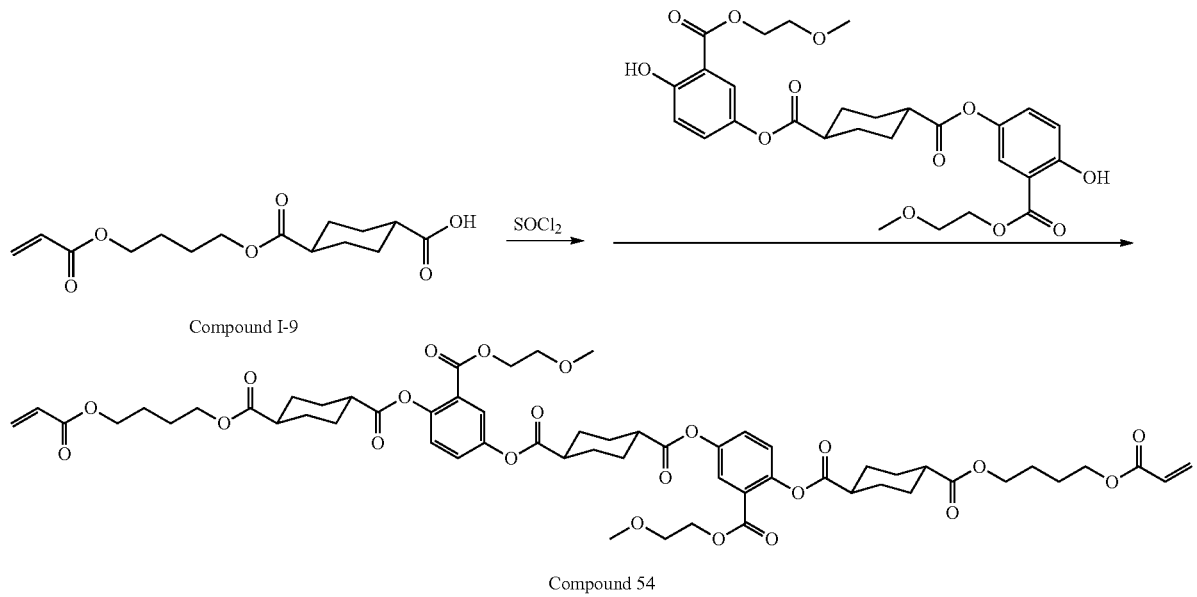

Compound 54

The phenol derivative described above was synthesized by the same method as that of the compound I-13. Further, a compound 54 was obtained by using the same synthesis method as that of the compound 47.

$^1$H-NMR(Solvent: CDCl$_3$)δ(ppm):
1.3-2.0 (m, 20H), 2.1-2.2 (m, 4H), 2.2-2.4 (m, 10H), 2.5-2.7 (m, 4H), 3.5 (s, 6H), 3.6-3.7 (m, 4H), 4.1-4.2 (m, 8H), 4.4-4.5 (m, 4H), 5.8 (dd, 2H), 6.1 (dd, 2H), 6.4 (dd, 2H), 7.1 (d, 2H), 7.3 (dd, 2H), 7.7 (d, 2H)

<Synthesis of Compound 55>

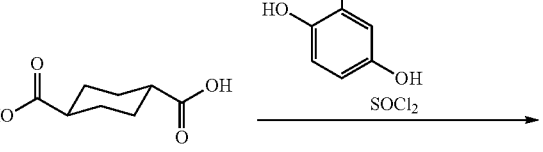

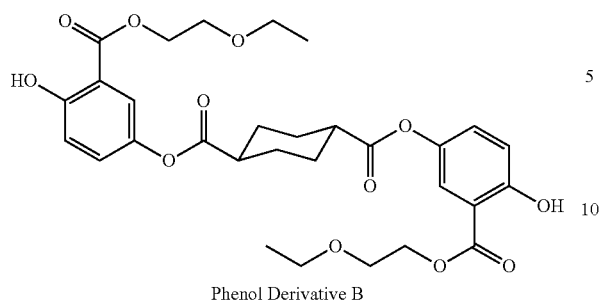
Phenol Derivative B

A mixture of a trans-1,4-cyclohexane dicarboxylic acid (5 g), toluene (40 mL), and N,N-dimethyl formamide (0.05 mL) was heated and stirred, thionyl chloride (8.3 g) was dropped at an internal temperature of 80° C., and then, heating and stirring was performed at an internal temperature of 80° C. for 2 hours. The mixtures was cooled to an internal temperature of 30° C., and then, 2-ethoxy ethyl-2,5-dihydroxy benzoate (13.1 g) was added, and the mixture was heated and stirred at an internal temperature of 90° C. for 4 hours. Methanol (60 mL) was added at an internal temperature of 40° C., and then, the mixture was further stirred at an internal temperature of 5° C. for 30 minutes, and the generated crystal was filtered, and thus, 11.5 g of a phenol derivative B was obtained.

$^1$H-NMR(Solvent: CDCl$_3$)δ(ppm):
1.25 (t, 6H), 1.6-1.7 (m, 4H), 2.2-2.4 (m, 4H), 2.5-2.6 (m, 2H), 3.55-3.65 (m, 4H), 3.8-3.85 (m, 4H), 4.45-4.5 (m, 4H), 7.0 (d, 2H), 7.2 (dd, 2H), 7.6 (d, 2H)

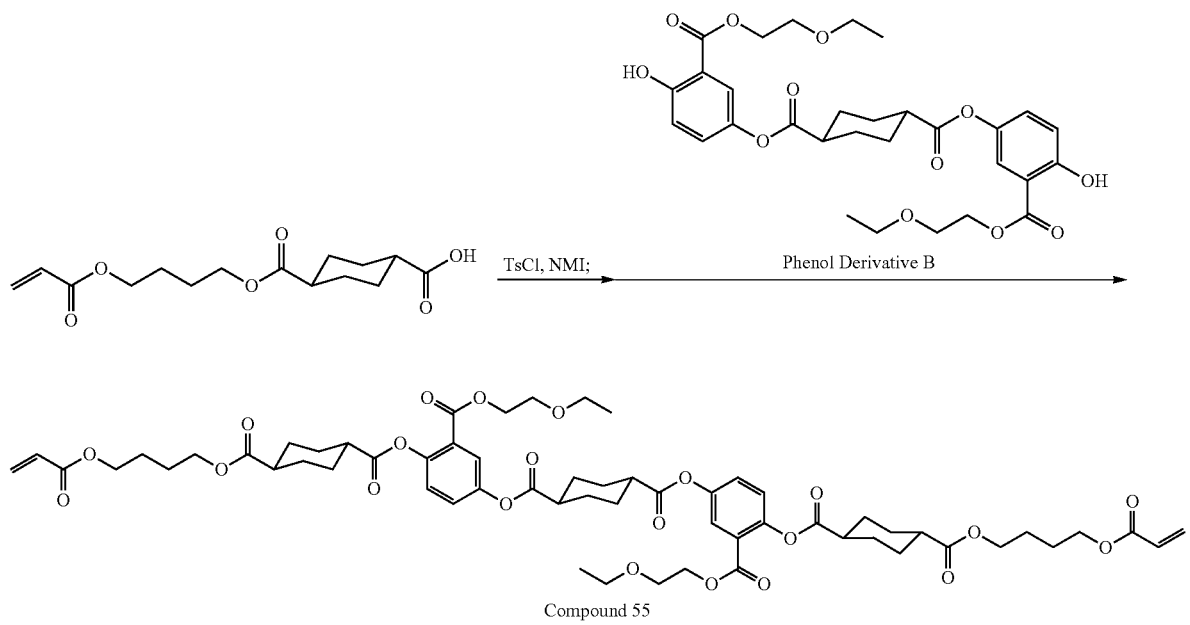 [SMILES: CCOCCOC(=O)c1cc(OC(=O)C2CCC(C(=O)Oc3ccc(O)c(C(=O)OCCOCC)c3)CC2)ccc1O ; C=CC(=O)OCCCCOC(=O)C1CCC(C(=O)O)CC1 ; "TsCl, NMI;" ; C=CC(=O)OCCCCOC(=O)C1CCC(C(=O)Oc2ccc(OC(=O)C3CCC(C(=O)Oc4ccc(OC(=O)C5CCC(C(=O)OCCCCOC(=O)C=C)CC5)c(C(=O)OCCOCC)c4)CC3)cc2C(=O)OCCOCC)CC1]
Compound 55

A compound I-9 (13.4 g), TsCl (10.3 g), and BHT (0.2 g) were stirred in THF (40 mL) and 1-ethyl 2-pyrrolidone (25 mL), 1-methyl imidazole (11 mL) was dropped under ice cooling, and the mixture was stirred at room temperature for 1 hour. A phenol derivative B (10.6 g) was added, and the mixture was further stirred at room temperature for 2 hours. Water (10 mL) was added, and then, a water layer was removed, water and methanol were added, the mixture was stirred for 1 hour under ice cooling, and the generated crystal was filtered, and thus, a compound 55 (18.3 g) was obtained.

$^1$H-NMR(Solvent: CDCl$_3$)δ(ppm):
1.2 (t, 6H), 1.4-1.8 (m, 18H), 2.1-2.2 (m, 4H), 2.2-2.4 (m, 12H), 2.5-2.7 (m, 4H), 3.5 (q, 4H), 3.7-3.8 (m, 4H), 4.1-4.3 (m, 8H), 4.4-4.5 (m, 4H), 5.8 (dd, 2H), 6.1 (dd, 2H), 6.4 (dd, 2H), 7.1 (d, 2H), 7.3 (dd, 2H), 7.7 (d, 2H)

<Synthesis of Compound 56>

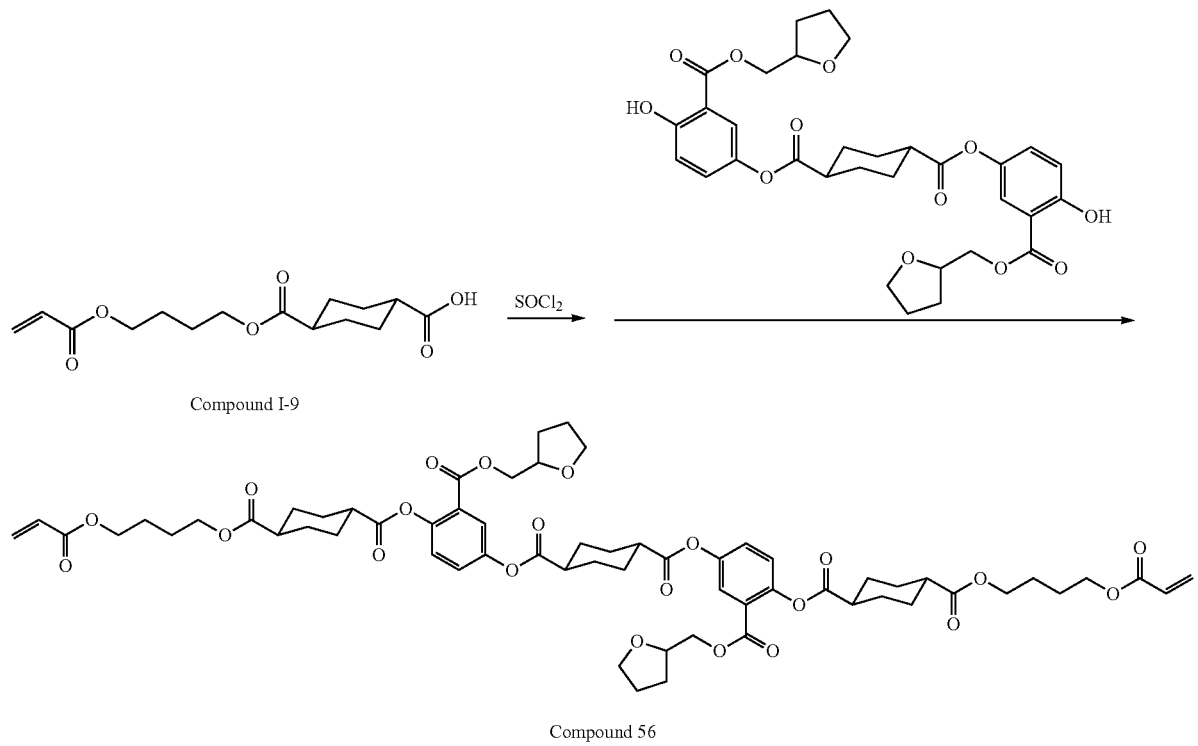

The phenol derivative described above was synthesized by the same method as that of the compound I-13. Further, a compound 56 was obtained by using the same synthesis method as that of the compound 47.

$^1$H-NMR(Solvent: CDCl$_3$)δ(ppm):
1.4-1.8 (m, 26H), 1.9-2.0 (m, 4H), 2.0-2.2 (m, 4H), 2.2-2.4 (m, 10H), 2.5-2.7 (m, 4H), 3.8-4.0 (m, 4H), 4.1-4.4 (m, 12H), 5.8 (dd, 2H), 6.1 (dd, 2H), 6.4 (dd, 2H), 7.1 (d, 2H), 7.3 (dd, 2H), 7.7 (d, 2H)

<Synthesis of Compound 57>

The phenol derivative described above was synthesized by the same method as that of the compound I-13. Further, a compound 57 was obtained by using the same synthesis method as that of the compound 47.

$^1$H-NMR(Solvent: CDCl$_3$)δ(ppm):
1.2 (d, 6H), 1.5-1.8 (m, 22H), 1.8-2.0 (m, 4H), 2.1-2.2 (m, 4H), 2.2-2.4 (m, 10H), 2.5-2.7 (m, 4H), 3.3 (s, 6H), 4.1-4.3 (m, 8H), 4.3-4.4 (m, 4H), 5.8 (dd, 2H), 6.1 (dd, 2H), 6.4 (dd, 2H), 7.1 (d, 2H), 7.3 (dd, 2H), 7.7 (d, 2H)

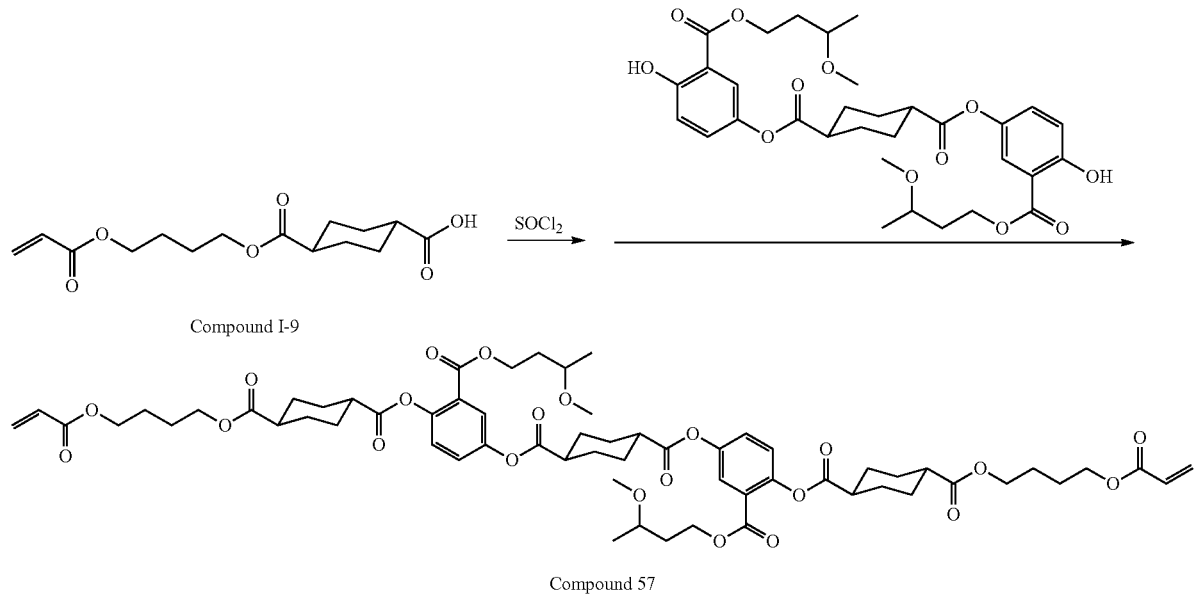

<Synthesis of Compound 58>
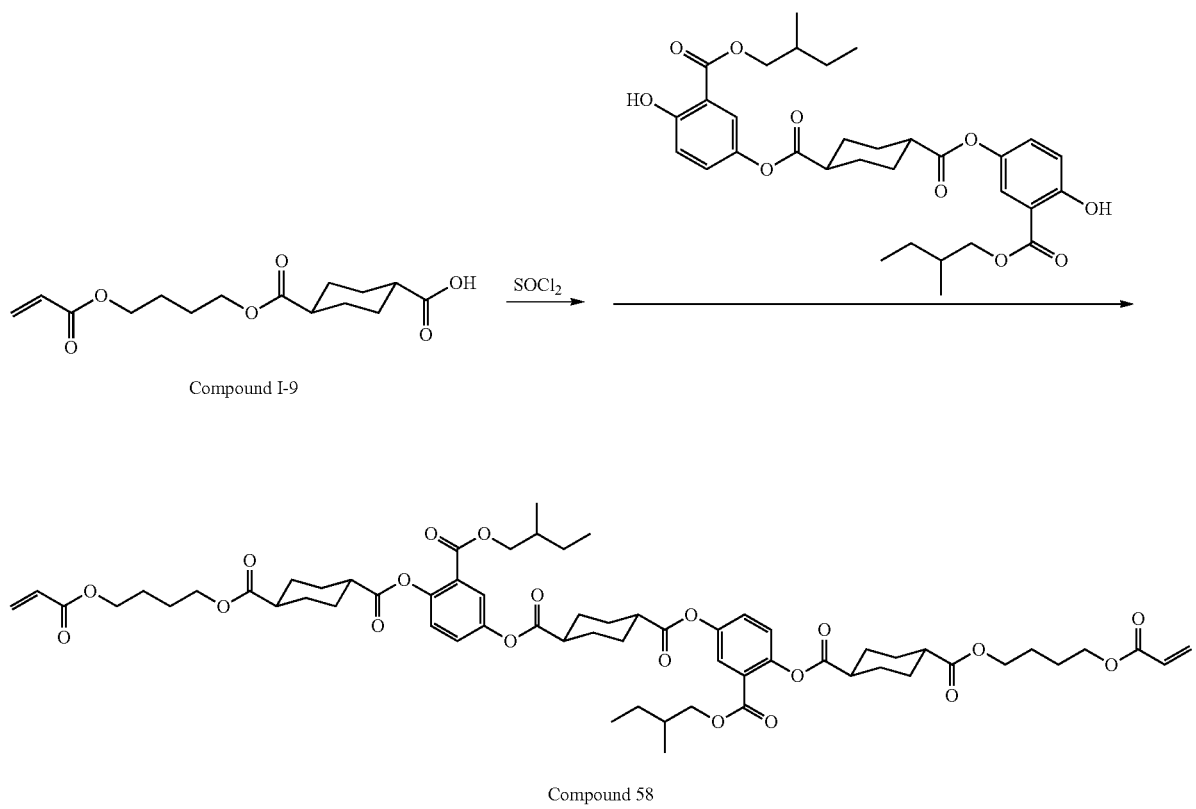
Compound 58
A phenol derivative was synthesized by the same method as that of the compound I-13. Further, a compound 58 was obtained by using the same synthesis method as that of the compound 47.
$^1$H-NMR(Solvent: CDCl$_3$)δ(ppm):
0.9-1.0 (m, 12H), 1.2-1.3 (m, 2H), 1.4-1.9 (m, 24H), 2.1-2.2 (m, 4H), 2.2-2.4 (m, 10H), 2.5-2.7 (m, 4H), 4.0-4.3 (m, 12H), 5.8 (dd, 2H), 6.1 (dd, 2H), 6.4 (dd, 2H), 7.1 (d, 2H), 7.3 (dd, 2H), 7.7 (d, 2H)
<Synthesis of Compound 59>
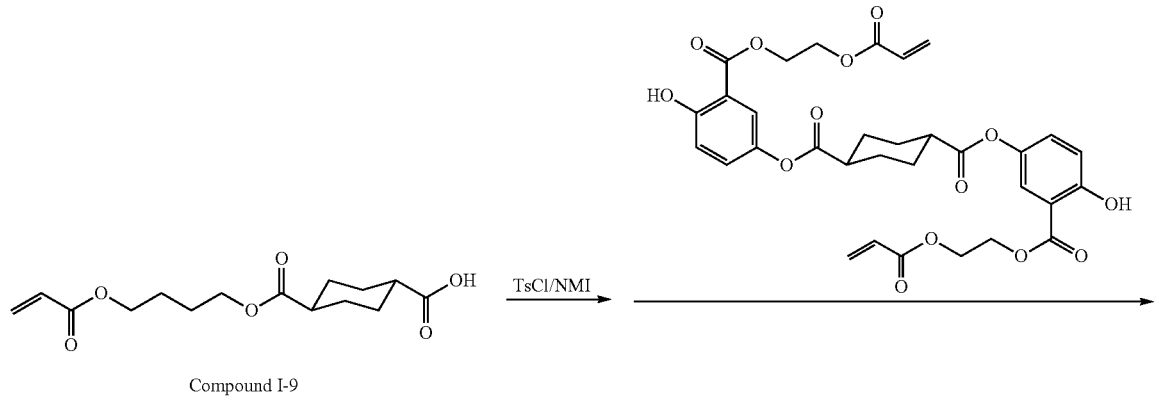

-continued

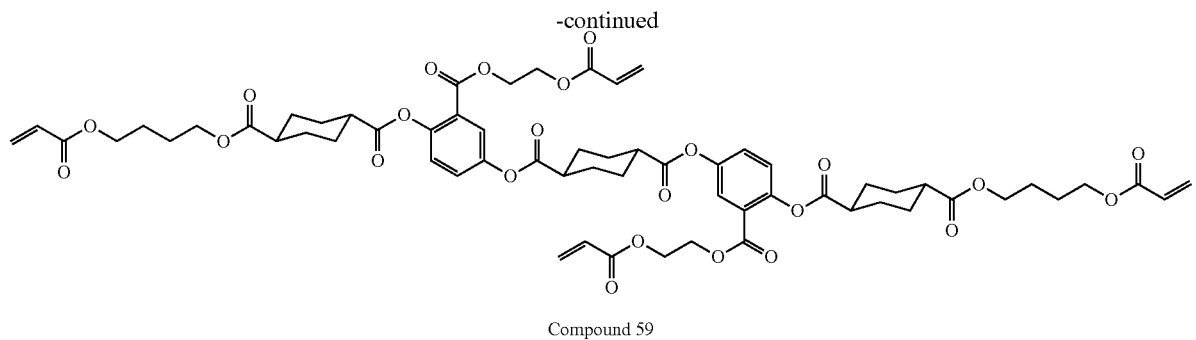

Compound 59

A phenol derivative was synthesized by the same method as that of the compound I-13. Further, a compound 59 was obtained by using the same synthesis method as that of the compound 55, and by being purified by a column chromatography.

$^1$H-NMR(Solvent: CDCl$_3$)δ(ppm):
1.45-1.8 (m, 18H), 2.1-2.2 (m, 4H), 2.25-2.4 (m, 12H), 2.5-2.7 (m, 4H), 4.1-4.35 (m, 8H), 4.4-4.55 (m, 8H), 5.8 (dd, 4H), 6.1 (dd, 4H), 6.4 (dd, 4H), 7.1 (d, 2H), 7.3 (dd, 2H), 7.7 (d, 2H)

<Synthesis of Compound 62>

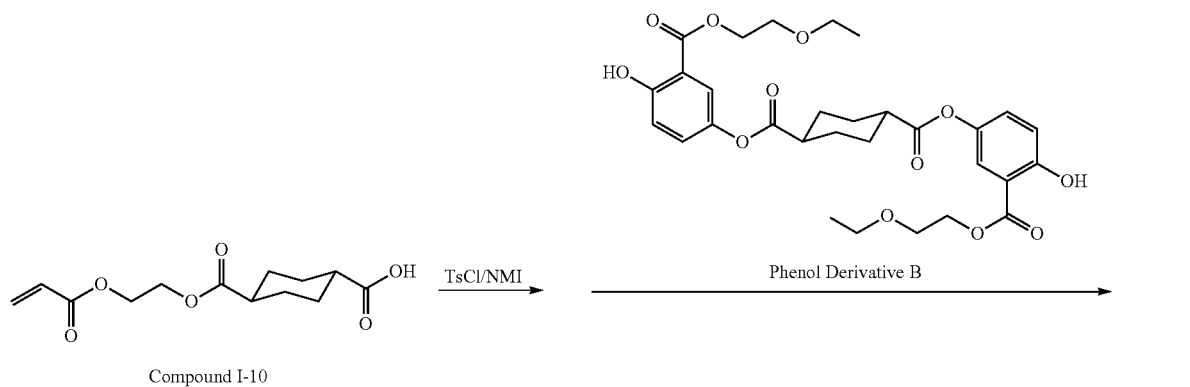

Compound I-10

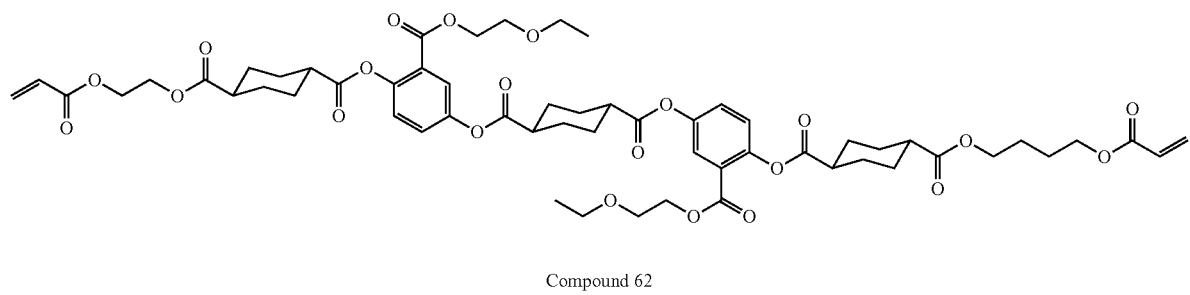

Compound 62

A compound 62 was obtained by using the same synthesis method as that of the compound 55.

$^1$H-NMR(Solvent: CDCl$_3$)δ(ppm):
1.2 (t, 6H), 1.5-1.7 (m, 12H), 2.1-2.2 (m, 4H), 2.2-2.5 (m, 10H), 2.5-2.7 (m, 4H), 3.5 (q, 4H), 3.7-3.8 (m, 4H), 4.3-4.4 (m, 12H), 5.9 (dd, 2H), 6.1 (dd, 2H), 6.4 (dd, 2H), 7.1 (d, 2H), 7.3 (dd, 2H), 7.7 (d, 2H)

<Synthesis of Compound 60>

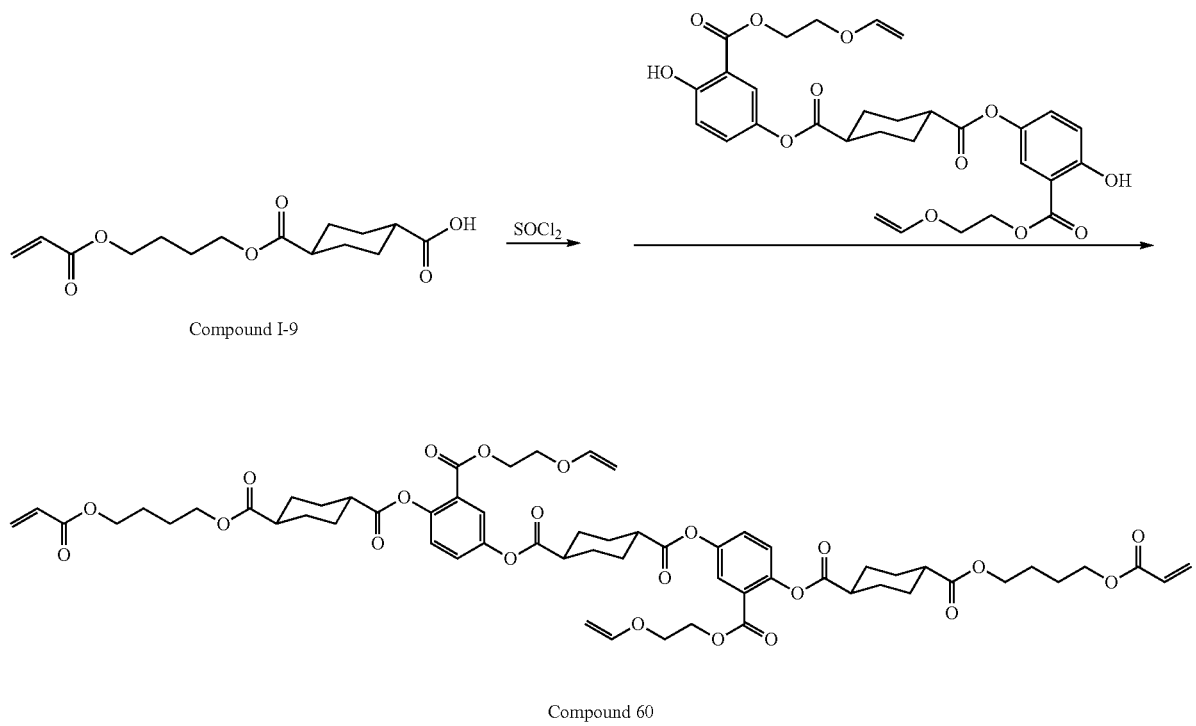

Compound 60

The phenol derivative described above was synthesized by the same method as that of the compound I-13. Further, a compound 60 was obtained by using the same synthesis method as that of the compound 47, and by being purified by a column chromatography.

$^1$H-NMR(Solvent: CDCl$_3$)δ(ppm):
1.5-1.8 (m, 20H), 2.1-2.2 (m, 4H), 2.2-2.4 (m, 10H), 2.5-2.7 (m, 4H), 3.9-4.0 (m, 4H), 4.1-4.3 (m, 12H), 4.45-4.55 (m, 4H), 5.8 (dd, 2H), 6.1 (dd, 2H), 6.4 (dd, 2H), 6.55 (dd, 2H), 7.1 (d, 2H), 7.3 (dd, 2H), 7.7 (d, 2H)

<Synthesis of Mixture of Compounds 66 to 68>

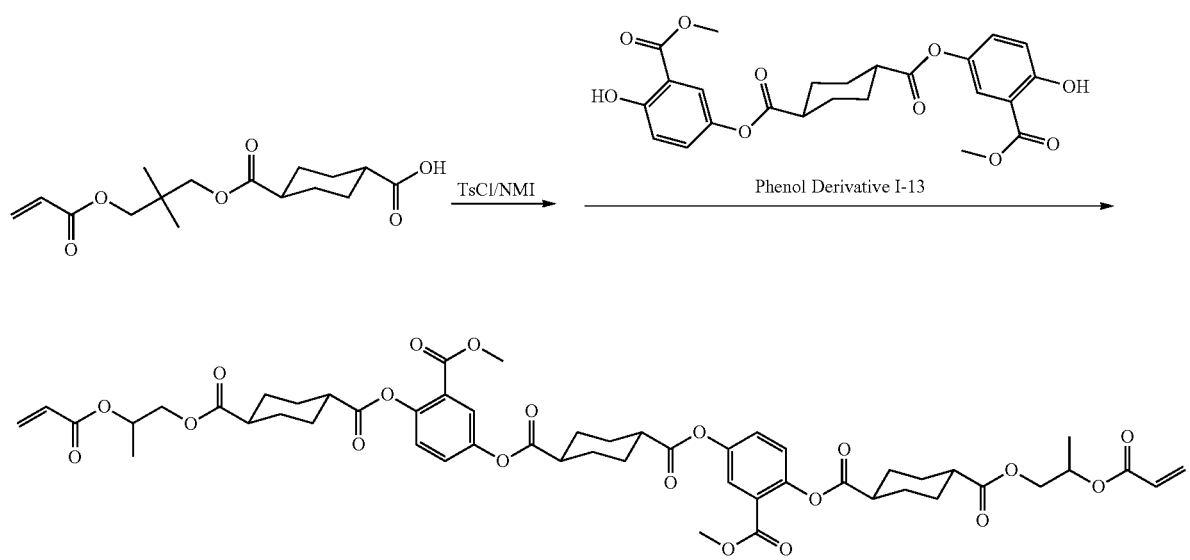

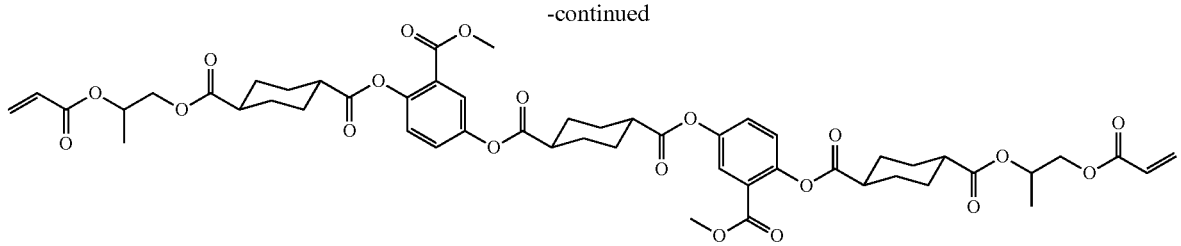

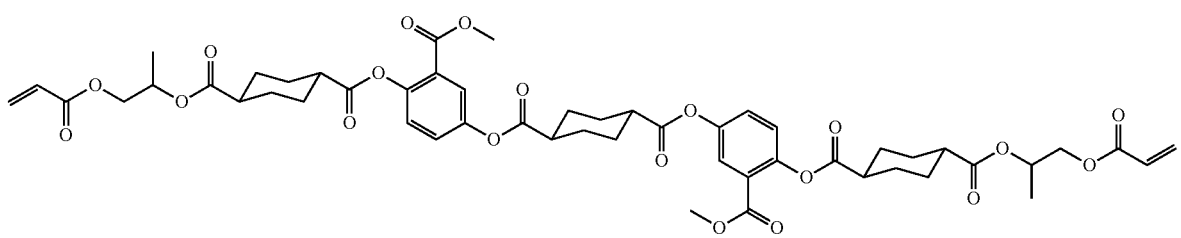

A carboxylic acid was synthesized by the same method as that of the compound I-10. Further, a mixture of compounds 66, 67, and 68 was obtained by using the same synthesis method as that of the compound 55, and by being purified by a column chromatography.

$^1$H-NMR(Solvent: CDCl$_3$)δ(ppm):
1.2-1.3 (m, 6H), 1.5-1.7 (m, 12H), 2.1-2.2 (m, 4H), 2.2-2.4 (m, 10H), 2.6-2.7 (m, 4H), 3.9 (s, 6H), 4.1-4.3 (m, 4H), 5.2-5.3 (m, 2H), 5.8-5.9 (m, 2H), 6.1-6.2 (m, 2H), 6.4-6.5 (m, 2H), 7.1 (d, 2H), 7.3 (dd, 2H), 7.7 (d, 2H)

(Synthesis of Compound I-1-56)

by a small amount, and was stirred for 3 hours. 1 M of a dilute hydrochloric acid was added, and was further stirred for 5 minutes, and then, ethyl acetate was added, a water layer was removed, an organic layer was washed with a dilute hydrochloric acid, a saturated sodium bicarbonate aqueous solution, and saline in this order. The organic layer was dried with magnesium sulfate, the desiccant was filtered, and then, BHT (0.1 g) was added, and the solvent was distilled under reduced pressure.

Next, 7 mL of tetrahydrofuran, 0.12 mL of water, and 0.12 g of p-toluene sulfonate monohydrate were added to a

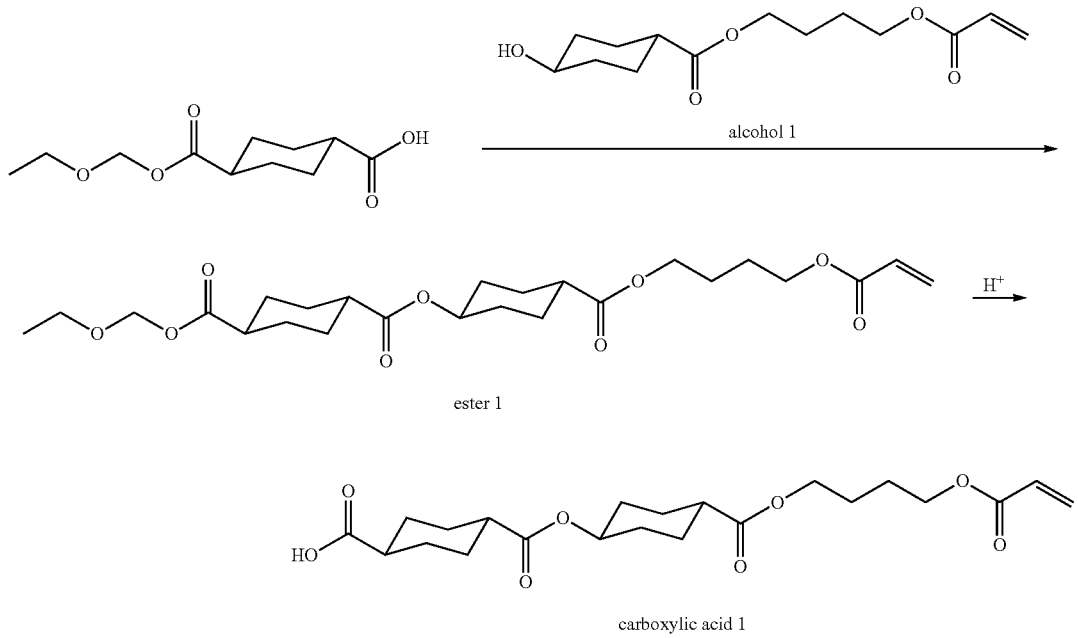

Trans-1,4-cyclohexane dicarboxylic acid monoethoxy methyl ester (1.5 g) was stirred in dimethyl acetoamide (7 mL), an alcohol derivative (2.0 g), BHT (0.1 g), and dimethyl aminopyridine (0.08 g) were added, and the mixture was cooled at 0° C. 1-(3-dimethyl aminopropyl)-3-ethyl carbodiimide hydrochloride (WSCD HCl) (1.5 g) was added reaction composition ester derivative 1, and were stirred at 50° C. for 2 hours. The solvent was distilled under reduced pressure, normal hexane was added, the generated crystal was filtered and dissolved in ethyl acetate, and purification was performed by a silica gel column chromatography, and thus, a carboxylic acid derivative 1 was obtained.

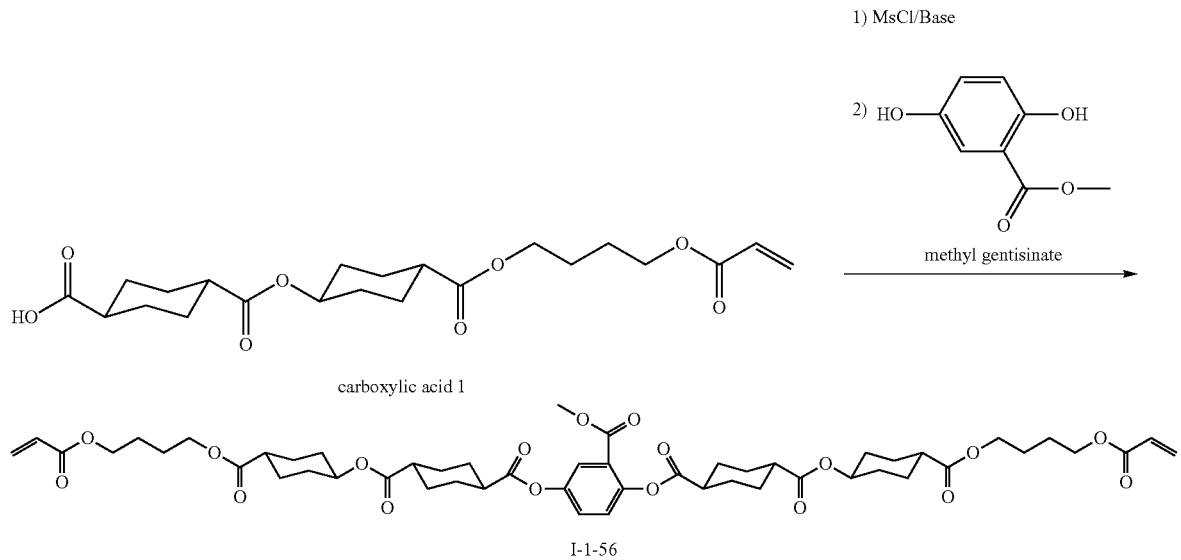

carboxylic acid 1

I-1-56

A solution in which a carboxylic acid derivative 1 (1.0 g) was mixed with ethyl acetate (3 mL) and diisopropyl ethyl amine (0.45 mL) was slowly dropped in a tetrahydrofuran (4 mL) solution of methane sulfonyl chloride (0.2 mL) under ice cooling. The mixture was stirred for 1 hour under ice cooling, and then, a tetrahydrofuran (4 mL) solution of dimethyl aminopyridine (0.03 g) and gentistic acid methyl (0.16 g) was dropped in the mixture, and then, triethyl amine (0.35 mL) was slowly dropped under ice cooling. The mixture was stirred at a reaction temperature of 20° C. for 3 hours, and then, methanol was added, water and ethyl acetate were further added, a water layer was removed, and an organic layer was washed with a saturated sodium bicarbonate aqueous solution, a dilute hydrochloric acid, and saline in this order. The organic layer was dried with magnesium sulfate, the desiccant was filtered, and then, BHT (0.1 g) was added, the solvent was distilled under reduced pressure, and purification was performed by a silica gel column chromatography, and thus, 0.7 g of a compound I-1-56 was obtained.

$^1$H-NMR(Solvent: CDCl$_3$)δ(ppm):

1.35-1.8 (m, 30H), 2.0-2.4 (m, 18H), 2.5-2.7 (m, 2H), 3.85 (s, 3H), 4.1-4.25 (m, 8H), 4.7-4.8 (m, 2H), 5.8 (dd, 2H), 6.15 (dd, 2H), 6.4 (dd, 2H), 7.1 (dd, 1H), 7.3 (dd, 1H), 7.8 (d, 1H)

<Measurement of Birefringence 1>

Birefringences (Δn) of each of the compounds synthesized as described above and a known compound of the related art were measured according to a method disclosed in p. 202 of Liquid Crystal Handbook (Editorial Committee of Liquid Crystal Handbook). Specifically, a sample was injected into a wedge type cell, and was irradiated with laser light at a wavelength of 550 nm, and a refraction angle of transmission light was measured, and thus, Δn at 60° C. was obtained. Liquid crystal compositions in which each of the compounds synthesized as described above or the known compound of the related art were mixed according to Table described below were used as the sample. In Examples 1 to 4, and Comparative Example 1, the precipitation of the crystal was not observed during the measurement, but in Comparative Example 2, the crystal was precipitated during the measurement, and thus, Δn was not able to be measured.

TABLE 1

| | Compound | Added Amount (Parts by Mass) | M-1 (Additive) (Parts by Mass) | Δn |
|---|---|---|---|---|
| Example 1 | 20 | 100 | 0 | 0.107 |
| Example 2 | 28 | 100 | 0 | 0.093 |
| Example 3 | 16 | 100 | 0 | 0.080 |
| Example 4 | Mixture A | 100 | 0 | 0.082 |
| Example 5 | 20 | 33 | 66 | 0.148 |
| Example 6 | 52 | 100 | 0 | 0.070 |
| Example 7 | 54 | 100 | 0 | 0.072 |
| Example 8 | 55 | 100 | 0 | 0.058 |
| Comparative Example 1 | M-1 | 100 | 0 | 0.175 |
| Comparative Example 2 | M-2 | 33 | 66 | Measurement Unavailable |

Compound (M-1)

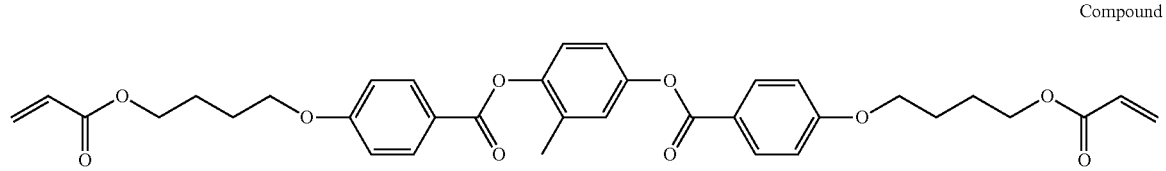

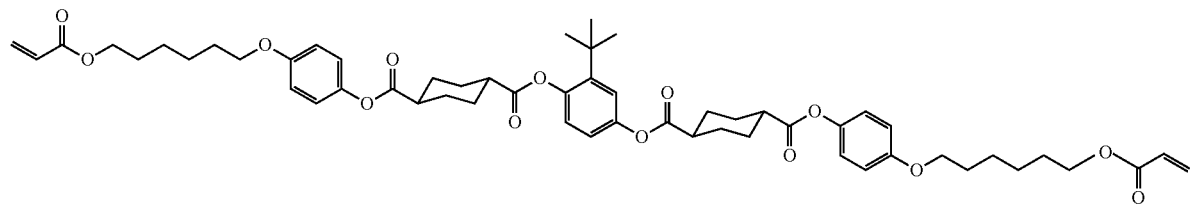

Compound (M-2)

Compound Disclosed in JP2010-270108A

<Measurement of Birefringence 2>

The birefringence ($\Delta n$) of a liquid crystal composition in which compound I-1-56 and a compound M-3 described below were mixed was measured according to a method disclosed in p. 202 of Liquid Crystal Handbook (Editorial Committee of Liquid Crystal Handbook). Specifically, the liquid crystal composition described above which was obtained by mixing the compound I-1-56 (50 parts by mass) and the compound M-3 (50 parts by mass) described below was injected into a wedge type cell, and an interval between stripes observed in crossed nicol conditions was measured by using light at a wavelength of 550 nm, and thus, $\Delta n$ at 50° C. was obtained. The obtained $\Delta n$ was 0.066.

<Preparation of Retardation Film>

A liquid crystalline composition coating liquid (1) having the following composition was prepared by using an exemplary compound synthesized as described above.

| | |
|---|---|
| Compound 20 | 50 parts by mass |
| Compound (M-1) | 50 parts by mass |
| Air Interface Alignment Agent (1) | 0.15 parts by mass |
| Polymerization Initiator IRGACURE819 (manufactured by BASF SE) | 2 parts by mass |
| Solvent Chloroform | 900 parts by mass | ment film at room temperature by a spin coating method, and was aligned and matured at 100° C. for 1 minute, and then, light irradiation was performed at 50° C. for 30 seconds under a nitrogen gas atmosphere by using a high pressure mercury lamp, the alignment was immobilized, and thus, a retardation film 1 was formed. The precipitate of the crystal was not observed in a coated film during a period from the coating to the heating.

As a result of measuring the prepared retardation film in a Tip-Tilt mode by using AxoScan manufactured by Axometrics, Inc, it was confirmed that the average tilt angle of the liquid crystal calculated by the device was 0.8 degrees, and an A-plate type retardation film was able to be formed. In addition, the retardation measured by using the device was 211 nm.

In addition, the film thickness measured by using a non-contact three-dimensional surface shape measurement system (BW-A501, manufactured by Nikon Corporation) was 1.9 nm, and $\Delta n$ at a wavelength of 550 nm calculated from a ratio of the retardation and the film thickness was 0.111.

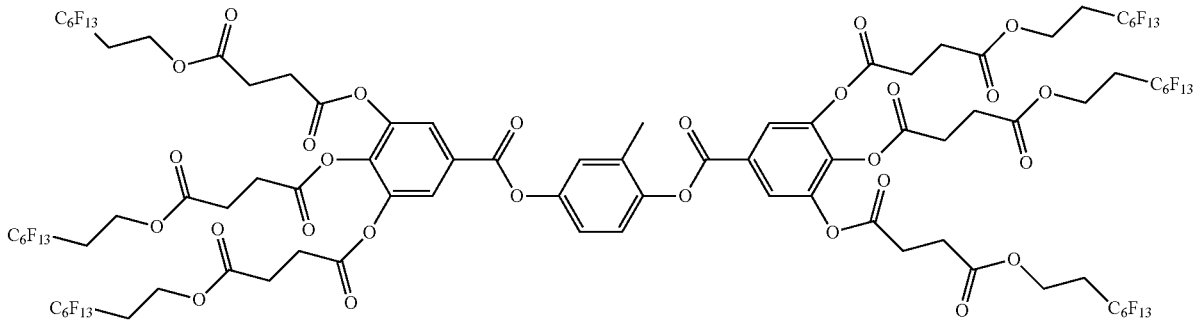

Air Interface Alignment Agent (1)

Next, a washed glass substrate was coated with a polyimide alignment film SE-130 manufactured by Nissan Chemical Industries, Ltd. by a spin coating method, and was dried, and then, was calcinated at 250° C. for 1 hour. A substrate with an alignment film was prepared by performing a rubbing treatment with respect to the polyimide alignment film on the glass substrate. The liquid crystalline composition coating liquid (1) was applied onto a rubbing treatment surface of the prepared substrate with an align- In the polymerizable composition coating liquid (1), retardation films 2 to 11 were prepared by using polymerizable composition coating liquids in which the compound 20 was changed to each of the compound 44, the compound 16, the polymerizable liquid crystal compound (M-2), the compound 50, the compound 53, the compound 54, the compound 55, the compound 57, the compound 59, the compound 62, and the compound 60, and by using the same method as that of the retardation film 1, and $\Delta n$ was calculated by using the same measurement method as that of the retardation film 1. The results are shown in Table 2.

At this time, when the compound 20, the compound 44, the compound 50, the compound 16, the compound 53, the compound 54, the compound 55, the compound 57, the compound 59, the compound 62, and the compound 60 were used, the precipitation of the crystal was not observed during a period from the coating to the polymerization, but when the polymerizable liquid crystal compound (M-2) was used, the precipitation of the crystal was observed on a part of the coated surface during a period from the coating to the polymerization, and thus, an uneven surface was obtained.

light irradiation was performed at 50° C. for 30 seconds under a nitrogen gas atmosphere by using a high pressure mercury lamp, the alignment was immobilized, and thus, a retardation film 12 was formed. The precipitate of the crystal was not observed in a coated film during a period from the coating to the heating.

As a result of measuring the prepared retardation film in a Tip-Tilt mode by using AxoScan manufactured by Axometrics, Inc, it was confirmed that the average tilt angle of the liquid crystal calculated by the device was 1.0 degree and an A-plate type retardation film was able to be formed. In addition, the retardation measured by using the device

TABLE 2

| Retardation Film | Compound | Added Amount (Parts by Mass) | M-1 (Parts by Mass) | Polymerization Initiator (Parts by Mass) | Air Interface Alignment Agent (1) (Parts by Mass) | Retardation (nm) | Film Thickness (μm) | Δn |
|---|---|---|---|---|---|---|---|---|
| 1 | 20 | 50 | 50 | 2 | 0.15 | 211 | 1.9 | 0.111 |
| 2 | 44 | 50 | 50 | 2 | 0.15 | 207 | 1.9 | 0.109 |
| 3 | 16 | 50 | 50 | 2 | 0.15 | 185 | 1.8 | 0.103 |
| 4 | M-2 | 50 | 50 | 2 | 0.15 | 234 | 2.0 | 0.117 |
| 5 | 50 | 50 | 50 | 2 | 0.15 | 258 | 2.3 | 0.112 |
| 6 | 53 | 50 | 50 | 2 | 0.15 | 242 | 2.2 | 0.110 |
| 7 | 54 | 50 | 50 | 2 | 0.15 | 237 | 2.2 | 0.109 |
| 8 | 55 | 50 | 50 | 2 | 0.15 | 233 | 2.3 | 0.102 |
| 9 | 57 | 50 | 50 | 2 | 0.15 | 216 | 2.2 | 0.098 |
| 10 | 59 | 50 | 50 | 2 | 0.15 | 216 | 2.0 | 0.108 |
| 11 | 62 | 50 | 50 | 2 | 0.15 | 198 | 2.0 | 0.099 |
| 12 | 60 | 50 | 50 | 2 | 0.15 | 202 | 1.9 | 0.106 |

<Preparation of Retardation Film>

A liquid crystalline composition coating liquid (13) having the following composition was prepared by using an exemplary compound synthesized in the examples described above.

| | |
|---|---|
| Mixture of Compounds 66 to 68 | 50 parts by mass |
| Compound (M-1) | 50 parts by mass |
| Air Interface Alignment Agent (1) | 0.15 parts by mass |
| Polymerization Initiator IRGACURE819 (manufactured by BASF SE) | 2 parts by mass |
| Solvent Chloroform | 900 parts by mass |

Next, a washed glass substrate was coated with a polyimide alignment film SE-130 manufactured by Nissan Chemical Industries, Ltd. by a spin coating method, and was dried, and then, was calculated at 250° C. for 1 hour. A substrate with an alignment film was prepared by performing a rubbing, treatment with respect to the polyimide alignment film on the glass substrate. The liquid crystalline composition coating liquid (13) was applied onto a rubbing treatment surface of the prepared substrate with an alignment film at room temperature by a spin coating method, and was aligned and matured at 130° C. for 1 minute, and then, was 200 nm. In addition, the film thickness measured by using a non-contact three-dimensional surface shape measurement system (BW-A501, manufactured by Nikon Corporation) was 1.8 nm, and Δn at a wavelength of 550 nm calculated from a ratio of the retardation and the film thickness was 0.112.

<Formation of Selective Reflection Film 1>

A liquid crystalline composition coating liquid (111) having the following composition was prepared by using an exemplary compound synthesized as described above.

| | |
|---|---|
| Compound 28 | 80 parts by mass |
| Compound (M-3) | 20 parts by mass |
| Trimethylol Propane Triacrylate | 5 parts by mass |
| Chiral Agent LC-756 (manufactured by BASF SE) | 6 parts by mass |
| Air Interface Alignment Agent (1) | 0.1 parts by mass |
| Polymerization Initiator IRGACURE819 (manufactured by BASF SE) | 4 parts by mass |
| Solvent Chloroform | 300 parts by mass |

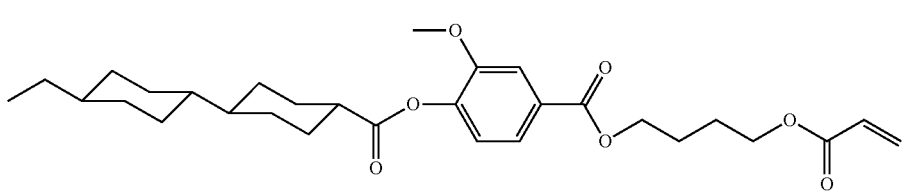

Compound (M-3)

Next, a washed glass substrate was coated with a polyimide alignment film SE-130 manufactured by Nissan Chemical Industries, Ltd. by a spin coating method, and was dried, and then, was calcinated at 250° C. for 1 hour. A substrate with an alignment film was prepared by performing a rubbing treatment with respect to the polyimide alignment film on the glass substrate. The liquid crystalline composition coating liquid (111) was applied onto a rubbing treatment surface of the prepared substrate with an alignment film at room temperature by a spin coating method, and was aligned and matured at 120° C. for 2 minutes, and then, UV irradiation was performed at 70° C. under a nitrogen gas atmosphere by using a high pressure mercury lamp such that the irradiation dose became 300 mJ/cm$^2$, the alignment was immobilized, and a selective reflection layer (111) was formed, and thus, a selective reflection film 1 was obtained. The precipitate of the crystal was not observed in a coated film during a period from the coating to the heating. The thickness of the coated film was 5.2 μm.

As a result of observing the selective reflection layer (111), which was obtained aligning and immobilizing the liquid crystal composition, by using a polarizing microscope, uniform alignment having no alignment defect was confirmed. Further, as a result of measuring the transmission spectrum of the selective reflection film 1 by using a spectrophotometer UV-3100PC manufactured by SHIMADZU CORPORATION, the center of the selective reflection peak was at 472 nm, and the half-width thereof was 27 nm. A ratio (Δλ/λ) of a half-width in a selective reflection wavelength range to the center wavelength of selective reflection was 0.057.

The obtained transmission spectrum is illustrated in FIG. 1.

<Formation of Selective Reflection Film 2>

A liquid crystal composition coating liquid (112) having the following composition was prepared.

| | |
|---|---|
| Compound (M-1) | 100 parts by mass |
| Chiral Agent LC-756 (manufactured by BASF SE) | 5.4 parts by mass |
| Air Interface Alignment Agent (1) | 0.1 parts by mass |
| Polymerization Initiator IRGACURE819 (manufactured by BASF SE) | 3 parts by mass |
| Solvent Chloroform | 300 parts by mass |

A selective reflection layer (112) was formed by the same procedure as that of the formation of the selective reflection layer (111) except that the liquid crystal composition coating liquid (112) was used instead of the liquid crystalline composition coating liquid (111) described above, and thus, a selective reflection film 2 was obtained. At this time, the precipitation of the crystal was observed on a part of the coated surface during a period from the coating of the coating liquid (112) to the polymerization of the coating liquid (112), and thus, an uneven surface was obtained.

As a result of measuring the transmission spectrum of an even portion of the selective reflection film 2, the center of the selective reflection peak was at 569 nm, and the half-width thereof was 71 nm. A ratio (Δλ/λ) of a half-width in a selective reflection wavelength range to the center wavelength of selective reflection was 0.125.

<Formation of Selective Reflection Film 3>

A liquid crystal composition coating liquid (113) having the following composition was prepared by using an exemplary compound synthesized as described above.

| | |
|---|---|
| Compound 55 | 100 parts by mass |
| Chiral Agent LC-756 (manufactured by BASF SE) | 4.2 parts by mass |
| Air Interface Alignment Agent (1) | 0.1 parts by mass |
| Polymerization Initiator IRGACURE819 (manufactured by BASF SE) | 3 parts by mass |
| Solvent Methyl Ethyl Ketone | 180 parts by mass |
| Cyclohexanone | 20 parts by mass |

The polymerizable composition coating liquid (113) was applied onto a rubbing treatment surface of PET manufactured by Fujifilm Corporation, which had been subjected to a rubbing treatment, at room temperature by using a wire bar such that the thickness of a dried film after being dried became 3.3 μm. The coated layer was dried at room temperature for 30 seconds, and then, was heated in an atmosphere of 75° C. for 2 minutes, UV irradiation was performed at 50° C. under a nitrogen gas atmosphere by using a high pressure mercury lamp such that the irradiation dose became 300 mJ/cm$^2$, and a selective reflection layer (113) was formed, and thus, a selective reflection film 3 was obtained. The precipitate of the crystal was not observed in a coated film during a period from the coating to the heating.

Figure 2:
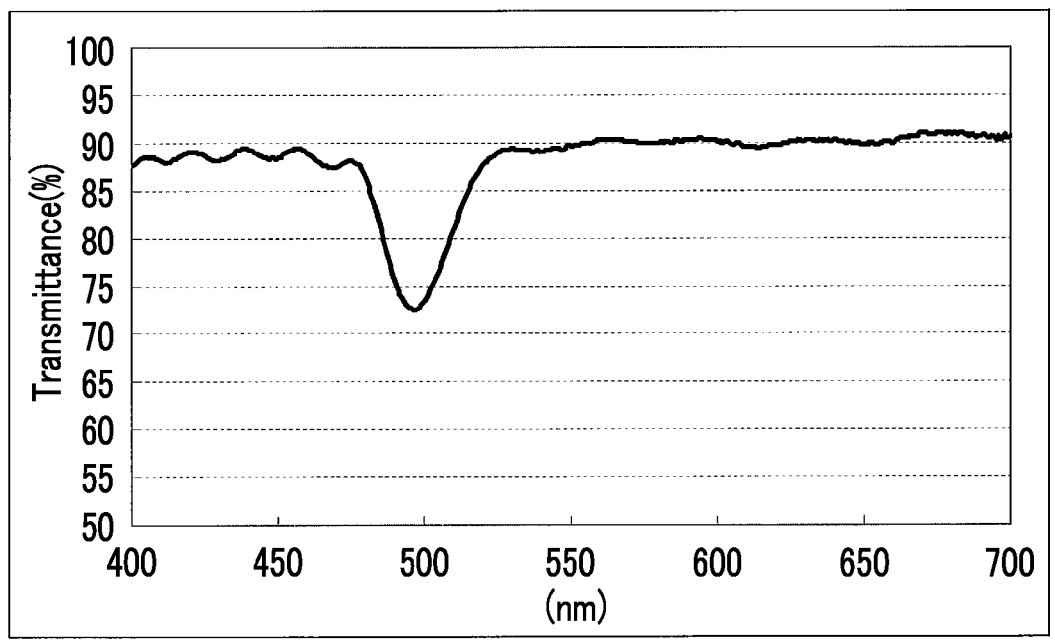
FIG. 2 is a diagram illustrating a transmission spectrum of a selective reflection film 3 prepared in an example.

As a result of observing the selective reflection layer (113) by using a polarizing microscope, uniform alignment having no alignment defect was confirmed. Further, as a result of measuring the transmission spectrum of the selective reflection film 3 by using a spectrophotometer UV-3100PC manufactured by SHIMADZU CORPORATION, the center of the selective reflection peak was at 498 nm, and the half-width thereof was 23 nm. A ratio (Δλ/λ) of a half-width in a selective reflection wavelength range to the center wavelength of selective reflection was 0.046. The obtained transmission spectrum was illustrated in FIG. 2.

<Formation of Selective Reflection Film 4>

A liquid crystalline composition coating liquid (114) having the following composition was prepared by using an exemplary compound synthesized as described above.

| | |
|---|---|
| Compound 55 | 70 parts by mass |
| Compound 62 | 30 parts by mass |
| Chiral Agent LC-756 (manufactured by BASF SE) | 3.6 parts by mass |
| Air Interface Alignment Agent (2) | 0.05 parts by mass |
| Polymerization Initiator IRGACURE819 (manufactured by BASF SE) | 3 parts by mass |
| Solvent Methyl Acetate | 230 parts by mass |

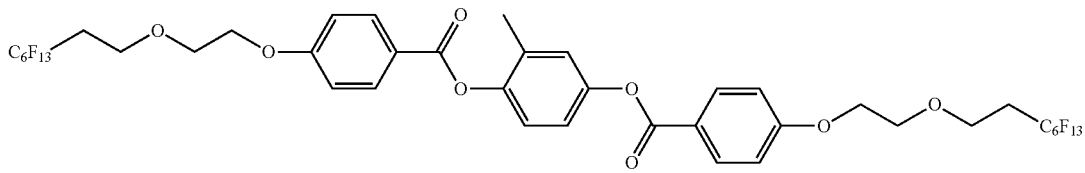

Air Interface Alignment Agent (2)

A liquid crystalline composition coating liquid (115) having the following composition was prepared by using an exemplary compound synthesized as described above.

| | |
|---|---|
| Compound 55 | 70 parts by mass |
| Compound 62 | 30 parts by mass |
| Chiral Agent LC-756 (manufactured by BASF SE) | 4.1 parts by mass |
| Air Interface Alignment Agent (2) | 0.05 parts by mass |
| Polymerization Initiator IRGACURE819 (manufactured by BASF SE) | 3 parts by mass |
| Solvent Methyl Acetate | 230 parts by mass |

A liquid crystalline composition coating liquid (116) having the following composition was prepared by using an exemplary compound synthesized as described above.

| | |
|---|---|
| Compound 55 | 70 parts by mass |
| Compound 62 | 30 parts by mass |
| Chiral Agent LC-756 (manufactured by BASF SE) | 4.8 parts by mass |
| Air Interface Alignment Agent (2) | 0.05 parts by mass |
| Polymerization Initiator IRGACURE819 (manufactured by BASF SE) | 3 parts by mass |
| Solvent Methyl Acetate | 230 parts by mass |

The polymerizable composition coating liquid (114) was applied onto a rubbing treatment surface of PET manufactured by Fujifilm Corporation, which had been subjected to a rubbing treatment, at room temperature by using a wire bar such that the thickness of a dried film after being dried became 4.5 µm. The coated layer was dried at room temperature for 30 seconds, and then, was heated in an atmosphere of 75° C. for 2 minutes, and UV irradiation was performed at 55° C. under a nitrogen gas atmosphere by using a high pressure mercury lamp such that the irradiation dose became 300 mJ/cm$^2$, and thus, a selective reflection layer (114) was formed. The precipitate of the crystal was not observed in a coated film during a period from the coating to the heating.

Subsequently, the polymerizable composition coating liquid (115) was applied onto the selective reflection layer (114) at room temperature by using a wire bar such that the thickness of a dried film after being dried became 3.8 µm (the total film thickness with an underlayer became 8.3 µm). The coated layer was dried at room temperature for 30 seconds, and then, was heated in an atmosphere of 75° C. for 2 minutes, and UV irradiation was performed at 55° C. under a nitrogen gas atmosphere by using a high pressure mercury lamp such that the irradiation dose became 300 mJ/cm$^2$, and thus, a selective reflection layer (115) was formed.

Further, the polymerizable composition coating liquid (116) was applied onto the selective reflection layer (115) at room temperature by using a wire bar such that the thickness of a dried film after being dried became 2.8 µm (the total film thickness with an underlayer became 11.1 µm). The coated layer was dried at room temperature for 30 minutes, and then, was heated in an atmosphere of 70° C. for 1 minute, UV irradiation was performed at 55° C. under a nitrogen gas atmosphere by using a high pressure mercury lamp such that the irradiation dose became 300 mJ/cm$^2$, and a selective reflection layer (116) was formed, and thus, a selective reflection film 4 was obtained.

Figure 3:
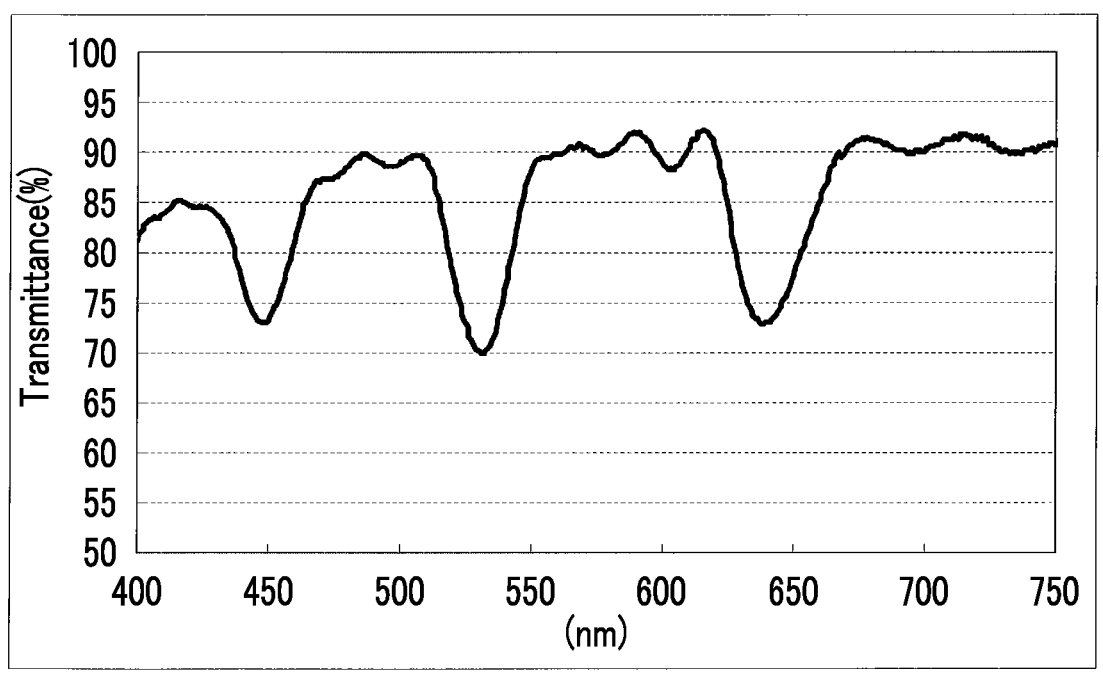
FIG. 3 is a diagram illustrating a transmission spectrum of a selective reflection film 4 prepared in an example.

As result of measuring the transmission spectrum of the selective reflection film 4 by using a spectrophotometer UV-3100PC manufactured by SHIMADZU CORPORATION, it was found that the reflection peak was at 449 nm, 532 nm, and 640 nm, high visible light transmittance of greater than or equal to 80% was obtained. The obtained transmission spectrum is illustrated in FIG. 3.

<Preparation of Half Mirror 1>

A UV curable type adhesive Exp.U12034-6 manufactured by DIC Corporation was applied onto the selective reflection layer (116) side of the selective reflection film 4 at room temperature by using a wire bar such that the thickness of a dried film after being dried became 5 µm. The surface of a methacryl transparent substrate ("ACRYLITE L" manufactured by Mitsubishi Rayon Co., Ltd.) having a thickness of 5 mm, in which the maximum retardation in a plane of 10 cm square where in-plane color unevenness was not visible was 5 nm, and the surface of the selective reflection film 4 coated with an adhesive were bonded in a state where a polarizing plate was orthogonally disposed between the surfaces, UV irradiation was performed, and a PET film of the selective reflection film 4 was peeled off, and thus, a half mirror for displaying a projection image 1 was prepared on an acrylic substrate.

<Preparation of Half Mirror 2 with Antireflection Layer>

A film with an antireflection layer having surface reflectivity at 550 nm of 0.4% was prepared in which a hard coat layer having a refractive index of 1.52 and a thickness of 3.0 µm was formed on a TAC film having a thickness of 40 µm, a layer of intermediate refractive index having a refractive index of 1.594 and a thickness of 0.06 µm was formed thereon, a layer of high refractive index having a refractive index of 1.708 and a thickness of 0.13 µm was further formed thereon, and a layer of low refractive index having a refractive index of 1.343 and a thickness of 0.094 µm was further formed thereon. A UV curable type adhesive Exp.U12034-6 manufactured by DIC Corporation was applied onto the TAC film side at room temperature by using a wire bar such that the thickness of a dried film after being dried became 5 µm. The coated surface and the selective reflection layer (116) side of the selective reflection film 4 prepared as described above were bonded to each other such that air bubbles were prevented from entering, and then, UV irradiation was performed at a temperature of 30° C. and an output of 60% for 6 seconds to 12 seconds by using D BULB manufactured by Heraeus Noblelight America LLC (a lamp of 90 mW/cm), and after that, the PET film of the selective reflection film 4 was peeled off, and thus, a visible light reflection film 11 with an antireflection layer was prepared.

Next, a UV curable type adhesive Exp.U12034-6 manufactured by DIC Corporation was applied onto the selective reflection layer (114) side of the visible light reflection film 11 at room temperature by using a wire bar such that the thickness of a dried film after being dried became 5 μm. The surface of a methacryl transparent substrate ("ACRYLITE L" manufactured by Mitsubishi Rayon Co., Ltd.) having a thickness of 5 mm, in which the maximum retardation in a plane of 10 cm square where in-plane color unevenness was not visible was 5 nm, and the surface of the visible light reflection film 11 coated with an adhesive were bonded in a state where a polarizing plate was orthogonally disposed between the surfaces, UV irradiation was performed, and thus, a half mirror for displaying a projection image 2 was prepared in which an acrylic substrate, the selective reflection layer (114), the selective reflection layer (115), the selective reflection layer (116), and the antireflection layer were provided in this order.

What is claimed is:

1. A polymerizable compound denoted by Formula (I);

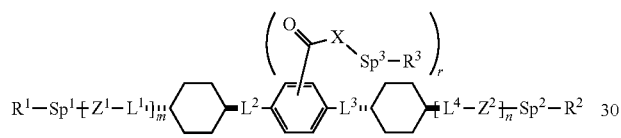

in the formula, $Z^1$ and $Z^2$ each independently represent a trans-1,4-cyclohexylene group which may have a substituent group, an arylene group which may have a substituent group, or a heteroarylene group which may have a substituent group, all of the substituent groups are each independently one to four substituent groups selected from the group consisting of —CO—X-$Sp^3$-$R^3$, an alkyl group, and an alkoxy group, m represents an integer of 1 or 2, and n represents an integer of 0 or 1, when m represents 2, n represents 0, when m represents 2, two $Z^1$'s may be identical to each other or different from each other, $L^1$, $L^2$, $L^3$, and $L^4$ each independently represent a linking group selected from the group consisting of a single bond, —O—, —CH$_2$O—, —OCH$_2$—, —(CH$_2$)$_2$OC(=O)—, —C(=O)O(CH$_2$)$_2$—, —NH—, N(CH$_3$)—, —S—, —C(=O)O—, —OC(=O)—, —OC(=O)O—, —C(=O)N(T$^3$)-, —N(T$^3$)C(=O)—, —C(=O)S—, —SC(=O)—, —CH$_2$C(=O)O—, —OC(=O)CH$_2$—, —CH=CH—C(=O)O—, —OC(=O)—CH=CH—, —CH=N—, —N=CH—, and —N=N—, T$^3$ represents -Sp$^4$-R$^4$, X represents —O—, —S—, or —N(Sp$^5$-R$^5$)—, or represents a nitrogen atom forming a cyclic structure along with R$^3$ and Sp$^3$, r represents an integer of 1 to 4, Sp$^1$, Sp$^2$, Sp$^3$, Sp$^4$, and Sp$^5$ each independently represent a linking group selected from the group consisting of a single bond, a straight chain or branched alkylene group having 1 to 20 carbon atoms, and a group in which one or two or more —CH$_2$—'s in a straight chain or branched alkylene group having 1 to 20 carbon atoms are substituted with —O—, —S—, —NH—, —N(CH$_3$)—, —C(=O)—, —OC(=O)—, or —C(=O)O—, R$^1$ and R$^2$ each independently represent any one polymerizable group selected from the group consisting of groups denoted by Formula (Q-1) to Formula (Q-5) described below, and R$^3$, R$^4$, and R$^5$ each independently represent a hydrogen atom, a cycloalkyl group, a group in which one or two or more —CH$_2$—'s in a cycloalkyl group are substituted with —O—, —S—, —NH—, —N(CH$_3$)—, —C(=O)—, —OC(=O)—, or —C(=O)O—, or any one polymerizable group selected from the group consisting of the groups denoted by Formula (Q-1) to Formula (Q-5) described below, and in a case in which X is a nitrogen atom forming a cyclic structure along with R$^3$ and Sp$^3$, R$^3$ may represent a single bond, and when Sp$^5$ is a single bond, R$^5$ is not a hydrogen atom

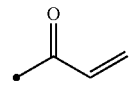
(Q-1)

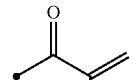
(Q-2)

(Q-3)

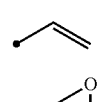
(Q-4)

(Q-5)

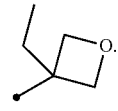

2. The polymerizable compound according to claim 1, wherein the arylene group is a 1,4-phenylene group.

3. The polymerizable compound according to claim 1, wherein at least one of $Z^1$ or $Z^2$ is an arylene group which may have a substituent group or a heteroarylene group which may have a substituent group.

4. The polymerizable compound according to claim 1, wherein m+n is 2.

5. The polymerizable compound according to claim 4, wherein m is 2, and two $Z^1$'s are each a trans-1,4-cyclohexylene group which may have a substituent group and an arylene group which may have a substituent group from an $R^1$ direction, or m is 1, n is 1, $Z^1$ is an arylene group which may have a substituent group, and $Z^2$ is an arylene group which may have a substituent group.

6. The polymerizable compound according to claim 1, wherein $R^1$ and $R^2$ each independently represent the group denoted by Formula (Q-1) or the group denoted by Formula (Q-2).

7. The polymerizable compound according to claim 1, wherein all of $L^1$, $L^2$, $L^3$, and $L^4$ are —C(=O)O— or —OC(=O)—.

8. The polymerizable compound according to claim 6, wherein all of $L^1$, $L^2$, $L^3$, and $L^4$ are —C(=O)O— or —OC(=O)—.

9. The polymerizable compound according to claim 1,
wherein m is 1, n is 1, r is 1, $Sp^3$ is a straight chain or branched alkylene group having 1 to 20 carbon atoms, and $R^3$ is a hydrogen atom.

10. The polymerizable compound according to claim 1,
wherein m is 1, n is 1, and both of $Z^1$ and $Z^2$ are a trans-1,4-cyclohexylene group which may have a substituent group.

11. A polymerizable composition, containing: the polymerizable compound according to claim 1.

12. The polymerizable composition according to claim 11, further containing:
other liquid crystal compounds along with the polymerizable compound denoted by Formula (I).

13. The polymerizable composition according to claim 11, further containing:
a chiral compound.

14. A film, comprising:
a layer obtained by curing the polymerizable composition according to claim 11.

15. A film, comprising:
two or more layers obtained by curing the polymerizable composition according to claim 11.

16. The film according to claim 14,
wherein the film has selective reflection, and
$\Delta\lambda/\lambda$ which is a ratio of a half-width $\Delta\lambda$ in a wavelength range of the selective reflection to a center wavelength $\lambda$ of the selective reflection is less than or equal to 0.09.

17. A film, comprising:
at least three layers formed of the polymerizable composition according to claim 11,
wherein the three layers are a layer formed by immobilizing a cholesteric liquid crystalline phase having a center wavelength of selective reflection in a red light wavelength range, a layer formed by immobilizing a cholesteric liquid crystalline phase having a center wavelength of selective reflection in a green light wavelength range, and a layer formed by immobilizing a cholesteric liquid crystalline phase having a center wavelength of selective reflection in a blue light wavelength range.

18. A half mirror for displaying a projection image, comprising:
the film according to claim 17.

19. The half mirror for displaying a projection image according to claim 18, further comprising:
a substrate which is inorganic glass or an acrylic resin.

20. The half mirror for displaying a projection image according to claim 18, further comprising:
an antireflection layer on an outermost surface.

* * * * *